US011479582B2

(12) United States Patent
Elsayed et al.

(10) Patent No.: US 11,479,582 B2
(45) Date of Patent: Oct. 25, 2022

(54) ANTI-SARS-COV-2 FUSION PEPTIDES

(71) Applicant: KING FAISAL UNIVERSITY, Al-Ahsa (SA)

(72) Inventors: Mahmoud Kandeel Elsayed, Al-Ahsa (SA); Mizuki Yamamoto, Kanagawa (JP); Jin Gohda, Kanagawa (JP); Jun-Ichiro Inoue, Tokyo (JP); Yasushi Kawaguchi, Tokyo (JP); Hyung-Joo Kwon, Cheongju (KR); Abdulla Al-Taher, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 17/410,172

(22) Filed: Aug. 24, 2021

(65) Prior Publication Data

US 2022/0119456 A1 Apr. 21, 2022

Related U.S. Application Data

(60) Provisional application No. 63/093,157, filed on Oct. 16, 2020.

(51) Int. Cl.
*C07K 14/005* (2006.01)
*A61K 38/00* (2006.01)
*G01N 33/569* (2006.01)

(52) U.S. Cl.
CPC ..... *C07K 14/005* (2013.01); *G01N 33/56983* (2013.01); *A61K 38/00* (2013.01); *C07K 2319/00* (2013.01); *C12N 2770/20022* (2013.01); *C12N 2770/20033* (2013.01); *G01N 2333/165* (2013.01); *G01N 2496/00* (2013.01)

(58) Field of Classification Search
None
See application file for complete search history.

(56) References Cited

U.S. PATENT DOCUMENTS 7,151,163 B2 12/2006 Erickson et al.
7,491,489 B2 2/2009 Zheng et al.
10,259,848 B2 4/2019 Walensky et al.
2004/0071709 A1 4/2004 Rottier et al.
2004/0229219 A1 11/2004 Gallaher et al.
2006/0257852 A1 11/2006 Rappuoli et al.
2013/0196903 A1 8/2013 Pessi

FOREIGN PATENT DOCUMENTS

| | | | |
|---|---|---|---|
| CN | 108395471 | B | 3/2020 |
| CN | 111349150 | A | 6/2020 |
| CN | 111423508 | A | 7/2020 |
| WO | 2005002500 | A2 | 1/2005 |
| WO | 2005044992 | A2 | 5/2005 |
| WO | 2005080419 | A1 | 9/2005 |
| WO | 2014154134 | A1 | 10/2014 |

OTHER PUBLICATIONS

GenBank Accession AAV97984, spike glycoprotein [SARS coronavirus A001], 2006.*
Kan et al., Molecular Evolution Analysis and Geographic Investigation of Severe Acute Respiratory Syndrome Coronavirus-Like Virus in Palm Civets at an Animal Market and on Farms, 2005, Journal of Virology, vol. 79, No. 18, pp. 11892-11900.*
Zhu et al., "Design of Potent Membrane Fusion Inhibitors against SARS-CoV-2, an Emerging Coranavirus with High Fusogenic Activity," Journal of Virology, 94(14): pp. 1-12, Jul. 1, 2020.

* cited by examiner

*Primary Examiner* — Benjamin P Blumel
(74) *Attorney, Agent, or Firm* — Nath, Goldberg & Meyer; Richard C. Litman

(57) ABSTRACT

Anti-SARS-CoV-2 fusion peptides are provided. The anti-SARS-CoV-2 fusion peptides include peptide sequences corresponding to the sequence of the SARS-CoV-2 fusion complex heptad repeat domain HR2 and having at least one artificial mutation. The anti-SARS-CoV-2 fusion peptides may be 39-mers, such as peptides #121 (SEQ ID NO: 2) and #125 (SEQ ID NO: 5). These peptides may competitively bind to SARS-CoV-2 and prevent either membrane mediated SARS-CoV-2 fusion, endocytosis-mediated viral entry, or both. The anti-SARS-CoV-2 fusion peptides may be administered to a subject in need thereof to inhibit or prevent SARS-CoV-2 cellular entry.

17 Claims, 6 Drawing Sheets

Specification includes a Sequence Listing.

SEQUENCE LISTING

```
<160> NUMBER OF SEQ ID NOS: 9

<210> SEQ ID NO 1
<211> LENGTH: 39
<212> TYPE: PRT
<213> ORGANISM: SARS-CoV-2

<400> SEQUENCE: 1

Val Asp Leu Gly Asp Ile Ser Gly Ile Asn Ala Ser Val Val Asn Ile
1               5                   10                  15

Gln Lys Glu Ile Asp Arg Leu Asn Glu Val Ala Lys Asn Leu Asn Glu
            20                  25                  30

Ser Leu Ile Asp Leu Gln Glu
        35


<210> SEQ ID NO 2
<211> LENGTH: 39
<212> TYPE: PRT
<213> ORGANISM: Artificial Sequence
<220> FEATURE:
<223> OTHER INFORMATION: SARS-COV-2 Mutant #121

<400> SEQUENCE: 2

His Val Leu Gly Asp Ile Ser Gly Ile Asn Ala Ser Val Val Gln Ile
1               5                   10                  15

Gln Lys Glu Ile Asp Arg Leu Asn Glu Val Ala Lys Asn Leu His Glu
            20                  25                  30

Ser Leu Ile Tyr Leu Gln Glu
        35


<210> SEQ ID NO 3
<211> LENGTH: 39
<212> TYPE: PRT
<213> ORGANISM: Artificial Sequence
<220> FEATURE:
<223> OTHER INFORMATION: SARS-CoV-2 Mutant #122

<400> SEQUENCE: 3

Val Asp Leu Gly Asp Ile Ser Gly Ile Arg Ala Met Val Val Arg Ile
1               5                   10                  15

Gln Lys Glu Ile Met Arg Leu Asn Glu Val Ala Lys Asn Leu Asn Glu
            20                  25                  30

Ser Leu Ile Asp Leu Gln Glu
        35
```

-continued

<210> SEQ ID NO 4
<211> LENGTH: 39
<212> TYPE: PRT
<213> ORGANISM: Artificial Sequence
<220> FEATURE:
<223> OTHER INFORMATION: SARS-CoV-2 Mutant #123

<400> SEQUENCE: 4

```
Leu Arg Leu Gly Asp Ile Ser Gly Ile Arg Ala Arg Val Val Arg Ile
1               5                   10                  15

Gln Lys Glu Ile His Arg Leu Asn Glu Val Ala Lys Asn Leu Asn Glu
            20                  25                  30

Ser Leu Ile Asp Leu Gln Asn
        35
```

<210> SEQ ID NO 5
<211> LENGTH: 39
<212> TYPE: PRT
<213> ORGANISM: Artificial Sequence
<220> FEATURE:
<223> OTHER INFORMATION: SARS-CoV-2 Mutant #125

<400> SEQUENCE: 5

```
His Arg Leu Arg Gln Ile Arg Gly Ile Arg Ala Arg Val Val Gln Ile
1               5                   10                  15

Gln Lys Glu Ile Trp Arg Leu Asn Glu Val Ala Lys Leu Leu Asn Glu
            20                  25                  30

Ser Leu Ile Tyr Leu Gln Glu
        35
```

<210> SEQ ID NO 6
<211> LENGTH: 20
<212> TYPE: DNA
<213> ORGANISM: Homo sapiens

<400> SEQUENCE: 6
aaattttggg gaccaggaac 20

<210> SEQ ID NO 7
<211> LENGTH: 20
<212> TYPE: DNA
<213> ORGANISM: Homo sapiens

<400> SEQUENCE: 7
tggcagctgt gtaggtcaac 20

<210> SEQ ID NO 8
<211> LENGTH: 20
<212> TYPE: DNA
<213> ORGANISM: SARS-CoV-2

<400> SEQUENCE: 8
gcaccgtcaa ggctgagaac 20

<210> SEQ ID NO 9
<211> LENGTH: 18
<212> TYPE: DNA
<213> ORGANISM: SARS-CoV-2

<400> SEQUENCE: 9
tggtgaagac gccagtgg 18

ANTI-SARS-COV-2 FUSION PEPTIDES

CROSS-REFERENCE TO RELATED APPLICATION

This application claims the benefit of U.S. Provisional Patent Application No. 63/093,157, filed on Oct. 16, 2020.

INCORPORATION BY REFERENCE OF MATERIAL SUBMITTED IN COMPUTER READABLE FORM

The Applicants hereby incorporate by reference the sequence listing contained in the ASCII text filed titled 32087_34 Sequence_Listing_ST25.txt, created Apr. 27, 2021, and having 3 KB of data.

BACKGROUND

1. Field

The disclosure of the present patent application relates to biotechnology, and particularly to anti-SARS-CoV-2 fusion peptides and methods of using said peptides.

2. Description of the Related Art

The SARS-CoV-2 pandemic that began in 2019 has posed a significant threat worldwide. In the past two decades, three coronaviruses have emerged and endangered public health, including the severe acute respiratory syndrome coronavirus (SARS CoV), Middle East respiratory syndrome CoV (MERS-CoV), and SARS-CoV-2. The SARS-CoV-2 pandemic has necessitated the discovery of new therapeutics to combat the increasing number of infected humans. While a large number of drug repurposing studies have been conducted, the need for more and better therapeutic options for treating SARS-CoV-2 remains.

Thus, anti-SARS-CoV-2 fusion peptides solving the aforementioned problems is desired.

SUMMARY

The anti-SARS-CoV-2 fusion peptides include a set of peptides designed by modification or mutation of a wild type SARS-CoV-2 fusion protein. The anti-SARS-CoV-2 fusion peptides are capable of inhibition of SARS-CoV-2 infection in cells and may be used to prevent and/or treat SARS-CoV-2 infection in a subject in need thereof. The anti-SARS-CoV-2 fusion peptides may prevent membrane-mediated viral entry, endocytosis-mediated viral entry, or prevent both membrane-mediated viral entry and endocytosis-mediated viral entry. The anti-SARS-CoV-2 fusion peptides may also be used as reagents for SARS-CoV-2 inhibition assays as a standard or as reference inhibitors.

In an embodiment, the anti-SARS-CoV-2 fusion peptides are 39-mer amino acid sequences including at least one mutation of the wild type SARS-CoV-2 Heptad Repeat Doman (HR2) sequence. In a further embodiment, the anti-SARS-CoV-2 fusion peptides may be 39-mer amino acid sequences including 1, 2, 3, 4, 5, or 6 mutations of the wild type SARS-CoV-2 HR2 sequence.

An embodiment of the present subject matter is directed to a pharmaceutical composition including one or more of the anti-SARS-CoV-2 fusion peptides and a pharmaceutically acceptable carrier.

An embodiment of the present subject matter is directed to a method of making a pharmaceutical composition including mixing one or more of the anti-SARS-CoV-2 fusion peptides under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to compositions including one or more of the anti-SARS-CoV-2 fusion peptides and one or more expression systems. The expression system may be a viral based expression system, a plasmid-based expression system, or any other expression system suitable for causing or enhancing expression of the anti-SARS-CoV-2 fusion peptides in a bacterium, yeast, or mammalian cell. The expression system may include a promoter sequence and DNA or RNA encoding one or more of the anti-SARS-CoV-2 fusion peptides.

An embodiment of the present subject matter is directed to methods of inhibiting SARS-CoV-2 infection, preventing SARS-CoV-2 transmission, and/or treating a SARS-CoV-2 infection, including administering to a subject in need thereof a therapeutically effective amount of a pharmaceutical composition according to the present subject matter. In a further embodiment, the methods of inhibiting SARS-CoV-2 infection may include preventing SARS-CoV-2 infection of a cell.

An embodiment of the present subject matter is directed to methods of using the anti-SARS-CoV-2 fusion peptides as reference agents to evaluate inhibition by other candidates against SARS-CoV-2. These methods may include using the SARS-CoV-2 fusion peptides as reference agents in Cell-Cell Fusion Assays, Viral Plaque Formation Assays, Viral RNA Quantitation Assays, or the like.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
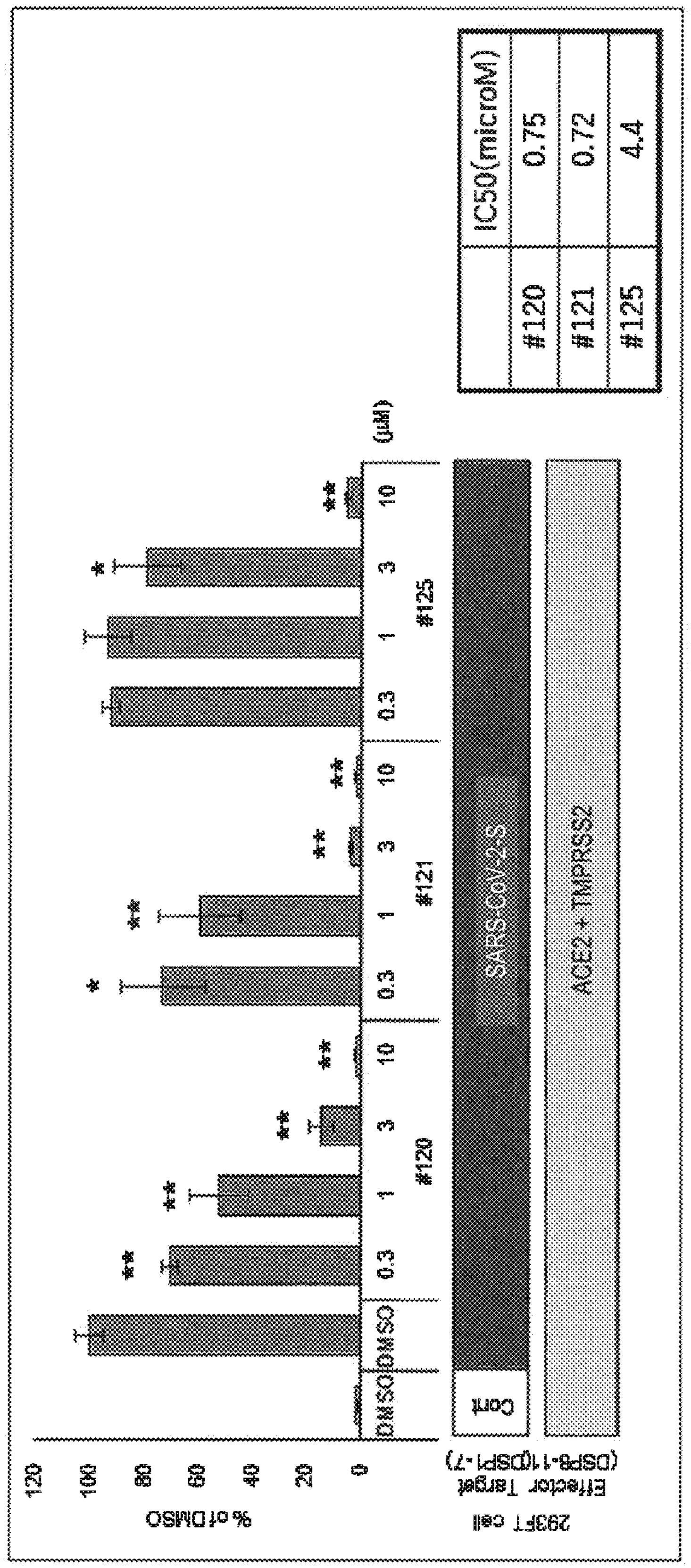
FIG. 1 depicts a graph of the effect of the anti-SARS-CoV-2 fusion peptides on SARS-CoV-2 S-mediated membrane fusion. The graph depicts the effect of each peptide on the co-culture fusion assay using DSP as a reporter. Peptides were tested at different concentrations, and additional proteins other than reporters (DSPs) transduced into the effector and target cells are indicated below the graph. The relative cell fusion was represented as the DSP value (RL activity measured in RLU) normalized to that of the control assay with DMSO alone. (*: $p<0.05$, **: $p<0.01$).

An anti-SARS-CoV-2 fusion peptide include can be synthesized by modification or mutation of a wild type SARS-CoV-2 fusion protein. The present teachings are directed to a plurality of anti-SARS-CoV-2 fusion peptides. The anti-SARS-CoV-2 fusion peptides are capable of inhibition of SARS-CoV-2 infection in cells and may be used to prevent and/or treat SARS-CoV-2 infection in a subject in need thereof. The anti-SARS-CoV-2 fusion peptides may prevent membrane-mediated viral entry, endocytosis-mediated viral entry, or prevent both membrane-mediated viral entry and endocytosis-mediated viral entry. The anti-SARS-CoV-2 fusion peptides may also be used as reagents for SARS-CoV-2 inhibition assays as a standard or as reference inhibitors.

In an embodiment, the anti-SARS-CoV-2 fusion peptide includes a 39-mer amino acid sequence including at least one mutation of the wild type SARS-CoV-2 Heptad Repeat Doman (HR2) sequence. In a further embodiment, the anti-SARS-CoV-2 fusion peptide may include a 39-mer amino acid sequences including 1, 2, 3, 4, 5, or 6 mutations of the wild type SARS-CoV-2 HR2 sequence.

Throughout this application, the term "about" may be used to indicate that a value includes the standard deviation of error for the composition, device or method being employed to determine the value.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

The phrase "pharmaceutically acceptable," as used herein, refers to molecular entities and compositions that do not produce an allergic or similar untoward reaction when administered to a human.

The term "subject," as used herein, means a mammal, including but not limited to a human being.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

An embodiment of the present subject matter is directed to a pharmaceutical composition comprising one or more of the anti-SARS-CoV-2 fusion peptides and a pharmaceutically acceptable carrier.

An embodiment of the present subject matter is directed to a method of making a pharmaceutical composition including mixing one or more of the anti-SARS-CoV-2 fusion peptides with a pharmaceutically acceptable carrier. For example, the method of making a pharmaceutical composition can include mixing an anti-SARS-CoV-2 fusion peptide under sterile conditions with a pharmaceutically acceptable carrier with preservatives, buffers, and/or propellants to create the pharmaceutical composition.

An embodiment of the present subject matter is directed to a pharmaceutical composition including one or more of the anti-SARS-CoV-2 fusion peptides. To prepare the pharmaceutical composition, one or more of the anti-SARS-CoV-2 fusion peptides, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. One or more of the anti-SARS-CoV-2 fusion peptides can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of an anti-SARS-CoV-2 fusion peptides or an amount effective to treat a disease, such as a coronavirus infection, may be determined initially from the Examples described herein and adjusted for specific targeted diseases using routine methods.

An embodiment of the present subject matter is directed to compositions including one or more of the anti-SARS-CoV-2 fusion peptides and one or more expression systems. The expression system may be a viral based expression system, a plasmid-based expression system, or any other expression system suitable for causing or enhancing expression of the anti-SARS-CoV-2 fusion peptides in a bacterium, yeast, or mammalian cell. The expression system may include a promoter sequence and DNA or RNA encoding one or more of the anti-SARS-CoV-2 fusion peptides.

An embodiment of the present subject matter is directed to methods of using the anti-SARS-CoV-2 fusion peptides as reference agents to evaluate inhibition by other candidates against SARS-CoV-2. These methods may include using the anti-SARS-CoV-2 fusion peptides as reference agents in Cell-Cell Fusion Assays, Viral Plaque Formation Assays, Viral RNA Quantitation Assays, or the like.

The anti-SARS-CoV-2 fusion peptides can be administered to a subject in need thereof. In an embodiment, the anti-SARS-CoV-2 fusion peptides can be administered to a subject in need thereof to inhibit SARS-CoV-2 infection, prevent SARS-CoV-2 transmission, and/or treat a SARS-CoV-2 infection.

An embodiment of the present subject matter is directed to a method of inhibiting SARS-CoV-2 infection, preventing SARS-CoV-2 transmission, and/or treating a SARS-CoV-2 infection, comprising administering to a subject in need thereof a therapeutically effective amount of the pharmaceutical composition according to the present subject matter.

The anti-SARS-CoV-2 fusion peptides or pharmaceutical compositions thereof can be administered to a subject by any suitable route. For example, the compositions can be administered nasally, rectally, intracisternally, intraperitoneally, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The viral CoV genome encodes four structural proteins: spike (S), membrane (M), envelope (E), and nucleocapsid (N). Viral membrane fusion is an essential step of virus replication, which is accomplished by the viral spike and leads to the fusion of the viral and cell membranes. The CoV S protein is composed of two subunits, S1 and S2. S1 binds the host cell ACE2 receptor. Cleavage of S1 by host cell proteases exposes a highly hydrophobic membrane-binding domain of the S2 subunit. The S2 subunit contains two domains, heptad repeat domain 1 (HR1) and heptad repeat domain 2 (HR2). HR1 forms a homotrimer exposing three hydrophobic pockets on its surface, which host the HR2 domain during the active fusion process. An HR domain is composed of tandem repeat motifs of seven residues (named a-g). Of the seven residues, the first (a) and fourth (d) are predominantly hydrophobic or bulky.

The anti-SARS-CoV-2 fusion peptides are designed by modification or mutation of a surface structure protein of SARS-CoV-2 in the virus S2 spike region. The heptad repeat regions (HR1 and HR2) of S2 interact to help in fusion of SARS-CoV-2 with cell membranes. The anti-SARS-CoV-2 fusion peptides S2 HR2 derivatives were optimized to interfere with the proper mechanism of HR1-HR2 interactions.

Optimization included in silico modeling of potential mutations in HR2 and the selection of peptides with the highest changes in affinity and stability. (See Example 1, Table 1, for a list of tested mutations) The mutations that gave rise to the selected peptides were then combined in a further in silico energy maturation study. The resulting anti-SARS-CoV-2 fusion peptides possessed up to six mutations compared to the wild type sequence. (See Example 2, Table 2, for examples of possible combinations of mutations)

In an embodiment, the anti-SARS-CoV-2 peptide includes peptide #121 (SEQ ID NO. 2: HVLGDISGINASVVQIQKEIDRLNEVAKNLHESLIYLQE), peptide #122 (SEQ ID NO. 3: VDLGDISGIRAMVVRIQKEMRLNEVAKNLNESLIDLQE), peptide #123 (SEQ ID NO. 4: LRLGDISGIRARVVRIQKEIHRLNEVAKNLNESLIDLQN), or peptide #125 (SEQ ID NO. 5: HRLRQIRGIRARVVQIQKEIWRLNEVAKLLNESLIYLQE).

The following examples illustrate the present subject matter.

Example 1

Mutations of HR2

HR2 amino acid mutations were tested in silico to find the most potent candidate that can bind potently with HR1. (Schrodinger Suite 2020, NY, USA). Protein structures were optimized using the protein preparation wizard, followed by energy minimization and mutation. To ensure reproducibility, the experiment was repeated three times. For this purpose, stepwise mutations were carried out as follows.

Every residue in HR2 was mutated to all of the potential candidates, comprising the twenty known essential amino acids. The mutations were evaluated based on the changes in binding free energy as well as the solvated peptide stability. Table 1 shows the results of initial single amino acids mutations. In Table 1, the Residue # is listed as R #, the original amino acid is listed as "WT", and the mutated amino acid is listed as "MUT". The "Δ Affinity" implies the changes in binding energy (Kcal/mol) after each mutation. The "Δ Stability" implies the changes in solvation stability after each mutation.

TABLE 1

| Single Amino Acid Mutations in HR2 | | | | |
|---|---|---|---|---|
| R # | WT | MUT | Δ Aff. | Δ Stab. |
| 1164 | VAL | ILE | 0 | 5.26 |
| 1164 | VAL | GLN | −0.08 | −44 |
| 1164 | VAL | GLY | −0.19 | 25.92 |
| 1164 | VAL | GLU | 0.94 | −22.5 |
| 1164 | VAL | CYS | 0.2 | −2.67 |
| 1164 | VAL | ASP | 1.77 | −25.7 |
| 1164 | VAL | SER | −0.13 | 0.85 |
| 1164 | VAL | LYS | −0.74 | −6.68 |
| 1164 | VAL | PRO | −0.29 | 42.53 |
| 1164 | VAL | HIE | 0.3 | −9.16 |
| 1164 | VAL | ASN | −0.1 | −36.71 |
| 1164 | VAL | HIP | −1.37 | −11.26 |
| 1164 | VAL | THR | −0.14 | −10.93 |
| 1164 | VAL | HID | −0.04 | −11.42 |
| 1164 | VAL | TRP | 0.23 | −7.29 |
| 1164 | VAL | PHE | 0.07 | 0.13 |
| 1164 | VAL | ALA | −0.05 | 4.21 |
| 1164 | VAL | MET | −0.11 | −6.33 |
| 1164 | VAL | LEU | 0.02 | 9.25 |
| 1164 | VAL | ARG | 1.75 | −35.88 |
| 1164 | VAL | TYR | 0.06 | −9.2 |
| 1164 | VAL | ILE | 0 | 5.26 |
| 1164 | VAL | GLN | −0.08 | −44 |
| 1164 | VAL | GLY | −0.19 | 25.92 |
| 1164 | VAL | GLU | 0.94 | −22.5 |
| 1164 | VAL | CYS | 0.2 | −2.67 |
| 1164 | VAL | ASP | 1.77 | −25.7 |
| 1164 | VAL | SER | −0.13 | 0.85 |
| 1164 | VAL | LYS | −0.74 | −6.68 |
| 1164 | VAL | PRO | −0.29 | 42.53 |
| 1164 | VAL | HIE | 0.3 | −9.16 |
| 1164 | VAL | ASN | −0.1 | −36.71 |
| 1164 | VAL | HIP | −1.37 | −11.26 |
| 1164 | VAL | THR | −0.14 | −10.93 |
| 1164 | VAL | HID | −0.04 | −11.42 |
| 1164 | VAL | TRP | 0.23 | −7.29 |
| 1164 | VAL | PHE | 0.07 | 0.13 |
| 1164 | VAL | ALA | −0.05 | 4.21 |
| 1164 | VAL | MET | −0.11 | −6.33 |
| 1164 | VAL | LEU | 0.02 | 9.25 |
| 1164 | VAL | ARG | 1.75 | −35.88 |
| 1164 | VAL | TYR | 0.06 | −9.2 |
| 1164 | VAL | ILL | 0 | 5.26 |
| 1164 | VAL | GLN | −0.08 | −44 |
| 1164 | VAL | GLY | −0.19 | 25.92 |
| 1164 | VAL | GLU | 0.94 | −22.5 |
| 1164 | VAL | CYS | 0.2 | −2.67 |
| 1164 | VAL | ASP | 1.77 | −25.7 |
| 1164 | VAL | SER | −0.13 | 0.85 |
| 1164 | VAL | LYS | −0.74 | −6.68 |
| 1164 | VAL | PRO | −0.29 | 42.53 |
| 1164 | VAL | HIE | 0.3 | −9.16 |
| 1164 | VAL | ASN | −0.1 | −36.71 |
| 1164 | VAL | HIP | −1.37 | −11.26 |
| 1164 | VAL | THR | −0.14 | −10.93 |
| 1164 | VAL | HID | −0.04 | −11.42 |
| 1164 | VAL | TRP | 0.23 | −7.29 |
| 1164 | VAL | PHE | 0.07 | 0.13 |
| 1164 | VAL | ALA | −0.05 | 4.21 |
| 1164 | VAL | MET | −0.11 | −6.33 |
| 1164 | VAL | LEU | 0.02 | 9.25 |
| 1164 | VAL | ARG | 1.75 | −35.88 |
| 1164 | VAL | TYR | 0.06 | −9.2 |
| 1164 | VAL | ILE | 0 | 5.26 |
| 1164 | VAL | GLN | −0.08 | −44 |
| 1164 | VAL | GLY | −0.19 | 25.92 |
| 1164 | VAL | GLU | 0.94 | −22.5 |
| 1164 | VAL | CYS | 0.2 | −2.67 |
| 1164 | VAL | ASP | 1.77 | −25.7 |
| 1164 | VAL | SER | −0.13 | 0.85 |
| 1164 | VAL | LYS | −0.74 | −6.69 |
| 1164 | VAL | PRO | −0.29 | 42.53 |
| 1164 | VAL | HIE | 0.3 | −9.16 |
| 1164 | VAL | ASN | −0.1 | −36.71 |
| 1164 | VAL | HIP | −1.37 | −11.26 |
| 1164 | VAL | THR | −0.14 | −10.93 |

TABLE 1-continued

| Single Amino Acid Mutations in HR2 | | | | |
|---|---|---|---|---|
| R # | WT | MUT | Δ Aff. | Δ Stab. |
| 1164 | VAL | HID | −0.04 | −11.42 |
| 1164 | VAL | TRP | 0.23 | −7.29 |
| 1164 | VAL | PHE | 0.07 | 0.13 |
| 1164 | VAL | ALA | −0.05 | 4.21 |
| 1164 | VAL | MET | −0.11 | −6.33 |
| 1164 | VAL | LEU | 0.02 | 9.25 |
| 1164 | VAL | ARG | 1.75 | −35.88 |
| 1164 | VAL | TYR | 0.06 | −9.2 |
| 1165 | ASP | ILE | −0.76 | −5.37 |
| 1165 | ASP | GLN | −0.44 | −4.15 |
| 1165 | ASP | GLY | −0.74 | −2.59 |
| 1165 | ASP | GLU | 0.04 | −3.36 |
| 1165 | ASP | CYS | −0.79 | −3.24 |
| 1165 | ASP | SER | −0.77 | −4.57 |
| 1165 | ASP | LYS | −1.34 | −1.03 |
| 1165 | ASP | PRO | −0.88 | 11.78 |
| 1165 | ASP | HIE | −0.64 | −5.74 |
| 1165 | ASP | ASN | −0.73 | −0.83 |
| 1165 | ASP | HIP | −1.45 | −6.16 |
| 1165 | ASP | VAL | −0.75 | −5.22 |
| 1165 | ASP | THR | −0.78 | −6.62 |
| 1165 | ASP | HID | −0.73 | −2.07 |
| 1165 | ASP | TRP | −0.68 | −2.53 |
| 1165 | ASP | PHE | −0.67 | −0.93 |
| 1165 | ASP | ALA | −0.76 | −0.76 |
| 1165 | ASP | MET | −0.82 | −4.79 |
| 1165 | ASP | LEU | −0.79 | −4.7 |
| 1165 | ASP | ARG | −1.48 | −3.22 |
| 1165 | ASP | TYR | −0.41 | −1.39 |
| 1165 | ASP | ILE | −0.76 | −5.37 |
| 1165 | ASP | GLN | −0.44 | −4.15 |
| 1165 | ASP | GLY | −0.74 | −2.59 |
| 1165 | ASP | GLU | 0.04 | −3.36 |
| 1165 | ASP | CYS | −0.79 | −3.24 |
| 1165 | ASP | SER | −0.77 | −4.57 |
| 1165 | ASP | LYS | −1.34 | −1.03 |
| 1165 | ASP | PRO | −0.88 | 11.78 |
| 1165 | ASP | HIE | −0.64 | −5.74 |
| 1165 | ASP | ASN | −0.73 | −0.83 |
| 1165 | ASP | HIP | −1.45 | −6.16 |
| 1165 | ASP | VAL | −0.75 | −5.22 |
| 1165 | ASP | THR | −0.78 | −6.62 |
| 1165 | ASP | HID | −0.73 | −2.07 |
| 1165 | ASP | TRP | −0.68 | −2.53 |
| 1165 | ASP | PHE | −0.67 | −0.93 |
| 1165 | ASP | ALA | −0.76 | −0.76 |
| 1165 | ASP | MET | −0.82 | −4.79 |
| 1165 | ASP | LEU | −0.79 | −4.7 |
| 1165 | ASP | ARG | −1.48 | −3.22 |
| 1165 | ASP | TYR | −0.41 | −1.39 |
| 1166 | LEU | ILE | 0.02 | 0.71 |
| 1166 | LEU | GLN | 0.43 | 9.37 |
| 1166 | LEU | GLY | 0 | 19.92 |
| 1166 | LEU | GLU | 2.3 | 16.54 |
| 1166 | LEU | CYS | 0.02 | 14.41 |
| 1166 | LEU | ASP | 1.68 | 20.42 |
| 1166 | LEU | SER | 0.22 | 16.78 |
| 1166 | LEU | LYS | −1.97 | 23.62 |
| 1166 | LEU | PRO | −0.11 | 25.93 |
| 1166 | LEU | HIE | 0.03 | 15.42 |
| 1166 | LEU | ASN | −0.27 | 14.1 |
| 1166 | LEU | HIP | −1.25 | 7.74 |
| 1166 | LEU | VAL | 0.04 | 5.46 |
| 1166 | LEU | THR | 0.17 | 10.98 |
| 1166 | LEU | HID | 0.33 | 9.07 |
| 1166 | LEU | TRP | 0.3 | 5.39 |
| 1166 | LEU | PHE | 0.14 | 5.29 |
| 1166 | LEU | ALA | 0 | 17.28 |
| 1166 | LEU | MET | 0.06 | −7.89 |
| 1166 | LEU | ARG | −0.49 | 7.55 |
| 1166 | LEU | TYR | 0.17 | 5.15 |
| 1166 | LEU | ILE | 0.02 | 0.71 |
| 1166 | LEU | GLN | 0.43 | 9.37 |
| 1166 | LEU | GLY | 0 | 19.92 |
| 1166 | LEU | GLU | 2.3 | 16.54 |
| 1166 | LEU | CYS | 0.02 | 14.41 |

TABLE 1-continued

| Single Amino Acid Mutations in HR2 | | | | |
|---|---|---|---|---|
| R # | WT | MUT | Δ Aff. | Δ Stab. |
| 1166 | LEU | ASP | 1.68 | 20.42 |
| 1166 | LEU | SER | 0.22 | 16.78 |
| 1166 | LEU | LYS | −1.97 | 23.62 |
| 1166 | LEU | PRO | −0.11 | 25.93 |
| 1166 | LEU | HIE | 0.03 | 15.42 |
| 1166 | LEU | ASN | −0.27 | 14.1 |
| 1166 | LEU | HIP | −1.25 | 7.74 |
| 1166 | LEU | VAL | 0.04 | 5.46 |
| 1166 | LEU | THR | 0.17 | 10.98 |
| 1166 | LEU | HID | 0.33 | 9.07 |
| 1166 | LEU | TRP | 0.3 | 5.39 |
| 1166 | LEU | PHE | 0.14 | 5.29 |
| 1166 | LEU | ALA | 0 | 17.28 |
| 1166 | LEU | MET | 0.06 | −7.89 |
| 1166 | LEU | ARG | −0.49 | 7.55 |
| 1166 | LEU | TYR | 0.17 | 5.15 |
| 1167 | GLY | ILE | −1.06 | 6.91 |
| 1167 | GLY | GLN | −0.66 | 3.47 |
| 1167 | GLY | GLU | −0.18 | 4.83 |
| 1167 | GLY | CYS | −0.17 | 5.7 |
| 1167 | GLY | ASP | 0.73 | 7.42 |
| 1167 | GLY | SER | −0.08 | 6.04 |
| 1167 | GLY | LYS | −0.39 | 6.24 |
| 1167 | GLY | PRO | −0.03 | 46.27 |
| 1167 | GLY | HIE | 1.03 | 5.26 |
| 1167 | GLY | ASN | 0.36 | 4.09 |
| 1167 | GLY | HIP | 1.31 | −2.02 |
| 1167 | GLY | VAL | −0.76 | 14.01 |
| 1167 | GLY | THR | −0.84 | 4.03 |
| 1167 | GLY | HID | −0.08 | −1.79 |
| 1167 | GLY | TRP | 0.12 | 3.58 |
| 1167 | GLY | PHE | −4.27 | 2.42 |
| 1167 | GLY | ALA | −0.07 | 3.06 |
| 1167 | GLY | MET | −1.13 | 1.94 |
| 1167 | GLY | LEU | −1.03 | −1.79 |
| 1167 | GLY | ARG | −0.65 | −2.59 |
| 1167 | GLY | TYR | −0.03 | 2.72 |
| 1167 | GLY | ILE | −1.06 | 6.91 |
| 1167 | GLY | GLN | −0.66 | 3.46 |
| 1167 | GLY | GLU | −0.18 | 4.85 |
| 1167 | GLY | CYS | −0.17 | 5.7 |
| 1167 | GLY | ASP | 0.73 | 7.42 |
| 1167 | GLY | SER | −0.08 | 6.04 |
| 1167 | GLY | LYS | −0.39 | 6.24 |
| 1167 | GLY | PRO | −0.03 | 46.27 |
| 1167 | GLY | HIE | 1.03 | 5.26 |
| 1167 | GLY | ASN | 0.36 | 4.09 |
| 1167 | GLY | HIP | 1.31 | −2.01 |
| 1167 | GLY | VAL | −0.76 | 14.01 |
| 1167 | GLY | THR | −0.84 | 4.03 |
| 1167 | GLY | HID | −0.08 | −1.79 |
| 1167 | GLY | TRP | 0.12 | 3.58 |
| 1167 | GLY | PHE | −4.27 | 2.42 |
| 1167 | GLY | ALA | −0.07 | 3.06 |
| 1167 | GLY | MET | −1.13 | 1.94 |
| 1167 | GLY | LEU | −1.03 | −1.79 |
| 1167 | GLY | ARG | −0.65 | −2.56 |
| 1167 | GLY | TYR | −0.03 | 2.72 |
| 1168 | ASP | ILE | −0.68 | −0.71 |
| 1168 | ASP | GLN | −1.89 | −8.18 |
| 1168 | ASP | GLY | −0.43 | 3.32 |
| 1168 | ASP | GLU | 0.17 | −6.06 |
| 1168 | ASP | CYS | −0.68 | 0.56 |
| 1168 | ASP | SER | −0.53 | −0.15 |
| 1168 | ASP | LYS | −0.48 | 4.75 |
| 1168 | ASP | PRO | −0.63 | 2.82 |
| 1168 | ASP | HIE | −0.41 | 2.5 |
| 1168 | ASP | ASN | −0.58 | −5.8 |
| 1168 | ASP | HIP | −0.75 | −1.65 |
| 1168 | ASP | VAL | −0.47 | 0.63 |
| 1168 | ASP | THR | −0.55 | −0.72 |
| 1168 | ASP | HID | −0.4 | 0.47 |
| 1168 | ASP | TRP | −0.26 | 0.29 |
| 1168 | ASP | PHE | 0.05 | 3.8 |
| 1168 | ASP | ALA | −0.47 | 2.09 |
| 1168 | ASP | MET | −0.78 | −7.36 |

TABLE 1-continued

| Single Amino Acid Mutations in HR2 | | | | |
|---|---|---|---|---|
| R # | WT | MUT | Δ Aff. | Δ Stab. |
| 1168 | ASP | LEU | −0.85 | −0.12 |
| 1168 | ASP | ARG | −1.26 | −5.35 |
| 1168 | ASP | TYR | −2.01 | 1.41 |
| 1168 | ASP | ILE | −0.68 | −0.71 |
| 1168 | ASP | GLN | −1.89 | −8.18 |
| 1168 | ASP | GLY | −0.43 | 3.32 |
| 1168 | ASP | GLU | 0.17 | −6.06 |
| 1168 | ASP | CYS | −0.68 | 0.56 |
| 1168 | ASP | SER | −0.53 | −0.15 |
| 1168 | ASP | LYS | −0.48 | 4.75 |
| 1168 | ASP | PRO | −0.63 | 2.82 |
| 1168 | ASP | HIE | −0.41 | 2.5 |
| 1168 | ASP | ASN | −0.58 | −5.8 |
| 1168 | ASP | HIP | −0.75 | −1.65 |
| 1168 | ASP | VAL | −0.47 | 0.63 |
| 1168 | ASP | THR | −0.55 | −0.72 |
| 1168 | ASP | HID | −0.4 | 0.47 |
| 1168 | ASP | TRP | −0.24 | 0.97 |
| 1168 | ASP | PHE | 0.05 | 3.8 |
| 1168 | ASP | ALA | −0.47 | 2.09 |
| 1168 | ASP | MET | −0.78 | −7.36 |
| 1168 | ASP | LEU | −0.85 | −0.12 |
| 1168 | ASP | ARG | −1.26 | −5.35 |
| 1168 | ASP | TYR | −2.06 | 1.41 |
| 1169 | ILE | GLN | 0.2 | 8.82 |
| 1169 | ILE | GLY | 0 | 22.65 |
| 1169 | ILE | GLU | 2.74 | 19.63 |
| 1169 | ILE | CYS | 0.13 | 14.61 |
| 1169 | ILE | ASP | 2.32 | 24.75 |
| 1169 | ILE | SER | 0.1 | 18.59 |
| 1169 | ILE | LYS | −2.24 | 29.09 |
| 1169 | ILE | PRO | −0.11 | 25.54 |
| 1169 | ILE | HIE | −0.18 | 10.88 |
| 1169 | ILE | ASN | 0.12 | 15.84 |
| 1169 | ILE | HIP | −1.83 | 7.55 |
| 1169 | ILE | VAL | −0.01 | 2.67 |
| 1169 | ILE | THR | 0.2 | 11.86 |
| 1169 | ILE | HID | 0.37 | 5.88 |
| 1169 | ILE | TRP | −0.09 | 103.59 |
| 1169 | ILE | PHE | −0.15 | 0.02 |
| 1169 | ILE | ALA | 0.02 | 17.6 |
| 1169 | ILE | MET | −0.02 | −8.6 |
| 1169 | ILE | LEU | −0.09 | −2.84 |
| 1169 | ILE | ARG | −2.47 | 6.88 |
| 1169 | ILE | TYR | −0.17 | 15.35 |
| 1169 | ILE | GLN | 0.2 | 8.82 |
| 1169 | ILE | GLY | 0 | 22.65 |
| 1169 | ILE | GLU | 2.74 | 19.63 |
| 1169 | ILE | CYS | 0.13 | 14.61 |
| 1169 | ILE | ASP | 2.32 | 24.75 |
| 1169 | ILE | SER | 0.1 | 18.59 |
| 1169 | ILE | LYS | −2.24 | 29.09 |
| 1169 | ILE | PRO | −0.11 | 25.54 |
| 1169 | ILE | HIE | −0.18 | 10.88 |
| 1169 | ILE | ASN | 0.12 | 15.84 |
| 1169 | ILE | HIP | −1.83 | 7.55 |
| 1169 | ILE | VAL | −0.01 | 2.67 |
| 1169 | ILE | THR | 0.2 | 11.86 |
| 1169 | ILE | HID | 0.37 | 5.88 |
| 1169 | ILE | TRP | −0.09 | 103.59 |
| 1169 | ILE | PHE | −0.15 | 0.02 |
| 1169 | ILE | ALA | 0.02 | 17.6 |
| 1169 | ILE | MET | −0.02 | −8.6 |
| 1169 | ILE | LEU | −0.09 | −2.84 |
| 1169 | ILE | ARG | −2.47 | 6.88 |
| 1169 | ILE | TYR | −0.17 | 15.35 |
| 1170 | SER | ILE | 0.21 | −0.6 |
| 1170 | SER | GLN | 0.38 | 1.65 |
| 1170 | SER | GLY | −0.02 | 2.5 |
| 1170 | SER | GLU | 3.9 | 5.43 |
| 1170 | SER | CYS | −0.02 | 0.02 |
| 1170 | SER | ASP | 0.86 | 9.19 |
| 1170 | SER | LYS | −0.53 | 1.83 |
| 1170 | SER | PRO | −0.03 | 86.83 |
| 1170 | SER | HIE | 0.65 | 1.71 |
| 1170 | SER | ASN | −0.08 | 0.26 |

TABLE 1-continued

| Single Amino Acid Mutations in HR2 | | | | |
|---|---|---|---|---|
| R # | WT | MUT | Δ Aff. | Δ Stab. |
| 1170 | SER | HIP | −0.71 | −3.29 |
| 1170 | SER | VAL | 0.09 | 0.57 |
| 1170 | SER | THR | −0.02 | 0.27 |
| 1170 | SER | HID | −0.21 | −3.32 |
| 1170 | SER | TRP | 0.3 | 3.53 |
| 1170 | SER | PHE | 0.06 | 2.19 |
| 1170 | SER | ALA | 0.02 | 0.99 |
| 1170 | SER | MET | 0.02 | −3.21 |
| 1170 | SER | LEU | 0.14 | −3.56 |
| 1170 | SER | ARG | −0.65 | −5.84 |
| 1170 | SER | TYR | 0.91 | 2.03 |
| 1170 | SER | ILE | 0.21 | −0.6 |
| 1170 | SER | GLN | 0.38 | 1.65 |
| 1170 | SER | GLY | −0.02 | 2.5 |
| 1170 | SER | GLU | 3.9 | 5.43 |
| 1170 | SER | CYS | −0.02 | 0.02 |
| 1170 | SER | ASP | 0.86 | 9.19 |
| 1170 | SER | LYS | −0.53 | 1.83 |
| 1170 | SER | PRO | −0.03 | 86.83 |
| 1170 | SER | HIE | 0.65 | 1.71 |
| 1170 | SER | ASN | −0.08 | 0.26 |
| 1170 | SER | HIP | −0.71 | −3.29 |
| 1170 | SER | VAL | 0.09 | 0.57 |
| 1170 | SER | THR | −0.02 | 0.27 |
| 1170 | SER | HID | −0.21 | −3.32 |
| 1170 | SER | TRP | 0.3 | 3.53 |
| 1170 | SER | PHE | 0.06 | 2.19 |
| 1170 | SER | ALA | 0.02 | 0.99 |
| 1170 | SER | MET | 0.02 | −3.21 |
| 1170 | SER | LEU | 0.14 | −3.56 |
| 1170 | SER | ARG | −0.65 | −5.86 |
| 1170 | SER | TYR | 0.91 | 2.03 |
| 1171 | GLY | ILE | −0.02 | 1.8 |
| 1171 | GLY | GLN | 0.37 | −1.35 |
| 1171 | GLY | GLU | 0.53 | 3.45 |
| 1171 | GLY | CYS | −0.05 | 1.27 |
| 1171 | GLY | ASP | 0.54 | 9.71 |
| 1171 | GLY | SER | −0.04 | 3.33 |
| 1171 | GLY | LYS | 10.74 | 3.6 |
| 1171 | GLY | PRO | −0.56 | 30.26 |
| 1171 | GLY | HIE | 1.64 | 2.79 |
| 1171 | GLY | ASN | 0.35 | 4.89 |
| 1171 | GLY | HIP | 1.71 | 0.43 |
| 1171 | GLY | VAL | −0.01 | 1.6 |
| 1171 | GLY | THR | −0.04 | −5.02 |
| 1171 | GLY | HID | −0.02 | 0.49 |
| 1171 | GLY | TRP | −2.29 | 7.51 |
| 1171 | GLY | PHE | −0.03 | 5.38 |
| 1171 | GLY | ALA | −0.02 | 2.78 |
| 1171 | GLY | MET | 0.12 | −0.07 |
| 1171 | GLY | LEU | −0.02 | 1.68 |
| 1171 | GLY | ARG | −0.65 | −5.55 |
| 1171 | GLY | TYR | −0.96 | 5.77 |
| 1171 | GLY | ILE | −0.02 | 1.8 |
| 1171 | GLY | GLN | 0.37 | −1.35 |
| 1171 | GLY | GLU | 0.52 | 3.49 |
| 1171 | GLY | CYS | −0.05 | 1.27 |
| 1171 | GLY | ASP | 0.54 | 9.71 |
| 1171 | GLY | SER | −0.04 | 3.33 |
| 1171 | GLY | LYS | 10.75 | 3.6 |
| 1171 | GLY | PRO | −0.56 | 30.26 |
| 1171 | GLY | HIE | 1.64 | 2.8 |
| 1171 | GLY | ASN | 0.35 | 4.89 |
| 1171 | GLY | HIP | 1.7 | 0.37 |
| 1171 | GLY | VAL | −0.01 | 1.6 |
| 1171 | GLY | THR | −0.04 | −5.02 |
| 1171 | GLY | HID | −0.02 | 0.49 |
| 1171 | GLY | TRP | −2.33 | 7.56 |
| 1171 | GLY | PHE | −0.02 | 5.4 |
| 1171 | GLY | ALA | −0.02 | 2.78 |
| 1171 | GLY | MET | 0.12 | −0.06 |
| 1171 | GLY | LEU | −0.03 | 1.68 |
| 1171 | GLY | ARG | −0.65 | −5.53 |
| 1171 | GLY | TYR | −0.96 | 5.77 |
| 1171 | GLY | ILE | −0.02 | 1.8 |
| 1171 | GLY | GLN | 0.37 | −1.35 |

TABLE 1-continued

| Single Amino Acid Mutations in HR2 | | | | |
|---|---|---|---|---|
| R # | WT | MUT | Δ Aff. | Δ Stab. |
| 1171 | GLY | GLU | 0.52 | 3.49 |
| 1171 | GLY | CYS | −0.05 | 1.27 |
| 1171 | GLY | ASP | 0.54 | 9.71 |
| 1171 | GLY | SER | −0.04 | 3.33 |
| 1171 | GLY | LYS | 10.75 | 3.6 |
| 1171 | GLY | PRO | −0.56 | 30.26 |
| 1171 | GLY | HIE | 1.64 | 2.8 |
| 1171 | GLY | ASN | 0.35 | 4.89 |
| 1171 | GLY | HIP | 1.7 | 0.37 |
| 1171 | GLY | VAL | −0.01 | 1.6 |
| 1171 | GLY | THR | −0.04 | −5.02 |
| 1171 | GLY | HID | −0.02 | 0.49 |
| 1171 | GLY | TRP | −2.35 | 7.56 |
| 1171 | GLY | PHE | −0.02 | 5.4 |
| 1171 | GLY | ALA | −0.02 | 2.78 |
| 1171 | GLY | MET | 0.12 | −0.06 |
| 1171 | GLY | LEU | −0.02 | 1.68 |
| 1171 | GLY | ARG | −0.65 | −5.47 |
| 1171 | GLY | TYR | −0.96 | 5.77 |
| 1172 | ILE | GLN | −0.14 | 7.07 |
| 1172 | ILE | GLY | −0.18 | 20.21 |
| 1172 | ILE | GLU | 0.76 | 10.38 |
| 1172 | ILE | CYS | −0.04 | 14.19 |
| 1172 | ILE | ASP | 1.14 | 23.26 |
| 1172 | ILE | SER | −0.12 | 18.65 |
| 1172 | ILE | LYS | −0.84 | 20.64 |
| 1172 | ILE | PRO | −0.04 | 42.28 |
| 1172 | ILE | HIE | 0 | 7.2 |
| 1172 | ILE | ASN | −0.36 | 14.28 |
| 1172 | ILE | HIP | −0.99 | 5.54 |
| 1172 | ILE | VAL | 0 | 5.18 |
| 1172 | ILE | THR | 0.1 | 9.41 |
| 1172 | ILE | HID | 0.3 | 11.9 |
| 1172 | ILE | TRP | 0.07 | 5.39 |
| 1172 | ILE | PHE | −0.09 | 9.7 |
| 1172 | ILE | ALA | −0.12 | 15.81 |
| 1172 | ILE | MET | 0.42 | −4.21 |
| 1172 | ILE | LEU | −0.03 | 4.13 |
| 1172 | ILE | ARG | −1.05 | 2.62 |
| 1172 | ILE | TYR | −0.18 | 10.32 |
| 1172 | ILE | GLN | −0.14 | 7.07 |
| 1172 | ILE | GLY | −0.18 | 20.21 |
| 1172 | ILE | GLU | 0.76 | 10.38 |
| 1172 | ILE | CYS | −0.04 | 14.19 |
| 1172 | ILE | ASP | 1.14 | 23.26 |
| 1172 | ILE | SER | −0.12 | 18.65 |
| 1172 | ILE | LYS | −0.84 | 20.64 |
| 1172 | ILE | PRO | −0.04 | 42.28 |
| 1172 | ILE | HIE | 0 | 7.2 |
| 1172 | ILE | ASN | −0.36 | 14.28 |
| 1172 | ILE | HIP | −0.99 | 5.54 |
| 1172 | ILE | VAL | 0 | 5.18 |
| 1172 | ILE | THR | 0.1 | 9.41 |
| 1172 | ILE | HID | 0.3 | 11.9 |
| 1172 | ILE | TRP | 0.07 | 5.39 |
| 1172 | ILE | PHE | −0.09 | 9.7 |
| 1172 | ILE | ALA | −0.12 | 15.81 |
| 1172 | ILE | MET | 0.42 | −4.21 |
| 1172 | ILE | LEU | −0.03 | 4.13 |
| 1172 | ILE | ARG | −1.05 | 2.62 |
| 1172 | ILE | TYR | −0.18 | 10.32 |
| 1173 | ASN | ILE | 0 | −4.92 |
| 1173 | ASN | GLN | 0.01 | −5.55 |
| 1173 | ASN | GLY | −0.05 | −3.06 |
| 1173 | ASN | GLU | 0.88 | −0.26 |
| 1173 | ASN | CYS | −0.13 | −4.72 |
| 1173 | ASN | ASP | 0.72 | 0.24 |
| 1173 | ASN | SER | −0.12 | −2.74 |
| 1173 | ASN | LYS | −0.58 | −3.68 |
| 1173 | ASN | PRO | −0.08 | 15.96 |
| 1173 | ASN | HIE | 0.17 | −3.87 |
| 1173 | ASN | HIP | −1.09 | −8.64 |
| 1173 | ASN | VAL | −0.07 | −3.8 |
| 1173 | ASN | THR | −0.11 | −3.65 |
| 1173 | ASN | HID | 0.04 | −7.6 |
| 1173 | ASN | TRP | 0.36 | −6.38 |

TABLE 1-continued

Single Amino Acid Mutations in HR2

| R # | WT | MUT | Δ Aff. | Δ Stab. |
|---|---|---|---|---|
| 1173 | ASN | PHE | 0.39 | −6.17 |
| 1173 | ASN | ALA | −0.08 | −3.06 |
| 1173 | ASN | MET | −0.08 | −8.04 |
| 1173 | ASN | LEU | 0.06 | −6.34 |
| 1173 | ASN | ARG | −0.79 | −12.67 |
| 1173 | ASN | TYR | 0.61 | −6.77 |
| 1173 | ASN | ILE | 0 | −4.92 |
| 1173 | ASN | GLN | 0.01 | −5.55 |
| 1173 | ASN | GLY | −0.05 | −3.06 |
| 1173 | ASN | GLU | 0.88 | −0.26 |
| 1173 | ASN | CYS | −0.13 | −4.72 |
| 1173 | ASN | ASP | 0.72 | 0.24 |
| 1173 | ASN | SER | −0.12 | −2.74 |
| 1173 | ASN | LYS | −0.58 | −3.68 |
| 1173 | ASN | PRO | −0.08 | 15.96 |
| 1173 | ASN | HIE | 0.17 | −3.87 |
| 1173 | ASN | HIP | −1.09 | −8.64 |
| 1173 | ASN | VAL | −0.07 | −3.8 |
| 1173 | ASN | THR | −0.11 | −3.65 |
| 1173 | ASN | HID | 0.04 | −7.6 |
| 1173 | ASN | TRP | 0.36 | −6.38 |
| 1173 | ASN | PHE | 0.39 | −6.17 |
| 1173 | ASN | ALA | −0.08 | −3.06 |
| 1173 | ASN | MET | −0.08 | −8.04 |
| 1173 | ASN | LEU | 0.06 | −6.34 |
| 1173 | ASN | ARG | −0.79 | −12.67 |
| 1173 | ASN | TYR | 0.61 | −6.77 |
| 1174 | ALA | ILE | 0.03 | 1.77 |
| 1174 | ALA | GLN | 0.6 | 14.37 |
| 1174 | ALA | GLY | −0.06 | 7.02 |
| 1174 | ALA | GLU | 14.4 | 20.32 |
| 1174 | ALA | CYS | −0.1 | 7.58 |
| 1174 | ALA | ASP | 2.58 | 30.89 |
| 1174 | ALA | SER | 0.25 | 3.57 |
| 1174 | ALA | LYS | −1.42 | 44.97 |
| 1174 | ALA | PRO | 0.03 | 24.59 |
| 1174 | ALA | HIE | 1.01 | 98.29 |
| 1174 | ALA | ASN | −13.68 | 32.46 |
| 1174 | ALA | HIP | −1.42 | 95.28 |
| 1174 | ALA | VAL | −0.18 | 22.44 |
| 1174 | ALA | THR | −0.9 | 14.58 |
| 1174 | ALA | HID | 1.13 | 95.86 |
| 1174 | ALA | TRP | −0.55 | 57.47 |
| 1174 | ALA | PHE | 0.27 | 68.41 |
| 1174 | ALA | MET | −2.6 | 17.32 |
| 1174 | ALA | LEU | −0.85 | 31.41 |
| 1174 | ALA | ARG | −2.47 | 13.19 |
| 1174 | ALA | TYR | 0.04 | 72.77 |
| 1174 | ALA | ILE | 0.03 | 1.77 |
| 1174 | ALA | GLN | 0.6 | 14.37 |
| 1174 | ALA | GLY | −0.06 | 7.02 |
| 1174 | ALA | GLU | 14.4 | 20.32 |
| 1174 | ALA | CYS | −0.1 | 7.58 |
| 1174 | ALA | ASP | 2.58 | 30.89 |
| 1174 | ALA | SER | 0.25 | 3.57 |
| 1174 | ALA | LYS | −1.42 | 44.97 |
| 1174 | ALA | PRO | 0.03 | 24.59 |
| 1174 | ALA | HIE | 1.01 | 98.29 |
| 1174 | ALA | ASN | −13.68 | 32.46 |
| 1174 | ALA | HIP | −1.42 | 95.28 |
| 1174 | ALA | VAL | −0.18 | 22.44 |
| 1174 | ALA | THR | −0.9 | 14.58 |
| 1174 | ALA | HID | 1.13 | 95.86 |
| 1174 | ALA | TRP | −0.55 | 57.47 |
| 1174 | ALA | PHE | 0.27 | 68.41 |
| 1174 | ALA | MET | −2.6 | 17.32 |
| 1174 | ALA | LEU | −0.85 | 31.41 |
| 1174 | ALA | ARG | −2.47 | 13.19 |
| 1174 | ALA | TYR | 0.04 | 72.77 |
| 1174 | ALA | ILE | 0.03 | 1.77 |
| 1174 | ALA | GLN | 0.6 | 14.37 |
| 1174 | ALA | GLY | −0.06 | 7.02 |
| 1174 | ALA | GLU | 14.4 | 20.32 |
| 1174 | ALA | CYS | −0.1 | 7.58 |
| 1174 | ALA | ASP | 2.58 | 30.89 |
| 1174 | ALA | SER | 0.25 | 3.57 |

TABLE 1-continued

Single Amino Acid Mutations in HR2

| R # | WT | MUT | Δ Aff. | Δ Stab. |
|---|---|---|---|---|
| 1174 | ALA | LYS | −1.42 | 44.97 |
| 1174 | ALA | PRO | 0.03 | 24.59 |
| 1174 | ALA | HIE | 1.01 | 98.29 |
| 1174 | ALA | ASN | −13.68 | 32.46 |
| 1174 | ALA | HIP | −1.42 | 95.28 |
| 1174 | ALA | VAL | −0.18 | 22.44 |
| 1174 | ALA | THR | −0.9 | 14.58 |
| 1174 | ALA | HID | 1.13 | 95.86 |
| 1174 | ALA | TRP | −0.55 | 57.47 |
| 1174 | ALA | PHE | 0.27 | 68.41 |
| 1174 | ALA | MET | −2.6 | 17.32 |
| 1174 | ALA | LEU | −0.85 | 31.41 |
| 1174 | ALA | ARG | −2.47 | 13.19 |
| 1174 | ALA | TYR | 0.04 | 72.77 |
| 1174 | ALA | ILE | 0.03 | 1.77 |
| 1174 | ALA | GLN | 0.6 | 14.37 |
| 1174 | ALA | GLY | −0.06 | 7.02 |
| 1174 | ALA | GLU | 14.4 | 20.32 |
| 1174 | ALA | CYS | −0.1 | 7.58 |
| 1174 | ALA | ASP | 2.58 | 30.89 |
| 1174 | ALA | SER | 0.25 | 3.57 |
| 1174 | ALA | LYS | −1.42 | 44.97 |
| 1174 | ALA | PRO | 0.03 | 24.59 |
| 1174 | ALA | HIE | 1.01 | 98.29 |
| 1174 | ALA | ASN | −13.68 | 32.46 |
| 1174 | ALA | HIP | −1.42 | 95.28 |
| 1174 | ALA | VAL | −0.18 | 22.44 |
| 1174 | ALA | THR | −0.9 | 14.58 |
| 1174 | ALA | HID | 1.13 | 95.86 |
| 1174 | ALA | TRP | −0.55 | 57.47 |
| 1174 | ALA | PHE | 0.27 | 68.41 |
| 1174 | ALA | MET | −2.6 | 17.32 |
| 1174 | ALA | LEU | −0.85 | 31.41 |
| 1174 | ALA | ARG | −2.47 | 13.19 |
| 1174 | ALA | TYR | 0.04 | 72.77 |
| 1175 | SER | ILE | −1.05 | −6.26 |
| 1175 | SER | GLN | 0.46 | −9.07 |
| 1175 | SER | GLY | 0.06 | 3.57 |
| 1175 | SER | GLU | 1.47 | −2.37 |
| 1175 | SER | CYS | −0.04 | −1.18 |
| 1175 | SER | ASP | 0.75 | 11.05 |
| 1175 | SER | LYS | −0.04 | 2.21 |
| 1175 | SER | PRO | −0.86 | 13.52 |
| 1175 | SER | HIE | 0.22 | −1.26 |
| 1175 | SER | ASN | 0.01 | −2.11 |
| 1175 | SER | HIP | −0.16 | −10.84 |
| 1175 | SER | VAL | 0.18 | −3.92 |
| 1175 | SER | THR | 0.01 | −0.96 |
| 1175 | SER | HID | −0.02 | −5.35 |
| 1175 | SER | TRP | 0.46 | −0.76 |
| 1175 | SER | PHE | 0.1 | −1.46 |
| 1175 | SER | ALA | 0.09 | 0.29 |
| 1175 | SER | MET | −0.19 | −6.87 |
| 1175 | SER | LEU | −0.32 | −1.02 |
| 1175 | SER | ARG | −0.32 | −15.18 |
| 1175 | SER | TYR | 0.5 | −1.54 |
| 1175 | SER | ILE | −1.05 | −6.26 |
| 1175 | SER | GLN | 0.46 | −9.07 |
| 1175 | SER | GLY | 0.06 | 3.57 |
| 1175 | SER | GLU | 1.47 | −2.37 |
| 1175 | SER | CYS | −0.04 | −1.18 |
| 1175 | SER | ASP | 0.75 | 11.05 |
| 1175 | SER | LYS | −0.04 | 2.21 |
| 1175 | SER | PRO | −0.86 | 13.52 |
| 1175 | SER | HIE | 0.22 | −1.26 |
| 1175 | SER | ASN | 0.01 | −2.11 |
| 1175 | SER | HIP | −0.16 | −10.84 |
| 1175 | SER | VAL | 0.18 | −3.92 |
| 1175 | SER | THR | 0.01 | −0.96 |
| 1175 | SER | HID | −0.02 | −5.35 |
| 1175 | SER | TRP | 0.46 | −0.76 |
| 1175 | SER | PHE | 0.1 | −1.46 |
| 1175 | SER | ALA | 0.09 | 0.29 |
| 1175 | SER | MET | −0.19 | −6.87 |
| 1175 | SER | LEU | −0.32 | −1.02 |
| 1175 | SER | ARG | −0.32 | −15.18 |

TABLE 1-continued

Single Amino Acid Mutations in HR2

| R # | WT | MUT | Δ Aff. | Δ Stab. |
|---|---|---|---|---|
| 1175 | SER | TYR | 0.5 | −1.54 |
| 1176 | VAL | ILE | 0.03 | −1.02 |
| 1176 | VAL | GLN | −0.17 | −7.89 |
| 1176 | VAL | GLY | −0.07 | 5.89 |
| 1176 | VAL | GLU | 0.74 | 3.01 |
| 1176 | VAL | CYS | −0.16 | 2.27 |
| 1176 | VAL | ASP | 0.65 | 8.46 |
| 1176 | VAL | SER | −0.13 | 4.31 |
| 1176 | VAL | LYS | −0.3 | 6.12 |
| 1176 | VAL | PRO | −0.2 | 3.95 |
| 1176 | VAL | HIE | 0.09 | 2.65 |
| 1176 | VAL | ASN | −0.16 | −1.31 |
| 1176 | VAL | HIP | 0.59 | −3.47 |
| 1176 | VAL | THR | −0.16 | −2.68 |
| 1176 | VAL | HID | 0.21 | −2.44 |
| 1176 | VAL | TRP | 0.36 | −2.36 |
| 1176 | VAL | PHE | 0.02 | −5.16 |
| 1176 | VAL | ALA | −0.05 | 4.25 |
| 1176 | VAL | MET | 0.25 | −7.02 |
| 1176 | VAL | LEU | 0.06 | −4.5 |
| 1176 | VAL | ARG | 2.25 | −8.16 |
| 1176 | VAL | TYR | −0.02 | −9.81 |
| 1177 | VAL | ILE | −0.01 | −7.9 |
| 1177 | VAL | GLN | −0.83 | 10.65 |
| 1177 | VAL | GLY | −0.08 | 20.16 |
| 1177 | VAL | GLU | 1.59 | 17.13 |
| 1177 | VAL | CYS | 0.11 | 8.66 |
| 1177 | VAL | ASP | 2.03 | 26.85 |
| 1177 | VAL | SER | −0.15 | 16.76 |
| 1177 | VAL | LYS | −0.81 | 80.26 |
| 1177 | VAL | PRO | −0.02 | 40.8 |
| 1177 | VAL | HIE | −0.06 | 29.21 |
| 1177 | VAL | ASN | −0.46 | 13.55 |
| 1177 | VAL | HIP | −1.78 | 30.06 |
| 1177 | VAL | THR | −0.13 | 10.58 |
| 1177 | VAL | HID | 0.06 | 30.17 |
| 1177 | VAL | TRP | 0.25 | 1253.69 |
| 1177 | VAL | PHE | −0.02 | 60.84 |
| 1177 | VAL | ALA | −0.06 | 11.87 |
| 1177 | VAL | MET | 0.1 | 35.52 |
| 1177 | VAL | LEU | −0.1 | 3.56 |
| 1177 | VAL | ARG | −1.97 | 34.38 |
| 1177 | VAL | TYR | 0.09 | 131.02 |
| 1178 | ASN | ILE | 0.06 | −11.1 |
| 1178 | ASN | GLN | −3.33 | −6.19 |
| 1178 | ASN | GLY | 0 | −1.67 |
| 1178 | ASN | GLU | 0.31 | −10.28 |
| 1178 | ASN | CYS | −0.06 | −4.23 |
| 1178 | ASN | ASP | 0.51 | 4.63 |
| 1178 | ASN | SER | −0.03 | 1.09 |
| 1178 | ASN | LYS | 0.88 | −1.69 |
| 1178 | ASN | PRO | −0.17 | 11.73 |
| 1178 | ASN | HIE | −0.04 | −2.65 |
| 1178 | ASN | HIP | −0.17 | −8.22 |
| 1178 | ASN | VAL | 0.05 | −6.27 |
| 1178 | ASN | THR | 0.03 | −5.31 |
| 1178 | ASN | HID | 0.06 | −7.04 |
| 1178 | ASN | TRP | −0.02 | −9.51 |
| 1178 | ASN | PHE | 0.08 | −5.55 |
| 1178 | ASN | ALA | −0.01 | −3.08 |
| 1178 | ASN | MET | −0.25 | −6.09 |
| 1178 | ASN | LEU | 0.11 | −8.13 |
| 1178 | ASN | ARG | −0.24 | −13.48 |
| 1178 | ASN | TYR | 1.1 | −5.58 |
| 1179 | ILE | GLN | −0.14 | 12.9 |
| 1179 | ILE | GLY | −0.22 | 31.18 |
| 1179 | ILE | GLU | 2.55 | 29.78 |
| 1179 | ILE | CYS | 0.06 | 19.32 |
| 1179 | ILE | ASP | 1.72 | 34.64 |
| 1179 | ILE | SER | −0.03 | 24 |
| 1179 | ILE | LYS | −1.76 | 42.49 |
| 1179 | ILE | PRO | −0.05 | 57.98 |
| 1179 | ILE | HIE | −0.12 | 17.6 |
| 1179 | ILE | ASN | 0.39 | 22.14 |
| 1179 | ILE | HIP | −1.3 | 13.33 |
| 1179 | ILE | VAL | −0.09 | 8.61 |

TABLE 1-continued

Single Amino Acid Mutations in HR2

| R # | WT | MUT | Δ Aff. | Δ Stab. |
|---|---|---|---|---|
| 1179 | ILE | THR | 0.1 | 16.64 |
| 1179 | ILE | HID | 0.69 | 17.98 |
| 1179 | ILE | TRP | 0.28 | 206.13 |
| 1179 | ILE | PHE | −0.02 | 111.62 |
| 1179 | ILE | ALA | −0.13 | 23.73 |
| 1179 | ILE | MET | 0.18 | −1.07 |
| 1179 | ILE | LEU | 0.12 | −1.18 |
| 1179 | ILE | ARG | −2.2 | 42.65 |
| 1179 | ILE | TYR | 0.03 | 121.99 |
| 1180 | GLN | ILE | −0.09 | −1.67 |
| 1180 | GLN | GLY | −0.07 | 5.4 |
| 1180 | GLN | GLU | 0.32 | 3.56 |
| 1180 | GLN | CYS | −0.12 | 2.01 |
| 1180 | GLN | ASP | 0.36 | 7.27 |
| 1180 | GLN | SER | −0.12 | 4.09 |
| 1180 | GLN | LYS | −0.33 | 4.05 |
| 1180 | GLN | PRO | −0.25 | 24.75 |
| 1180 | GLN | HIE | 0.07 | 2.98 |
| 1180 | GLN | ASN | −0.01 | 1.48 |
| 1180 | GLN | HIP | −0.32 | −2.08 |
| 1180 | GLN | VAL | −0.09 | 1.4 |
| 1180 | GLN | THR | −0.12 | 1.19 |
| 1180 | GLN | HID | −0.13 | −0.73 |
| 1180 | GLN | TRP | 0.06 | 0.42 |
| 1180 | GLN | PHE | 0.04 | 1.05 |
| 1180 | GLN | ALA | −0.11 | 4.78 |
| 1180 | GLN | MET | −0.06 | −1.12 |
| 1180 | GLN | LEU | −0.08 | −1.55 |
| 1180 | GLN | ARG | 2.51 | −3.93 |
| 1180 | GLN | TYR | 0.1 | 1.4 |
| 1181 | LYS | ILE | 0.02 | −15.06 |
| 1181 | LYS | GLN | 0.08 | −10.85 |
| 1181 | LYS | GLY | 0.09 | −2.53 |
| 1181 | LYS | GLU | 0.37 | −7.02 |
| 1181 | LYS | CYS | 0.08 | −3.3 |
| 1181 | LYS | ASP | 0.31 | −1.87 |
| 1181 | LYS | SER | 0.09 | −2.18 |
| 1181 | LYS | PRO | 0.01 | 6.45 |
| 1181 | LYS | HIE | 0.14 | −5.12 |
| 1181 | LYS | ASN | 0.1 | −2.2 |
| 1181 | LYS | HIP | −0.09 | −5.61 |
| 1181 | LYS | VAL | 0.07 | −12.85 |
| 1181 | LYS | THR | 0.08 | −6.42 |
| 1181 | LYS | HID | 0.13 | −7.06 |
| 1181 | LYS | TRP | 0.15 | −9.89 |
| 1181 | LYS | PHE | 0.16 | −7.87 |
| 1181 | LYS | ALA | 0.08 | −4.1 |
| 1181 | LYS | MET | 0.13 | −10.8 |
| 1181 | LYS | LEU | 0.09 | −10.23 |
| 1181 | LYS | ARG | −0.1 | −19.03 |
| 1181 | LYS | TYR | 0.16 | −5.84 |
| 1182 | GLU | ILE | −0.72 | 3.6 |
| 1182 | GLU | GLN | −0.27 | 3.96 |
| 1182 | GLU | GLY | −0.3 | 22.22 |
| 1182 | GLU | CYS | −0.39 | 13.55 |
| 1182 | GLU | ASP | 0.09 | 10.82 |
| 1182 | GLU | SER | −0.35 | 15.86 |
| 1182 | GLU | LYS | −0.15 | 23.9 |
| 1182 | GLU | PRO | −0.36 | 22.59 |
| 1182 | GLU | HIE | −0.28 | 6.2 |
| 1182 | GLU | ASN | −0.29 | 10.38 |
| 1182 | GLU | HIP | −0.65 | 15.96 |
| 1182 | GLU | VAL | −0.19 | 7.02 |
| 1182 | GLU | THR | −0.32 | 11.57 |
| 1182 | GLU | HID | −0.39 | 3.49 |
| 1182 | GLU | TRP | −0.38 | 14.07 |
| 1182 | GLU | PHE | −0.52 | 19.79 |
| 1182 | GLU | ALA | −0.29 | 15.93 |
| 1182 | GLU | MET | −0.35 | 2.67 |
| 1182 | GLU | LEU | 0.92 | 4.01 |
| 1182 | GLU | ARG | 5.98 | 5.91 |
| 1182 | GLU | TYR | −0.56 | 17.65 |
| 1183 | ILE | GLN | −0.04 | 11.29 |
| 1183 | ILE | GLY | −0.09 | 19.38 |
| 1183 | ILE | GLU | 0.64 | 15.44 |
| 1183 | ILE | CYS | 0.08 | 14.46 |

TABLE 1-continued

Single Amino Acid Mutations in HR2

| R # | WT | MUT | Δ Aff. | Δ Stab. |
|---|---|---|---|---|
| 1183 | ILE | ASP | 1.22 | 23.01 |
| 1183 | ILE | SER | 0.01 | 12.94 |
| 1183 | ILE | LYS | −0.19 | 17.23 |
| 1183 | ILE | PRO | −0.17 | 51.45 |
| 1183 | ILE | HIE | 0.36 | 12.84 |
| 1183 | ILE | ASN | 0.36 | 13.97 |
| 1183 | ILE | HIP | −0.4 | 13.77 |
| 1183 | ILE | VAL | −0.09 | 7.44 |
| 1183 | ILE | THR | −0.03 | 11.04 |
| 1183 | ILE | HID | −0.06 | 11.78 |
| 1183 | ILE | TRP | 0.21 | 5.41 |
| 1183 | ILE | PHE | 0.01 | 9.39 |
| 1183 | ILE | ALA | −0.13 | 17.25 |
| 1183 | ILE | MET | 0 | 3.39 |
| 1183 | ILE | LEU | −0.04 | 7.9 |
| 1183 | ILE | ARG | −0.41 | 4.75 |
| 1183 | ILE | TYR | 0.04 | 9.85 |
| 1184 | ASP | ILE | −0.23 | −13 |
| 1184 | ASP | GLN | 0.07 | −13.27 |
| 1184 | ASP | GLY | −0.21 | −2.69 |
| 1184 | ASP | GLU | −0.11 | −5.91 |
| 1184 | ASP | CYS | −0.27 | −6.29 |
| 1184 | ASP | SER | −0.25 | −9.91 |
| 1184 | ASP | LYS | −0.31 | −7.83 |
| 1184 | ASP | PRO | −0.25 | 51.91 |
| 1184 | ASP | HIE | −0.28 | −9.07 |
| 1184 | ASP | ASN | −0.26 | −6.04 |
| 1184 | ASP | HIP | −0.46 | −16.92 |
| 1184 | ASP | VAL | −0.26 | −9.94 |
| 1184 | ASP | THR | −0.29 | −9.43 |
| 1184 | ASP | HID | −0.67 | −7.32 |
| 1184 | ASP | TRP | −3.46 | −4.49 |
| 1184 | ASP | PHE | −1.08 | −2.24 |
| 1184 | ASP | ALA | −0.25 | −5.83 |
| 1184 | ASP | MET | −2.04 | −14.02 |
| 1184 | ASP | LEU | −0.27 | −13.9 |
| 1184 | ASP | ARG | −0.35 | −20.06 |
| 1184 | ASP | TYR | −0.28 | −4.13 |
| 1185 | ARG | ILE | 0.25 | 6.51 |
| 1185 | ARG | GLN | 0.25 | 7.37 |
| 1185 | ARG | GLY | 0.2 | 18.3 |
| 1185 | ARG | GLU | 0.51 | 11.47 |
| 1185 | ARG | CYS | 0.2 | 16.6 |
| 1185 | ARG | ASP | 0.57 | 23.42 |
| 1185 | ARG | SER | 0.11 | 14.58 |
| 1185 | ARG | LYS | 0.01 | 12.75 |
| 1185 | ARG | PRO | 0.27 | 89.61 |
| 1185 | ARG | HIE | 0.3 | 11.33 |
| 1185 | ARG | ASN | 0.39 | 20.19 |
| 1185 | ARG | HIP | 0 | 3.61 |
| 1185 | ARG | VAL | 0.24 | 13.19 |
| 1185 | ARG | THR | 0.08 | 12.44 |
| 1185 | ARG | HID | 0.22 | 13.17 |
| 1185 | ARG | TRP | 0.51 | 10.73 |
| 1185 | ARG | PHE | 0.41 | 10.73 |
| 1185 | ARG | ALA | 0.2 | 15.96 |
| 1185 | ARG | MET | 0.23 | 4.64 |
| 1185 | ARG | LEU | 0.38 | 6.49 |
| 1185 | ARG | TYR | 0.34 | 9.47 |
| 1186 | LEU | ILE | 0.11 | 20.73 |
| 1186 | LEU | GLN | 0.08 | 15.32 |
| 1186 | LEU | GLY | −0.21 | 31.18 |
| 1186 | LEU | GLU | 1.43 | 21.45 |
| 1186 | LEU | CYS | −0.13 | 21.6 |
| 1186 | LEU | ASP | 1.14 | 29.6 |
| 1186 | LEU | SER | −0.18 | 22.98 |
| 1186 | LEU | LYS | −1.23 | 35.81 |
| 1186 | LEU | PRO | −0.08 | 70.68 |
| 1186 | LEU | HIE | 0.1 | 15.43 |
| 1186 | LEU | ASN | 0.21 | 21.51 |
| 1186 | LEU | HIP | −0.94 | 11.73 |
| 1186 | LEU | VAL | −0.17 | 18.2 |
| 1186 | LEU | THR | −0.21 | 17.91 |
| 1186 | LEU | HID | 0.48 | 15.76 |
| 1186 | LEU | TRP | 0.53 | 68.2 |
| 1186 | LEU | PHE | 0.27 | 13.47 |

TABLE 1-continued

Single Amino Acid Mutations in HR2

| R # | WT | MUT | Δ Aff. | Δ Stab. |
|---|---|---|---|---|
| 1186 | LEU | ALA | −0.2 | 23.51 |
| 1186 | LEU | MET | −0.32 | 1.54 |
| 1186 | LEU | ARG | −3.87 | 16.81 |
| 1186 | LEU | TYR | 0.86 | 24.32 |
| 1187 | ASN | ILE | −0.15 | −4.61 |
| 1187 | ASN | GLN | 0.41 | −6.76 |
| 1187 | ASN | GLY | 0.03 | 4.78 |
| 1187 | ASN | GLU | 0.22 | −3.98 |
| 1187 | ASN | CYS | 0 | −0.39 |
| 1187 | ASN | ASP | 0.39 | 3.5 |
| 1187 | ASN | SER | −0.05 | −0.44 |
| 1187 | ASN | LYS | 1 | 4.91 |
| 1187 | ASN | PRO | −0.03 | 39.08 |
| 1187 | ASN | HIE | 0.14 | −5.31 |
| 1187 | ASN | HIP | 0.02 | −5.3 |
| 1187 | ASN | VAL | −0.1 | −1.26 |
| 1187 | ASN | THR | −0.14 | −5.41 |
| 1187 | ASN | HID | 0 | −2.38 |
| 1187 | ASN | TRP | 0.11 | −2.94 |
| 1187 | ASN | PHE | 0.01 | −12.18 |
| 1187 | ASN | ALA | −0.02 | 0.27 |
| 1187 | ASN | MET | −0.01 | −8.9 |
| 1187 | ASN | LEU | −0.03 | −10.2 |
| 1187 | ASN | ARG | 4.71 | −6.84 |
| 1187 | ASN | TYR | −0.1 | −12.12 |
| 1188 | GLU | ILE | −0.05 | 2.46 |
| 1188 | GLU | GLN | −0.1 | −1.94 |
| 1188 | GLU | GLY | −0.06 | 7.98 |
| 1188 | GLU | CYS | −0.12 | 3.57 |
| 1188 | GLU | ASP | 0.11 | 11.19 |
| 1188 | GLU | SER | −0.11 | 8.18 |
| 1188 | GLU | LYS | −0.44 | 7.9 |
| 1188 | GLU | PRO | −0.07 | 57.44 |
| 1188 | GLU | HIE | −0.12 | 3.3 |
| 1188 | GLU | ASN | −0.08 | 5.95 |
| 1188 | GLU | HIP | −0.18 | 2.89 |
| 1188 | GLU | VAL | −0.05 | 3.56 |
| 1188 | GLU | THR | −0.12 | 3.54 |
| 1188 | GLU | HID | −0.1 | 2.4 |
| 1188 | GLU | TRP | −1.23 | 0.06 |
| 1188 | GLU | PHE | −0.1 | 1.87 |
| 1188 | GLU | ALA | −0.09 | 4.32 |
| 1188 | GLU | MET | −0.12 | −3.78 |
| 1188 | GLU | LEU | −0.12 | −1.07 |
| 1188 | GLU | ARG | −0.18 | −8.12 |
| 1188 | GLU | TYR | −0.09 | 2.69 |
| 1189 | VAL | ILE | −0.01 | −8.72 |
| 1189 | VAL | GLN | 0.22 | −2.52 |
| 1189 | VAL | GLY | −0.22 | 16.73 |
| 1189 | VAL | GLU | 0.57 | 4.13 |
| 1189 | VAL | CYS | −0.07 | 7.75 |
| 1189 | VAL | ASP | 0.51 | 12.23 |
| 1189 | VAL | SER | −0.36 | 8.08 |
| 1189 | VAL | LYS | −0.48 | 13.8 |
| 1189 | VAL | PRO | −0.04 | 56.5 |
| 1189 | VAL | HIE | −0.1 | 5.02 |
| 1189 | VAL | ASN | −0.42 | 8.63 |
| 1189 | VAL | HIP | −0.81 | 0.81 |
| 1189 | VAL | THR | −0.31 | 2.98 |
| 1189 | VAL | HID | −0.02 | 4.74 |
| 1189 | VAL | TRP | −0.05 | 9.14 |
| 1189 | VAL | PHE | −0.06 | 6.41 |
| 1189 | VAL | ALA | −0.23 | 7.78 |
| 1189 | VAL | MET | −0.09 | −1.99 |
| 1189 | VAL | LEU | −0.08 | −9.57 |
| 1189 | VAL | ARG | 0.9 | −0.93 |
| 1189 | VAL | TYR | 0.45 | 101.85 |
| 1190 | ALA | ILE | 0.04 | 33.19 |
| 1190 | ALA | GLN | 3.52 | −1.08 |
| 1190 | ALA | GLY | 0.03 | 5.56 |
| 1190 | ALA | GLU | 9.94 | −1.96 |
| 1190 | ALA | CYS | −0.27 | −0.22 |
| 1190 | ALA | ASP | 0.57 | 7.2 |
| 1190 | ALA | SER | −0.3 | −0.46 |
| 1190 | ALA | LYS | −1.19 | 11.56 |
| 1190 | ALA | PRO | −0.34 | 120.3 |

TABLE 1-continued

| Single Amino Acid Mutations in HR2 | | | | |
|---|---|---|---|---|
| R # | WT | MUT | Δ Aff. | Δ Stab. |
| 1190 | ALA | HIE | 0.21 | 4.91 |
| 1190 | ALA | ASN | −0.12 | 5.11 |
| 1190 | ALA | HIP | −0.19 | 5.99 |
| 1190 | ALA | VAL | −0.16 | 14.94 |
| 1190 | ALA | THR | −0.21 | −4.03 |
| 1190 | ALA | HID | −0.23 | 1.1 |
| 1190 | ALA | TRP | −0.81 | 28.65 |
| 1190 | ALA | PHE | −0.22 | 8 |
| 1190 | ALA | MET | −0.73 | −7.35 |
| 1190 | ALA | LEU | −0.28 | 34.7 |
| 1190 | ALA | ARG | −0.32 | −7.57 |
| 1190 | ALA | TYR | −5.65 | 8.56 |
| 1191 | LYS | ILE | 0.31 | −8.69 |
| 1191 | LYS | GLN | 0.39 | −4.44 |
| 1191 | LYS | GLY | 0.3 | 3.1 |
| 1191 | LYS | GLU | 0.72 | 1.18 |
| 1191 | LYS | CYS | 0.23 | −0.05 |
| 1191 | LYS | ASP | 0.76 | 6.95 |
| 1191 | LYS | SER | 0.25 | −1.62 |
| 1191 | LYS | PRO | 0.23 | 50.85 |
| 1191 | LYS | HIE | 0.34 | −2.08 |
| 1191 | LYS | ASN | 0.24 | −3.52 |
| 1191 | LYS | HIP | −0.01 | −11.08 |
| 1191 | LYS | VAL | 0.3 | −5.68 |
| 1191 | LYS | THR | 0.2 | −3.01 |
| 1191 | LYS | HID | 0.25 | −8.45 |
| 1191 | LYS | TRP | 0.38 | 0.18 |
| 1191 | LYS | PHE | 0.33 | −1.07 |
| 1191 | LYS | ALA | 0.27 | 0.22 |
| 1191 | LYS | MET | 0.27 | −7.48 |
| 1191 | LYS | LEU | 0.31 | −6.11 |
| 1191 | LYS | ARG | 0.09 | −17.9 |
| 1191 | LYS | TYR | 0.32 | −5.02 |
| 1191 | LYS | ILE | 0.31 | −8.69 |
| 1191 | LYS | GLN | 0.39 | −4.44 |
| 1191 | LYS | GLY | 0.3 | 3.1 |
| 1191 | LYS | GLU | 0.72 | 1.18 |
| 1191 | LYS | CYS | 0.23 | −0.05 |
| 1191 | LYS | ASP | 0.76 | 6.95 |
| 1191 | LYS | SER | 0.25 | −1.62 |
| 1191 | LYS | PRO | 0.23 | 50.85 |
| 1191 | LYS | HIE | 0.34 | −2.08 |
| 1191 | LYS | ASN | 0.24 | −3.52 |
| 1191 | LYS | HIP | −0.01 | −11.08 |
| 1191 | LYS | VAL | 0.3 | −5.68 |
| 1191 | LYS | THR | 0.2 | −3.01 |
| 1191 | LYS | HID | 0.25 | −8.45 |
| 1191 | LYS | TRP | 0.38 | 0.18 |
| 1191 | LYS | PHE | 0.33 | −1.07 |
| 1191 | LYS | ALA | 0.27 | 0.22 |
| 1191 | LYS | MET | 0.27 | −7.48 |
| 1191 | LYS | LEU | 0.31 | −6.1 |
| 1191 | LYS | ARG | 0.09 | −17.9 |
| 1191 | LYS | TYR | 0.32 | −5.02 |
| 1191 | LYS | ILE | 0.31 | −8.69 |
| 1191 | LYS | GLN | 0.39 | −4.44 |
| 1191 | LYS | GLY | 0.3 | 3.1 |
| 1191 | LYS | GLU | 0.62 | 1.15 |
| 1191 | LYS | CYS | 0.23 | −0.05 |
| 1191 | LYS | ASP | 0.76 | 6.95 |
| 1191 | LYS | SER | 0.25 | −1.62 |
| 1191 | LYS | PRO | 0.23 | 50.85 |
| 1191 | LYS | HIE | 0.34 | −2.08 |
| 1191 | LYS | ASN | 0.24 | −3.52 |
| 1191 | LYS | HIP | −0.01 | −11.08 |
| 1191 | LYS | VAL | 0.3 | −5.67 |
| 1191 | LYS | THR | 0.2 | −3.01 |
| 1191 | LYS | HID | 0.25 | −8.46 |
| 1191 | LYS | TRP | 0.38 | 0.18 |
| 1191 | LYS | PHE | 0.33 | −1.07 |
| 1191 | LYS | ALA | 0.27 | 0.22 |
| 1191 | LYS | MET | 0.27 | −7.48 |
| 1191 | LYS | LEU | 0.31 | −6.11 |
| 1191 | LYS | ARG | 0.09 | −17.9 |
| 1191 | LYS | TYR | 0.32 | −5.02 |
| 1191 | LYS | ILE | 0.31 | −8.69 |

TABLE 1-continued

| Single Amino Acid Mutations in HR2 | | | | |
|---|---|---|---|---|
| R # | WT | MUT | Δ Aff. | Δ Stab. |
| 1191 | LYS | GLN | 0.39 | −4.44 |
| 1191 | LYS | GLY | 0.3 | 3.1 |
| 1191 | LYS | GLU | 0.62 | 1.14 |
| 1191 | LYS | CYS | 0.23 | −0.05 |
| 1191 | LYS | ASP | 0.76 | 6.95 |
| 1191 | LYS | SER | 0.25 | −1.62 |
| 1191 | LYS | PRO | 0.23 | 50.85 |
| 1191 | LYS | HIE | 0.34 | −2.08 |
| 1191 | LYS | ASN | 0.24 | −3.52 |
| 1191 | LYS | HIP | −0.01 | −11.08 |
| 1191 | LYS | VAL | 0.3 | −5.68 |
| 1191 | LYS | THR | 0.2 | −3.01 |
| 1191 | LYS | HID | 0.25 | −8.45 |
| 1191 | LYS | TRP | 0.38 | 0.18 |
| 1191 | LYS | PHE | 0.33 | −1.07 |
| 1191 | LYS | ALA | 0.27 | 0.22 |
| 1191 | LYS | MET | 0.27 | −7.48 |
| 1191 | LYS | LEU | 0.31 | −6.11 |
| 1191 | LYS | ARG | 0.09 | −17.9 |
| 1191 | LYS | TYR | 0.32 | −5.02 |
| 1191 | LYS | ILE | 0.31 | −8.69 |
| 1191 | LYS | GLN | 0.39 | −4.44 |
| 1191 | LYS | GLY | 0.3 | 3.1 |
| 1191 | LYS | GLU | 0.72 | 1.18 |
| 1191 | LYS | CYS | 0.23 | −0.05 |
| 1191 | LYS | ASP | 0.76 | 6.95 |
| 1191 | LYS | SER | 0.25 | −1.62 |
| 1191 | LYS | PRO | 0.23 | 50.85 |
| 1191 | LYS | HIE | 0.35 | −2.08 |
| 1191 | LYS | ASN | 0.24 | −3.52 |
| 1191 | LYS | HIP | 0.1 | −11.08 |
| 1191 | LYS | VAL | 0.3 | −5.67 |
| 1191 | LYS | THR | 0.21 | −3.01 |
| 1191 | LYS | HID | 0.25 | −8.46 |
| 1191 | LYS | TRP | 0.38 | 0.18 |
| 1191 | LYS | PHE | 0.33 | −1.07 |
| 1191 | LYS | ALA | 0.27 | 0.22 |
| 1191 | LYS | MET | 0.27 | −7.48 |
| 1191 | LYS | LEU | 0.31 | −6.11 |
| 1191 | LYS | ARG | 0.09 | −17.9 |
| 1191 | LYS | TYR | 0.32 | −5.02 |
| 1191 | LYS | ILE | 0.31 | −8.69 |
| 1191 | LYS | GLN | 0.39 | −4.44 |
| 1191 | LYS | GLY | 0.3 | 3.1 |
| 1191 | LYS | GLU | 0.72 | 1.17 |
| 1191 | LYS | CYS | 0.23 | −0.05 |
| 1191 | LYS | ASP | 0.76 | 6.95 |
| 1191 | LYS | SER | 0.25 | −1.62 |
| 1191 | LYS | PRO | 0.23 | 50.85 |
| 1191 | LYS | HIE | 0.34 | −2.08 |
| 1191 | LYS | ASN | 0.24 | −3.52 |
| 1191 | LYS | HIP | 0.1 | −11.08 |
| 1191 | LYS | VAL | 0.3 | −5.67 |
| 1191 | LYS | THR | 0.21 | −3.01 |
| 1191 | LYS | HID | 0.25 | −8.45 |
| 1191 | LYS | TRP | 0.38 | 0.18 |
| 1191 | LYS | PHE | 0.33 | −1.07 |
| 1191 | LYS | ALA | 0.27 | 0.22 |
| 1191 | LYS | MET | 0.27 | −7.48 |
| 1191 | LYS | LEU | 0.31 | −6.11 |
| 1191 | LYS | ARG | 0.09 | −17.9 |
| 1191 | LYS | TYR | 0.32 | −5.02 |
| 1191 | LYS | ILE | 0.31 | −8.69 |
| 1191 | LYS | GLN | 0.39 | −4.44 |
| 1191 | LYS | GLY | 0.3 | 3.1 |
| 1191 | LYS | GLU | 0.72 | 1.18 |
| 1191 | LYS | CYS | 0.23 | −0.05 |
| 1191 | LYS | ASP | 0.76 | 6.95 |
| 1191 | LYS | SER | 0.25 | −1.62 |
| 1191 | LYS | PRO | 0.23 | 50.85 |
| 1191 | LYS | HIE | 0.35 | −2.08 |
| 1191 | LYS | ASN | 0.24 | −3.52 |
| 1191 | LYS | HIP | 0.1 | −11.08 |
| 1191 | LYS | VAL | 0.3 | −5.68 |
| 1191 | LYS | THR | 0.2 | −3.01 |
| 1191 | LYS | HID | 0.25 | −8.45 |

TABLE 1-continued

Single Amino Acid Mutations in HR2

| R # | WT | MUT | Δ Aff. | Δ Stab. |
|---|---|---|---|---|
| 1191 | LYS | TRP | 0.38 | 0.18 |
| 1191 | LYS | PHE | 0.33 | −1.07 |
| 1191 | LYS | ALA | 0.27 | 0.22 |
| 1191 | LYS | MET | 0.27 | −7.48 |
| 1191 | LYS | LEU | 0.31 | −6.11 |
| 1191 | LYS | ARG | 0.09 | −17.9 |
| 1191 | LYS | TYR | 0.32 | −5.02 |
| 1192 | ASN | ILE | 0.02 | −2.36 |
| 1192 | ASN | GLN | 0.04 | −2.94 |
| 1192 | ASN | GLY | −0.03 | 0.4 |
| 1192 | ASN | GLU | 0.37 | 4.71 |
| 1192 | ASN | CYS | −0.08 | −0.43 |
| 1192 | ASN | ASP | 0.7 | 8.7 |
| 1192 | ASN | SER | −0.01 | −0.13 |
| 1192 | ASN | LYS | −0.3 | −0.07 |
| 1192 | ASN | PRO | 0.02 | 66.12 |
| 1192 | ASN | HIE | −0.02 | 2.97 |
| 1192 | ASN | HIP | −0.35 | −7.7 |
| 1192 | ASN | VAL | −0.02 | −2.52 |
| 1192 | ASN | THR | −0.04 | −3.28 |
| 1192 | ASN | HID | −0.03 | 2.08 |
| 1192 | ASN | TRP | −0.23 | 3.27 |
| 1192 | ASN | PHE | −0.01 | 4.52 |
| 1192 | ASN | ALA | −0.03 | −2.34 |
| 1192 | ASN | MET | 0.02 | −2.62 |
| 1192 | ASN | LEU | −0.45 | −4.27 |
| 1192 | ASN | ARG | 2.58 | −14.87 |
| 1192 | ASN | TYR | 0.36 | 4.41 |
| 1192 | ASN | ILE | 0.02 | −2.36 |
| 1192 | ASN | GLN | 0.04 | −2.94 |
| 1192 | ASN | GLY | −0.03 | 0.4 |
| 1192 | ASN | GLU | 0.37 | 4.71 |
| 1192 | ASN | CYS | −0.08 | −0.43 |
| 1192 | ASN | ASP | 0.7 | 8.7 |
| 1192 | ASN | SER | −0.01 | −0.13 |
| 1192 | ASN | LYS | −0.3 | −0.07 |
| 1192 | ASN | PRO | 0.02 | 66.12 |
| 1192 | ASN | HIE | −0.02 | 2.97 |
| 1192 | ASN | HIP | −0.35 | −7.7 |
| 1192 | ASN | VAL | −0.02 | −2.52 |
| 1192 | ASN | THR | −0.04 | −3.28 |
| 1192 | ASN | HID | −0.03 | 2.09 |
| 1192 | ASN | TRP | −0.23 | 3.27 |
| 1192 | ASN | PHE | −0.01 | 4.52 |
| 1192 | ASN | ALA | −0.03 | −2.34 |
| 1192 | ASN | MET | 0.02 | −2.62 |
| 1192 | ASN | LEU | −0.45 | −4.27 |
| 1192 | ASN | ARG | 2.58 | −14.87 |
| 1192 | ASN | TYR | 0.36 | 4.42 |
| 1192 | ASN | ILE | 0.02 | −2.36 |
| 1192 | ASN | GLN | 0.04 | −2.94 |
| 1192 | ASN | GLY | −0.03 | 0.4 |
| 1192 | ASN | GLU | 0.37 | 4.71 |
| 1192 | ASN | CYS | −0.08 | −0.43 |
| 1192 | ASN | ASP | 0.7 | 8.7 |
| 1192 | ASN | SER | −0.01 | −0.13 |
| 1192 | ASN | LYS | −0.3 | −0.07 |
| 1192 | ASN | PRO | 0.02 | 66.12 |
| 1192 | ASN | HIE | −0.02 | 2.97 |
| 1192 | ASN | HIP | −0.35 | −7.7 |
| 1192 | ASN | VAL | −0.02 | −2.52 |
| 1192 | ASN | THR | −0.04 | −3.28 |
| 1192 | ASN | HID | −0.03 | 2.1 |
| 1192 | ASN | TRP | −0.24 | 3.26 |
| 1192 | ASN | PHE | −0.01 | 4.52 |
| 1192 | ASN | ALA | −0.03 | −2.34 |
| 1192 | ASN | MET | 0.02 | −2.62 |
| 1192 | ASN | LEU | −0.45 | −4.27 |
| 1192 | ASN | ARG | 2.58 | −14.87 |
| 1192 | ASN | TYR | 0.36 | 4.41 |
| 1192 | ASN | ILE | 0.02 | −2.36 |
| 1192 | ASN | GLN | 0.04 | −2.94 |
| 1192 | ASN | GLY | −0.03 | 0.4 |
| 1192 | ASN | GLU | 0.37 | 4.71 |
| 1192 | ASN | CYS | −0.08 | −0.43 |
| 1192 | ASN | ASP | 0.7 | 8.7 |

TABLE 1-continued

Single Amino Acid Mutations in HR2

| R # | WT | MUT | Δ Aff. | Δ Stab. |
|---|---|---|---|---|
| 1192 | ASN | SER | −0.01 | −0.13 |
| 1192 | ASN | LYS | −0.3 | −0.07 |
| 1192 | ASN | PRO | 0.02 | 66.12 |
| 1192 | ASN | HIE | −0.02 | 2.97 |
| 1192 | ASN | HIP | −0.35 | −7.7 |
| 1192 | ASN | VAL | −0.02 | −2.52 |
| 1192 | ASN | THR | −0.04 | −3.28 |
| 1192 | ASN | HID | −0.03 | 2.08 |
| 1192 | ASN | TRP | −0.23 | 3.26 |
| 1192 | ASN | PHE | −0.01 | 4.52 |
| 1192 | ASN | ALA | −0.03 | −2.34 |
| 1192 | ASN | MET | 0.02 | −2.62 |
| 1192 | ASN | LEU | −0.45 | −4.27 |
| 1192 | ASN | ARG | 2.58 | −14.87 |
| 1192 | ASN | TYR | 0.36 | 4.41 |
| 1192 | ASN | ILE | 0.02 | −2.36 |
| 1192 | ASN | GLN | 0.04 | −2.94 |
| 1192 | ASN | GLY | −0.03 | 0.4 |
| 1192 | ASN | GLU | 0.37 | 4.71 |
| 1192 | ASN | CYS | −0.08 | −0.43 |
| 1192 | ASN | ASP | 0.7 | 8.7 |
| 1192 | ASN | SER | −0.01 | −0.13 |
| 1192 | ASN | LYS | −0.3 | −0.07 |
| 1192 | ASN | PRO | 0.02 | 66.12 |
| 1192 | ASN | HIE | −0.02 | 2.97 |
| 1192 | ASN | HIP | −0.35 | −7.7 |
| 1192 | ASN | VAL | −0.02 | −2.52 |
| 1192 | ASN | THR | −0.04 | −3.28 |
| 1192 | ASN | HID | −0.03 | 2.08 |
| 1192 | ASN | TRP | −0.23 | 3.26 |
| 1192 | ASN | PHE | −0.01 | 4.52 |
| 1192 | ASN | ALA | −0.03 | −2.34 |
| 1192 | ASN | MET | 0.02 | −2.62 |
| 1192 | ASN | LEU | −0.45 | −4.27 |
| 1192 | ASN | ARG | 2.58 | −14.87 |
| 1192 | ASN | TYR | 0.36 | 4.41 |
| 1192 | ASN | ILE | 0.02 | −2.36 |
| 1192 | ASN | GLN | 0.04 | −2.94 |
| 1192 | ASN | GLY | −0.03 | 0.4 |
| 1192 | ASN | GLU | 0.37 | 4.71 |
| 1192 | ASN | CYS | −0.08 | −0.43 |
| 1192 | ASN | ASP | 0.7 | 8.7 |
| 1192 | ASN | SER | −0.01 | −0.13 |
| 1192 | ASN | LYS | −0.3 | −0.07 |
| 1192 | ASN | PRO | 0.02 | 66.12 |
| 1192 | ASN | HIE | −0.02 | 2.97 |
| 1192 | ASN | HIP | −0.35 | −7.7 |
| 1192 | ASN | VAL | −0.02 | −2.52 |
| 1192 | ASN | THR | −0.04 | −3.28 |
| 1192 | ASN | HID | −0.03 | 2.08 |
| 1192 | ASN | TRP | −0.23 | 3.26 |
| 1192 | ASN | PHE | −0.01 | 4.52 |
| 1192 | ASN | ALA | −0.03 | −2.34 |
| 1192 | ASN | MET | 0.02 | −2.62 |
| 1192 | ASN | LEU | −0.45 | −4.27 |
| 1192 | ASN | ARG | 2.58 | −14.87 |
| 1192 | ASN | TYR | 0.36 | 4.41 |
| 1193 | LEU | ILE | 0.16 | 13.77 |
| 1193 | LEU | GLN | 0.24 | 15.52 |
| 1193 | LEU | GLY | −0.26 | 28.71 |
| 1193 | LEU | GLU | 1.99 | 23.61 |
| 1193 | LEU | CYS | −0.26 | 20.25 |
| 1193 | LEU | ASP | 1.5 | 33.53 |
| 1193 | LEU | SER | −0.34 | 19.68 |
| 1193 | LEU | LYS | −2.31 | 30 |
| 1193 | LEU | PRO | 0.08 | 106.1 |
| 1193 | LEU | HIE | 0.13 | 17.39 |
| 1193 | LEU | ASN | 0.03 | 22.74 |
| 1193 | LEU | HIP | −1.66 | 13.31 |
| 1193 | LEU | VAL | 0.02 | 19.32 |
| 1193 | LEU | THR | −0.09 | 19.42 |
| 1193 | LEU | HID | 0.44 | 10.2 |
| 1193 | LEU | TRP | −0.71 | 61.98 |
| 1193 | LEU | PHE | −0.11 | 22.23 |
| 1193 | LEU | ALA | −0.3 | 22.87 |
| 1193 | LEU | MET | −0.22 | −5.85 |

TABLE 1-continued

Single Amino Acid Mutations in HR2

| R # | WT | MUT | Δ Aff. | Δ Stab. |
|---|---|---|---|---|
| 1193 | LEU | ARG | −2.22 | 10.71 |
| 1193 | LEU | TYR | 0.13 | 27.38 |
| 1193 | LEU | ILE | 0.16 | 13.77 |
| 1193 | LEU | GLN | 0.24 | 15.52 |
| 1193 | LEU | GLY | −0.26 | 28.71 |
| 1193 | LEU | GLU | 1.99 | 23.61 |
| 1193 | LEU | CYS | −0.26 | 20.25 |
| 1193 | LEU | ASP | 1.5 | 33.53 |
| 1193 | LEU | SER | −0.34 | 19.68 |
| 1193 | LEU | LYS | −2.31 | 30 |
| 1193 | LEU | PRO | 0.08 | 106.1 |
| 1193 | LEU | HIE | 0.13 | 17.39 |
| 1193 | LEU | ASN | 0.03 | 22.74 |
| 1193 | LEU | HIP | −1.66 | 13.31 |
| 1193 | LEU | VAL | 0.02 | 19.32 |
| 1193 | LEU | THR | −0.09 | 19.42 |
| 1193 | LEU | HID | 0.44 | 10.21 |
| 1193 | LEU | TRP | −0.71 | 61.98 |
| 1193 | LEU | PHE | −0.11 | 22.23 |
| 1193 | LEU | ALA | −0.3 | 22.87 |
| 1193 | LEU | MET | −0.22 | −5.85 |
| 1193 | LEU | ARG | −2.22 | 10.71 |
| 1193 | LEU | TYR | 0.13 | 27.38 |
| 1193 | LEU | ILE | 0.16 | 13.77 |
| 1193 | LEU | GLN | 0.24 | 15.52 |
| 1193 | LEU | GLY | −0.26 | 28.71 |
| 1193 | LEU | GLU | 1.99 | 23.61 |
| 1193 | LEU | CYS | −0.26 | 20.25 |
| 1193 | LEU | ASP | 1.5 | 33.53 |
| 1193 | LEU | SER | −0.34 | 19.68 |
| 1193 | LEU | LYS | −2.31 | 30 |
| 1193 | LEU | PRO | 0.08 | 106.1 |
| 1193 | LEU | HIE | 0.13 | 17.39 |
| 1193 | LEU | ASN | 0.03 | 22.74 |
| 1193 | LEU | HIP | −1.66 | 13.31 |
| 1193 | LEU | VAL | 0.02 | 19.32 |
| 1193 | LEU | THR | −0.09 | 19.42 |
| 1193 | LEU | HID | 0.44 | 10.21 |
| 1193 | LEU | TRP | −0.71 | 61.98 |
| 1193 | LEU | PHE | −0.11 | 22.23 |
| 1193 | LEU | ALA | −0.3 | 22.87 |
| 1193 | LEU | MET | −0.22 | −5.85 |
| 1193 | LEU | ARG | −2.22 | 10.71 |
| 1193 | LEU | TYR | 0.13 | 27.38 |
| 1193 | LEU | ILE | 0.16 | 13.77 |
| 1193 | LEU | GLN | 0.24 | 15.52 |
| 1193 | LEU | GLY | −0.26 | 28.71 |
| 1193 | LEU | GLU | 1.99 | 23.61 |
| 1193 | LEU | CYS | −0.26 | 20.25 |
| 1193 | LEU | ASP | 1.5 | 33.53 |
| 1193 | LEU | SER | −0.34 | 19.68 |
| 1193 | LEU | LYS | −2.31 | 30 |
| 1193 | LEU | PRO | 0.08 | 106.1 |
| 1193 | LEU | HIE | 0.13 | 17.39 |
| 1193 | LEU | ASN | 0.03 | 22.74 |
| 1193 | LEU | HIP | −1.66 | 13.31 |
| 1193 | LEU | VAL | 0.02 | 19.32 |
| 1193 | LEU | THR | −0.09 | 19.42 |
| 1193 | LEU | HID | 0.44 | 10.21 |
| 1193 | LEU | TRP | −0.71 | 61.98 |
| 1193 | LEU | PHE | −0.11 | 22.23 |
| 1193 | LEU | ALA | −0.3 | 22.87 |
| 1193 | LEU | MET | −0.22 | −5.85 |
| 1193 | LEU | ARG | −2.22 | 10.71 |
| 1193 | LEU | TYR | 0.13 | 27.38 |
| 1193 | LEU | ILE | 0.16 | 13.77 |
| 1193 | LEU | GLN | 0.24 | 15.52 |
| 1193 | LhU | GLY | −0.26 | 28.71 |
| 1193 | LEU | GLU | 1.99 | 23.61 |
| 1193 | LEU | CYS | −0.26 | 20.25 |
| 1193 | LEU | ASP | 1.5 | 33.53 |
| 1193 | LEU | SER | −0.34 | 19.68 |
| 1193 | LEU | LYS | −2.31 | 30 |
| 1193 | LEU | PRO | 0.08 | 106.1 |
| 1193 | LEU | HIE | 0.13 | 17.39 |
| 1193 | LEU | ASN | 0.03 | 22.74 |

TABLE 1-continued

Single Amino Acid Mutations in HR2

| R # | WT | MUT | Δ Aff. | Δ Stab. |
|---|---|---|---|---|
| 1193 | LEU | HIP | −1.66 | 13.31 |
| 1193 | LEU | VAL | 0.02 | 19.32 |
| 1193 | LEU | THR | −0.09 | 19.42 |
| 1193 | LEU | HID | 0.44 | 10.2 |
| 1193 | LEU | TRP | −0.71 | 61.98 |
| 1193 | LEU | PHE | −0.11 | 22.23 |
| 1193 | LEU | ALA | −0.3 | 22.87 |
| 1193 | LEU | MET | −0.22 | −5.85 |
| 1193 | LEU | ARG | −2.22 | 10.71 |
| 1193 | LEU | TYR | 0.13 | 27.38 |
| 1194 | ASN | ILE | −0.1 | 2.69 |
| 1194 | ASN | GLN | −0.07 | 1.46 |
| 1194 | ASN | GLY | −0.1 | 4.6 |
| 1194 | ASN | GLU | 0.47 | 3.35 |
| 1194 | ASN | CYS | −0.15 | 1.55 |
| 1194 | ASN | ASP | 0.49 | 3.82 |
| 1194 | ASN | SER | −0.13 | 0.96 |
| 1194 | ASN | LYS | −0.34 | 4.05 |
| 1194 | ASN | PRO | −0.33 | 81.47 |
| 1194 | ASN | HIE | 0.1 | −1.11 |
| 1194 | ASN | HIP | −0.51 | −4.03 |
| 1194 | ASN | VAL | −0.11 | 3.91 |
| 1194 | ASN | THR | −0.14 | 0.78 |
| 1194 | ASN | HID | −0.03 | 3.36 |
| 1194 | ASN | TRP | −3.34 | 7.76 |
| 1194 | ASN | PHE | −0.04 | −4.66 |
| 1194 | ASN | ALA | −0.12 | 1.83 |
| 1194 | ASN | MET | −0.03 | −3.02 |
| 1194 | ASN | LEU | −0.22 | −3.38 |
| 1194 | ASN | ARG | −0.51 | −2.6 |
| 1194 | ASN | TYR | 0.12 | −3.72 |
| 1194 | ASN | ILE | −0.1 | 2.69 |
| 1194 | ASN | GLN | −0.07 | 1.46 |
| 1194 | ASN | GLY | −0.1 | 4.6 |
| 1194 | ASN | GLU | 0.47 | 3.35 |
| 1194 | ASN | CYS | −0.15 | 1.55 |
| 1194 | ASN | ASP | 0.49 | 3.82 |
| 1194 | ASN | SER | −0.13 | 0.96 |
| 1194 | ASN | LYS | −0.34 | 4.05 |
| 1194 | ASN | PRO | −0.33 | 81.47 |
| 1194 | ASN | HIE | 0.1 | −1.11 |
| 1194 | ASN | HIP | −0.51 | −4.03 |
| 1194 | ASN | VAL | −0.11 | 3.91 |
| 1194 | ASN | THR | −0.14 | 0.78 |
| 1194 | ASN | HID | −0.03 | 3.36 |
| 1194 | ASN | TRP | −3.34 | 7.76 |
| 1194 | ASN | PHE | −0.04 | −4.66 |
| 1194 | ASN | ALA | −0.12 | 1.83 |
| 1194 | ASN | MET | −0.03 | −3.02 |
| 1194 | ASN | LEU | −0.22 | −3.38 |
| 1194 | ASN | ARG | −0.51 | −2.6 |
| 1194 | ASN | TYR | 0.12 | −3.72 |
| 1194 | ASN | ILE | −0.1 | 2.69 |
| 1194 | ASN | GLN | −0.07 | 1.46 |
| 1194 | ASN | GLY | −0.1 | 4.6 |
| 1194 | ASN | GLU | 0.47 | 3.35 |
| 1194 | ASN | CYS | −0.15 | 1.55 |
| 1194 | ASN | ASP | 0.49 | 3.82 |
| 1194 | ASN | SER | −0.13 | 0.96 |
| 1194 | ASN | LYS | −0.34 | 4.05 |
| 1194 | ASN | PRO | −0.33 | 81.47 |
| 1194 | ASN | HIE | 0.1 | −1.11 |
| 1194 | ASN | HIP | −0.51 | −4.03 |
| 1194 | ASN | VAL | −0.11 | 3.91 |
| 1194 | ASN | THR | −0.14 | 0.78 |
| 1194 | ASN | HID | −0.03 | 3.36 |
| 1194 | ASN | TRP | −3.34 | 7.76 |
| 1194 | ASN | PHE | −0.04 | −4.66 |
| 1194 | ASN | ALA | −0.12 | 1.83 |
| 1194 | ASN | MET | −0.03 | −3.02 |
| 1194 | ASN | LEU | −0.22 | −3.38 |
| 1194 | ASN | ARG | −0.51 | −2.6 |
| 1194 | ASN | TYR | 0.12 | −3.72 |
| 1194 | ASN | ILE | −0.1 | 2.69 |
| 1194 | ASN | GLN | −0.07 | 1.46 |
| 1194 | ASN | GLY | −0.1 | 4.6 |

TABLE 1-continued

| Single Amino Acid Mutations in HR2 | | | | |
|---|---|---|---|---|
| R # | WT | MUT | Δ Aff. | Δ Stab. |
| 1194 | ASN | GLU | 0.47 | 3.35 |
| 1194 | ASN | CYS | −0.15 | 1.55 |
| 1194 | ASN | ASP | 0.49 | 3.82 |
| 1194 | ASN | SER | −0.13 | 0.96 |
| 1194 | ASN | LYS | −0.34 | 4.05 |
| 1194 | ASN | PRO | −0.33 | 81.47 |
| 1194 | ASN | HIE | 0.1 | −1.11 |
| 1194 | ASN | HIP | −0.51 | −4.03 |
| 1194 | ASN | VAL | −0.11 | 3.91 |
| 1194 | ASN | THR | −0.14 | 0.78 |
| 1194 | ASN | HID | −0.03 | 3.36 |
| 1194 | ASN | TRP | −3.34 | 7.76 |
| 1194 | ASN | PHE | −0.04 | −4.66 |
| 1194 | ASN | ALA | −0.12 | 1.83 |
| 1194 | ASN | MET | −0.03 | −3.02 |
| 1194 | ASN | LEU | −0.22 | −3.38 |
| 1194 | ASN | ARG | −0.51 | −2.6 |
| 1194 | ASN | TYR | 0.12 | −3.72 |
| 1195 | GLU | ILE | −0.38 | −0.14 |
| 1195 | GLU | GLN | −0.31 | 2.04 |
| 1195 | GLU | GLY | −0.33 | 10.76 |
| 1195 | GLU | CYS | −0.37 | 9.38 |
| 1195 | GLU | ASP | 0.09 | 10.03 |
| 1195 | GLU | SER | −0.33 | 10.85 |
| 1195 | GLU | LYS | −0.69 | 9.74 |
| 1195 | GLU | PRO | −0.38 | 26.49 |
| 1195 | GLU | HIE | −0.3 | 3.75 |
| 1195 | GLU | ASN | −0.35 | 9.28 |
| 1195 | GLU | HIP | −0.68 | 0.94 |
| 1195 | GLU | VAL | −0.35 | 2.77 |
| 1195 | GLU | THR | −0.45 | 10.08 |
| 1195 | GLU | HID | −0.3 | 5.64 |
| 1195 | GLU | TRP | −0.56 | 2.37 |
| 1195 | GLU | PHE | −0.8 | 5.44 |
| 1195 | GLU | ALA | −0.33 | 8.83 |
| 1195 | GLU | MET | −0.35 | 2.02 |
| 1195 | GLU | LEU | −0.36 | 0.82 |
| 1195 | GLU | ARG | −0.71 | −3.71 |
| 1195 | GLU | TYR | −0.35 | 2.85 |
| 1195 | GLU | ILE | −0.38 | −0.14 |
| 1195 | GLU | GLN | −0.31 | 2.04 |
| 1195 | GLU | GLY | −0.33 | 10.76 |
| 1195 | GLU | CYS | −0.37 | 9.38 |
| 1195 | GLU | ASP | 0.09 | 10.03 |
| 1195 | GLU | SER | −0.33 | 10.85 |
| 1195 | GLU | LYS | −0.69 | 9.74 |
| 1195 | GLU | PRO | −0.38 | 26.49 |
| 1195 | GLU | HIE | −0.3 | 3.75 |
| 1195 | GLU | ASN | −0.35 | 9.28 |
| 1195 | GLU | HIP | −0.68 | 0.94 |
| 1195 | GLU | VAL | −0.35 | 2.77 |
| 1195 | GLU | THR | −0.45 | 10.08 |
| 1195 | GLU | HID | −0.3 | 5.64 |
| 1195 | GLU | TRP | −0.56 | 2.37 |
| 1195 | GLU | PHE | −0.8 | 5.44 |
| 1195 | GLU | ALA | −0.33 | 8.83 |
| 1195 | GLU | MET | −0.35 | 2.02 |
| 1195 | GLU | LEU | −0.36 | 0.82 |
| 1195 | GLU | ARG | −0.71 | −3.71 |
| 1195 | GLU | TYR | −0.35 | 2.85 |
| 1195 | GLU | ILE | −0.38 | −0.14 |
| 1195 | GLU | GLN | −0.31 | 2.04 |
| 1195 | GLU | GLY | −0.33 | 10.76 |
| 1195 | GLU | CYS | −0.37 | 9.38 |
| 1195 | GLU | ASP | 0.09 | 10.03 |
| 1195 | GLU | SER | −0.33 | 10.85 |
| 1195 | GLU | LYS | −0.69 | 9.74 |
| 1195 | GLU | PRO | −0.38 | 26.49 |
| 1195 | GLU | HIE | −0.3 | 3.75 |
| 1195 | GLU | ASN | −0.35 | 9.28 |
| 1195 | GLU | HIP | −0.68 | 0.94 |
| 1195 | GLU | VAL | −0.35 | 2.77 |
| 1195 | GLU | THR | −0.45 | 10.08 |
| 1195 | GLU | HID | −0.3 | 5.64 |
| 1195 | GLU | TRP | −0.56 | 2.37 |
| 1195 | GLU | PHE | −0.8 | 5.44 |

TABLE 1-continued

| Single Amino Acid Mutations in HR2 | | | | |
|---|---|---|---|---|
| R # | WT | MUT | Δ Aff. | Δ Stab. |
| 1195 | GLU | ALA | −0.33 | 8.83 |
| 1195 | GLU | MET | −0.35 | 2.02 |
| 1195 | GLU | LEU | −0.36 | 0.82 |
| 1195 | GLU | ARG | −0.71 | −3.71 |
| 1195 | GLU | TYR | −0.35 | 2.85 |
| 1195 | GLU | ILE | −0.38 | −0.14 |
| 1195 | GLU | GLN | −0.31 | 2.04 |
| 1195 | GLU | GLY | −0.33 | 10.76 |
| 1195 | GLU | CYS | −0.37 | 9.38 |
| 1195 | GLU | ASP | 0.09 | 10.03 |
| 1195 | GLU | SER | −0.33 | 10.85 |
| 1195 | GLU | LYS | −0.69 | 9.74 |
| 1195 | GLU | PRO | −0.38 | 26.49 |
| 1195 | GLU | HIE | −0.3 | 3.75 |
| 1195 | GLU | ASN | −0.35 | 9.28 |
| 1195 | GLU | HIP | −0.68 | 0.94 |
| 1195 | GLU | VAL | −0.35 | 2.77 |
| 1195 | GLU | THR | −0.45 | 10.08 |
| 1195 | GLU | HID | −0.3 | 5.64 |
| 1195 | GLU | TRP | −0.56 | 2.37 |
| 1195 | GLU | PHE | −0.8 | 5.44 |
| 1195 | GLU | ALA | −0.33 | 8.83 |
| 1195 | GLU | MET | −0.35 | 2.02 |
| 1195 | GLU | LEU | −0.36 | 0.82 |
| 1195 | GLU | ARG | −0.71 | −3.71 |
| 1195 | GLU | TYR | −0.35 | 2.85 |
| 1196 | SER | ILE | 0.36 | 38.8 |
| 1196 | SER | GLN | 0.02 | 36.11 |
| 1196 | SER | GLY | −0.14 | 14 |
| 1196 | SER | GLU | 1.96 | 42.29 |
| 1196 | SER | CYS | 0.02 | 6.02 |
| 1196 | SER | ASP | 2.18 | 41.52 |
| 1196 | SER | LYS | −0.28 | 47.76 |
| 1196 | SER | PRO | 0.04 | 44.44 |
| 1196 | SER | HIE | −1.49 | 30.01 |
| 1196 | SER | ASN | −0.37 | 21.18 |
| 1196 | SER | HIP | −0.35 | 22.79 |
| 1196 | SER | VAL | −0.21 | 16.49 |
| 1196 | SER | THR | −0.41 | 5.74 |
| 1196 | SER | HID | −1.16 | 31.04 |
| 1196 | SER | TRP | 0.11 | 1168.4 |
| 1196 | SER | PHE | −0.08 | 52.68 |
| 1196 | SER | ALA | −0.13 | 2.81 |
| 1196 | SER | MET | −2.23 | 29.3 |
| 1196 | SER | LEU | 0.02 | 83.13 |
| 1196 | SER | ARG | −0.69 | 30.72 |
| 1196 | SER | TYR | 0.01 | 1248.22 |
| 1196 | SER | ILE | 0.36 | 38.8 |
| 1196 | SER | GLN | 0.02 | 36.11 |
| 1196 | SER | GLY | −0.14 | 14 |
| 1196 | SER | GLU | 1.96 | 42.29 |
| 1196 | SER | CYS | 0.02 | 6.02 |
| 1196 | SER | ASP | 2.18 | 41.52 |
| 1196 | SER | LYS | −0.28 | 47.76 |
| 1196 | SER | PRO | 0.04 | 44.44 |
| 1196 | SER | HIE | −1.63 | 29.97 |
| 1196 | SER | ASN | −0.37 | 21.18 |
| 1196 | SER | HIP | −0.35 | 22.79 |
| 1196 | SER | VAL | −0.21 | 16.49 |
| 1196 | SER | THR | −0.41 | 5.74 |
| 1196 | SER | HID | 0.04 | 206.17 |
| 1196 | SER | TRP | 0.11 | 1168.4 |
| 1196 | SER | PHE | −0.08 | 52.68 |
| 1196 | SER | ALA | −0.13 | 2.81 |
| 1196 | SER | MET | −2.23 | 29.3 |
| 1196 | SER | LEU | 0.02 | 83.13 |
| 1196 | SER | ARG | −0.69 | 30.72 |
| 1196 | SER | TYR | 0.01 | 1248.22 |
| 1196 | SER | ILE | 0.36 | 38.8 |
| 1196 | SER | GLN | 0.02 | 36.11 |
| 1196 | SER | GLY | −0.14 | 14 |
| 1196 | SER | GLU | 1.96 | 42.29 |
| 1196 | SER | CYS | 0.02 | 6.02 |
| 1196 | SER | ASP | 2.18 | 41.52 |
| 1196 | SER | LYS | −0.28 | 47.76 |
| 1196 | SER | PRO | 0.04 | 44.44 |

TABLE 1-continued

Single Amino Acid Mutations in HR2

| R # | WT | MUT | Δ Aff. | Δ Stab. |
|---|---|---|---|---|
| 1196 | SER | HIE | −1.61 | 30.02 |
| 1196 | SER | ASN | −0.37 | 21.18 |
| 1196 | SER | HIP | −0.35 | 22.79 |
| 1196 | SER | VAL | −0.21 | 16.49 |
| 1196 | SER | THR | −0.41 | 5.74 |
| 1196 | SER | HID | 0.04 | 206.17 |
| 1196 | SER | TRP | 0.11 | 1168.4 |
| 1196 | SER | PHE | −0.08 | 52.68 |
| 1196 | SER | ALA | −0.13 | 2.81 |
| 1196 | SER | MET | −2.23 | 29.3 |
| 1196 | SER | LEU | 0.02 | 83.13 |
| 1196 | SER | ARG | −0.69 | 30.72 |
| 1196 | SER | TYR | 0.01 | 1248.22 |
| 1197 | LEU | ILE | −0.1 | 7.67 |
| 1197 | LEU | GLN | 0.42 | 10.97 |
| 1197 | LEU | GLY | −0.2 | 17.43 |
| 1197 | LEU | GLU | 1.31 | 19.23 |
| 1197 | LEU | CYS | −0.38 | 12.64 |
| 1197 | LEU | ASP | 1.07 | 25.71 |
| 1197 | LEU | SER | −0.31 | 16.02 |
| 1197 | LEU | LYS | −0.62 | 9.25 |
| 1197 | LEU | PRO | −0.35 | 28.3 |
| 1197 | LEU | HIE | −0.08 | 9.93 |
| 1197 | LEU | ASN | −0.09 | 13.16 |
| 1197 | LEU | HIP | −0.89 | −0.31 |
| 1197 | LEU | VAL | −0.13 | 7.45 |
| 1197 | LEU | THR | −0.23 | 9.73 |
| 1197 | LEU | HID | −0.16 | 9.49 |
| 1197 | LEU | TRP | 0.49 | 7.54 |
| 1197 | LEU | PHE | 0.32 | 6.8 |
| 1197 | LEU | ALA | −0.2 | 14.75 |
| 1197 | LEU | MET | 0.31 | 1.57 |
| 1197 | LEU | ARG | −0.93 | −7.32 |
| 1197 | LEU | TYR | 0.24 | −0.84 |
| 1197 | LEU | ILE | −0.1 | 7.67 |
| 1197 | LEU | GLN | 0.42 | 10.97 |
| 1197 | LEU | GLY | −0.2 | 17.43 |
| 1197 | LEU | GLU | 1.31 | 19.23 |
| 1197 | LEU | CYS | −0.38 | 12.64 |
| 1197 | LEU | ASP | 1.07 | 25.71 |
| 1197 | LEU | SER | −0.31 | 16.02 |
| 1197 | LEU | LYS | −0.62 | 9.25 |
| 1197 | LEU | PRO | −0.35 | 28.3 |
| 1197 | LEU | HIE | −0.08 | 9.93 |
| 1197 | LEU | ASN | −0.09 | 13.16 |
| 1197 | LEU | HIP | −0.89 | −0.31 |
| 1197 | LEU | VAL | −0.13 | 7.45 |
| 1197 | LEU | THR | −0.23 | 9.73 |
| 1197 | LEU | HID | −0.16 | 9.49 |
| 1197 | LEU | TRP | 0.49 | 7.54 |
| 1197 | LEU | PHE | 0.32 | 6.8 |
| 1197 | LEU | ALA | −0.2 | 14.75 |
| 1197 | LEU | MET | 0.31 | 1.57 |
| 1197 | LEU | ARG | −0.93 | −7.32 |
| 1197 | LEU | TYR | 0.24 | −0.84 |
| 1197 | LEU | ILE | −0.1 | 7.67 |
| 1197 | LEU | GLN | 0.42 | 10.97 |
| 1197 | LEU | GLY | −0.2 | 17.43 |
| 1197 | LEU | GLU | 1.31 | 19.23 |
| 1197 | LEU | CYS | −0.38 | 12.64 |
| 1197 | LEU | ASP | 1.07 | 25.71 |
| 1197 | LEU | SER | −0.31 | 16.02 |
| 1197 | LEU | LYS | −0.62 | 9.25 |
| 1197 | LEU | PRO | −0.35 | 28.3 |
| 1197 | LEU | HIE | −0.08 | 9.93 |
| 1197 | LEU | ASN | −0.09 | 13.16 |
| 1197 | LEU | HIP | −0.89 | −0.31 |
| 1197 | LEU | VAL | −0.13 | 7.45 |
| 1197 | LEU | THR | −0.23 | 9.73 |
| 1197 | LEU | HID | −0.16 | 9.49 |
| 1197 | LEU | TRP | 0.49 | 7.54 |
| 1197 | LEU | PHE | 0.32 | 6.8 |
| 1197 | LEU | ALA | −0.2 | 14.75 |
| 1197 | LEU | MET | 0.31 | 1.57 |
| 1197 | LEU | ARG | −0.93 | −7.32 |
| 1197 | LEU | TYR | 0.24 | −0.84 |

TABLE 1-continued

Single Amino Acid Mutations in HR2

| R # | WT | MUT | Δ Aff. | Δ Stab. |
|---|---|---|---|---|
| 1198 | ILE | GLN | 0.47 | 12.38 |
| 1198 | ILE | GLY | −0.28 | 30.62 |
| 1198 | ILE | GLU | 1.41 | 20.73 |
| 1198 | ILE | CYS | −0.37 | 19.52 |
| 1198 | ILE | ASP | 1.45 | 36.51 |
| 1198 | ILE | SER | −0.32 | 23.06 |
| 1198 | ILE | LYS | −2.14 | 32.52 |
| 1198 | ILE | PRO | −0.25 | 92.49 |
| 1198 | ILE | HIE | −0.5 | 23.61 |
| 1198 | ILE | ASN | −0.16 | 25.31 |
| 1198 | ILE | HIP | −1.55 | 28.43 |
| 1198 | ILE | VAL | −0.13 | 8.89 |
| 1198 | ILE | THR | −0.22 | 14.76 |
| 1198 | ILE | HID | 0.24 | 25.61 |
| 1198 | ILE | TRP | −0.62 | 81.97 |
| 1198 | ILE | PHE | 0.33 | 25.87 |
| 1198 | ILE | ALA | −0.25 | 22.81 |
| 1198 | ILE | MET | −0.13 | −1.72 |
| 1198 | ILE | LEU | −0.21 | 5.28 |
| 1198 | ILE | ARG | −2.14 | 19.83 |
| 1198 | ILE | TYR | −0.15 | 85.23 |
| 1198 | ILE | GLN | 0.47 | 12.38 |
| 1198 | ILE | GLY | −0.28 | 30.62 |
| 1198 | ILE | GLU | 1.41 | 20.73 |
| 1198 | ILE | CYS | −0.37 | 19.52 |
| 1198 | ILE | ASP | 1.45 | 36.51 |
| 1198 | ILE | SER | −0.32 | 23.06 |
| 1198 | ILE | LYS | −2.14 | 32.52 |
| 1198 | ILE | PRO | −0.25 | 92.49 |
| 1198 | ILE | HIE | −0.5 | 23.61 |
| 1198 | ILE | ASN | −0.16 | 25.31 |
| 1198 | ILE | HIP | −1.55 | 28.43 |
| 1198 | ILE | VAL | −0.13 | 8.89 |
| 1198 | ILE | THR | −0.22 | 14.76 |
| 1198 | ILE | HID | 0.24 | 25.61 |
| 1198 | ILE | TRP | −0.62 | 81.97 |
| 1198 | ILE | PHE | 0.33 | 25.87 |
| 1198 | ILE | ALA | −0.25 | 22.81 |
| 1198 | ILL | MET | −0.13 | −1.72 |
| 1198 | ILE | LEU | −0.21 | 5.28 |
| 1198 | ILE | ARG | −2.14 | 19.83 |
| 1198 | ILE | TYR | −0.15 | 85.23 |
| 1198 | ILE | GLN | 0.47 | 12.38 |
| 1198 | ILE | GLY | −0.28 | 30.62 |
| 1198 | ILE | GLU | 1.41 | 20.73 |
| 1198 | ILE | CYS | −0.37 | 19.52 |
| 1198 | ILE | ASP | 1.45 | 36.51 |
| 1198 | ILE | SER | −0.32 | 23.06 |
| 1198 | ILE | LYS | −2.14 | 32.52 |
| 1198 | ILE | PRO | −0.25 | 92.49 |
| 1198 | ILE | HIE | −0.5 | 23.61 |
| 1198 | ILE | ASN | −0.16 | 25.31 |
| 1198 | ILE | HIP | −1.55 | 28.43 |
| 1198 | ILE | VAL | −0.13 | 8.89 |
| 1198 | ILE | THR | −0.22 | 14.76 |
| 1198 | ILE | HID | 0.24 | 25.61 |
| 1198 | ILE | TRP | −0.62 | 81.97 |
| 1198 | ILE | PHE | 0.33 | 25.87 |
| 1198 | ILE | ALA | −0.25 | 22.81 |
| 1198 | ILE | MET | −0.13 | −1.72 |
| 1198 | ILE | LEU | −0.21 | 5.28 |
| 1198 | ILE | ARG | −2.14 | 19.83 |
| 1198 | ILE | TYR | −0.15 | 85.23 |
| 1199 | ASP | ILE | −0.46 | −8.5 |
| 1199 | ASP | GLN | 0.11 | −6.32 |
| 1199 | ASP | GLY | −0.5 | −1.39 |
| 1199 | ASP | GLU | 0.85 | −3.56 |
| 1199 | ASP | CYS | −0.54 | −1.39 |
| 1199 | ASP | SER | −0.49 | −2.19 |
| 1199 | ASP | LYS | −0.76 | −3.86 |
| 1199 | ASP | PRO | −0.64 | 4.86 |
| 1199 | ASP | HIE | −0.27 | −8.66 |
| 1199 | ASP | ASN | −0.5 | −1.25 |
| 1199 | ASP | HIP | −0.09 | −12 |
| 1199 | ASP | VAL | −0.48 | −4.63 |
| 1199 | ASP | THR | −0.49 | −5.15 |

TABLE 1-continued

| Single Amino Acid Mutations in HR2 | | | | |
|---|---|---|---|---|
| R # | WT | MUT | Δ Aff. | Δ Stab. |
| 1199 | ASP | HID | −0.32 | −3.22 |
| 1199 | ASP | TRP | −0.23 | −4.97 |
| 1199 | ASP | PHE | −0.2 | −8.4 |
| 1199 | ASP | ALA | −0.51 | −2.63 |
| 1199 | ASP | MET | −3.47 | −7.64 |
| 1199 | ASP | LEU | −0.43 | −10.26 |
| 1199 | ASP | ARG | −0.87 | −15.57 |
| 1199 | ASP | TYR | −8.73 | −1.87 |
| 1199 | ASP | ILE | −0.46 | −8.5 |
| 1199 | ASP | GLN | 0.11 | −6.32 |
| 1199 | ASP | GLY | −0.5 | −1.39 |
| 1199 | ASP | GLU | 0.85 | −3.56 |
| 1199 | ASP | CYS | −0.54 | −1.39 |
| 1199 | ASP | SER | −0.49 | −2.19 |
| 1199 | ASP | LYS | −0.76 | −3.86 |
| 1199 | ASP | PRO | −0.64 | 4.86 |
| 1199 | ASP | HIE | −0.27 | −8.66 |
| 1199 | ASP | ASN | −0.5 | −1.25 |
| 1199 | ASP | HIP | −0.09 | −12 |
| 1199 | ASP | VAL | −0.48 | −4.63 |
| 1199 | ASP | THR | −0.49 | −5.15 |
| 1199 | ASP | HID | −0.32 | −3.22 |
| 1199 | ASP | TRP | −0.23 | −5.09 |
| 1199 | ASP | PHE | −0.2 | −8.4 |
| 1199 | ASP | ALA | −0.51 | −2.63 |
| 1199 | ASP | MET | −3.47 | −7.64 |
| 1199 | ASP | LEU | −0.43 | −10.26 |
| 1199 | ASP | ARG | −0.89 | −14.04 |
| 1199 | ASP | TYR | −24.62 | −1.17 |
| 1199 | ASP | ILE | −0.46 | −8.5 |
| 1199 | ASP | GLN | 0.11 | −6.32 |
| 1199 | ASP | GLY | −0.5 | −1.39 |
| 1199 | ASP | GLU | 0.85 | −3.56 |
| 1199 | ASP | CYS | −0.54 | −1.39 |
| 1199 | ASP | SER | −0.49 | −2.19 |
| 1199 | ASP | LYS | −0.76 | −3.86 |
| 1199 | ASP | PRO | −0.64 | 4.86 |
| 1199 | ASP | HIE | −0.27 | −8.66 |
| 1199 | ASP | ASN | −0.5 | −1.25 |
| 1199 | ASP | HIP | −0.09 | −12 |
| 1199 | ASP | VAL | −0.48 | −4.63 |
| 1199 | ASP | THR | −0.49 | −5.15 |
| 1199 | ASP | HID | −0.32 | −3.22 |
| 1199 | ASP | TRP | −0.23 | −4.99 |
| 1199 | ASP | PHE | −0.2 | −8.4 |
| 1199 | ASP | ALA | −0.51 | −2.63 |
| 1199 | ASP | MET | −3.47 | −7.64 |
| 1199 | ASP | LEU | −0.43 | −10.26 |
| 1199 | ASP | ARG | −0.88 | −14.27 |
| 1199 | ASP | TYR | −18.07 | 0.23 |
| 1200 | LEU | ILE | −0.05 | 3.56 |
| 1200 | LEU | GLN | −0.04 | 12.76 |
| 1200 | LEU | GLY | −0.12 | 18.08 |
| 1200 | LEU | GLU | 0.78 | 12.64 |
| 1200 | LEU | CYS | −0.18 | 15.48 |
| 1200 | LEU | ASP | 0.62 | 19.81 |
| 1200 | LEU | SER | −0.15 | 17.05 |
| 1200 | LEU | LYS | −0.74 | 25.5 |
| 1200 | LEU | PRO | −0.21 | 12.44 |
| 1200 | LEU | HIE | 0.07 | 13.43 |
| 1200 | LEU | ASN | −0.07 | 17.12 |
| 1200 | LEU | HIP | −0.68 | 15.43 |
| 1200 | LEU | VAL | −0.1 | 12.86 |
| 1200 | LEU | THR | −0.02 | 16.64 |
| 1200 | LEU | HID | −0.17 | 11.17 |
| 1200 | LEU | TRP | −0.14 | 11.88 |
| 1200 | LEU | PHE | −0.12 | 11.14 |
| 1200 | LEU | ALA | −0.13 | 14.59 |
| 1200 | LEU | MET | 0 | 1.63 |
| 1200 | LEU | ARG | −0.62 | 16.55 |
| 1200 | LEU | TYR | −0.13 | 12.36 |
| 1200 | LEU | ILE | −0.05 | 3.56 |
| 1200 | LEU | GLN | −0.04 | 12.76 |
| 1200 | LEU | GLY | −0.12 | 18.08 |
| 1200 | LEU | GLU | 0.78 | 12.64 |
| 1200 | LEU | CYS | −0.18 | 15.48 |

TABLE 1-continued

| Single Amino Acid Mutations in HR2 | | | | |
|---|---|---|---|---|
| R # | WT | MUT | Δ Aff. | Δ Stab. |
| 1200 | LEU | ASP | 0.62 | 19.81 |
| 1200 | LEU | SER | −0.15 | 17.05 |
| 1200 | LEU | LYS | −0.74 | 25.5 |
| 1200 | LEU | PRO | −0.21 | 12.44 |
| 1200 | LEU | HIE | 0.07 | 13.43 |
| 1200 | LEU | ASN | −0.07 | 17.12 |
| 1200 | LEU | HIP | −0.68 | 15.43 |
| 1200 | LEU | VAL | −0.1 | 12.86 |
| 1200 | LEU | THR | −0.02 | 16.64 |
| 1200 | LEU | HID | −0.17 | 11.17 |
| 1200 | LEU | TRP | −0.14 | 11.88 |
| 1200 | LEU | PHE | −0.12 | 11.14 |
| 1200 | LEU | ALA | −0.13 | 14.59 |
| 1200 | LEU | MET | 0 | 1.63 |
| 1200 | LEU | ARG | −0.62 | 16.55 |
| 1200 | LEU | TYR | −0.13 | 12.36 |
| 1200 | LEU | ILE | −0.05 | 3.56 |
| 1200 | LEU | GLN | −0.04 | 12.76 |
| 1200 | LEU | GLY | −0.12 | 18.08 |
| 1200 | LEU | GLU | 0.78 | 12.64 |
| 1200 | LEU | CYS | −0.18 | 15.48 |
| 1200 | LEU | ASP | 0.62 | 19.81 |
| 1200 | LEU | SER | −0.15 | 17.05 |
| 1200 | LEU | LYS | −0.74 | 25.5 |
| 1200 | LEU | PRO | −0.21 | 12.44 |
| 1200 | LEU | HIE | 0.07 | 13.43 |
| 1200 | LEU | ASN | −0.07 | 17.12 |
| 1200 | LEU | HIP | −0.68 | 15.43 |
| 1200 | LEU | VAL | −0.1 | 12.86 |
| 1200 | LEU | THR | −0.02 | 16.64 |
| 1200 | LEU | HID | −0.17 | 11.17 |
| 1200 | LEU | TRP | −0.14 | 11.88 |
| 1200 | LEU | PHE | −0.12 | 11.14 |
| 1200 | LEU | ALA | −0.13 | 14.59 |
| 1200 | LEU | MET | 0 | 1.63 |
| 1200 | LEU | ARG | −0.62 | 16.55 |
| 1200 | LEU | TYR | −0.13 | 12.36 |
| 1201 | GLN | ILE | 0.06 | 1.13 |
| 1201 | GLN | GLY | 0.01 | 9.26 |
| 1201 | GLN | GLU | 0.5 | 7.74 |
| 1201 | GLN | CYS | −0.04 | 7.9 |
| 1201 | GLN | ASP | 0.57 | 9.56 |
| 1201 | GLN | SER | −0.02 | 9.76 |
| 1201 | GLN | LYS | 0.65 | 4.59 |
| 1201 | GLN | PRO | −0.02 | 10.24 |
| 1201 | GLN | HIE | 0.03 | 4.52 |
| 1201 | GLN | ASN | −0.02 | 7.01 |
| 1201 | GLN | HIP | −0.37 | −1 |
| 1201 | GLN | VAL | 0.05 | 3.21 |
| 1201 | GLN | THR | 0.07 | 8.5 |
| 1201 | GLN | HID | 0.02 | 6.2 |
| 1201 | GLN | TRP | −0.05 | 7.08 |
| 1201 | GLN | PHE | 0.17 | 3.93 |
| 1201 | GLN | ALA | 0 | 4.8 |
| 1201 | GLN | MET | −0.03 | −6.12 |
| 1201 | GLN | LEU | 0.08 | 0.44 |
| 1201 | GLN | ARG | −0.31 | −2.41 |
| 1201 | GLN | TYR | 0.2 | 4.36 |
| 1201 | GLN | ILE | 0.06 | 1.13 |
| 1201 | GLN | GLY | 0.01 | 9.26 |
| 1201 | GLN | GLU | 0.5 | 7.74 |
| 1201 | GLN | CYS | −0.04 | 7.9 |
| 1201 | GLN | ASP | 0.57 | 9.45 |
| 1201 | GLN | SER | −0.02 | 9.76 |
| 1201 | GLN | LYS | 0.65 | 4.59 |
| 1201 | GLN | PRO | −0.02 | 10.24 |
| 1201 | GLN | HIE | 0.03 | 4.52 |
| 1201 | GLN | ASN | −0.02 | 7.01 |
| 1201 | GLN | HIP | −0.37 | −1 |
| 1201 | GLN | VAL | 0.05 | 3.21 |
| 1201 | GLN | THR | 0.07 | 8.5 |
| 1201 | GLN | HID | 0.02 | 6.2 |
| 1201 | GLN | TRP | −0.05 | 7.08 |
| 1201 | GLN | PHE | 0.17 | 3.93 |
| 1201 | GLN | ALA | 0 | 4.8 |
| 1201 | GLN | MET | −0.03 | −6.12 |

TABLE 1-continued

Single Amino Acid Mutations in HR2

| R # | WT | MUT | Δ Aff. | Δ Stab. |
|---|---|---|---|---|
| 1201 | GLN | LEU | 0.08 | 0.44 |
| 1201 | GLN | ARG | −0.31 | −2.41 |
| 1201 | GLN | TYR | 0.2 | 4.36 |
| 1201 | GLN | ILE | 0.06 | 1.13 |
| 1201 | GLN | GLY | 0.01 | 9.26 |
| 1201 | GLN | GLU | 0.5 | 7.74 |
| 1201 | GLN | CYS | −0.04 | 7.9 |
| 1201 | GLN | ASP | 0.57 | 9.33 |
| 1201 | GLN | SER | −0.02 | 9.76 |
| 1201 | GLN | LYS | 0.65 | 4.59 |
| 1201 | GLN | PRO | −0.02 | 10.24 |
| 1201 | GLN | HIE | 0.03 | 4.52 |
| 1201 | GLN | ASN | −0.02 | 7.01 |
| 1201 | GLN | HIP | −0.37 | −1 |
| 1201 | GLN | VAL | 0.05 | 3.21 |
| 1201 | GLN | THR | 0.07 | 8.5 |
| 1201 | GLN | HID | 0.02 | 6.2 |
| 1201 | GLN | TRP | −0.05 | 7.08 |
| 1201 | GLN | PHE | 0.17 | 3.93 |
| 1201 | GLN | ALA | 0 | 4.8 |
| 1201 | GLN | MET | −0.03 | −6.12 |
| 1201 | GLN | LEU | 0.08 | 0.44 |
| 1201 | GLN | ARG | −0.33 | −2.39 |
| 1201 | GLN | TYR | 0.2 | 4.36 |
| 1202 | GLU | ILE | −0.45 | 41.43 |
| 1202 | GLU | GLN | −0.42 | −15.68 |
| 1202 | GLU | GLY | −0.44 | 18.98 |
| 1202 | GLU | CYS | −0.48 | 25.13 |
| 1202 | GLU | ASP | 0 | −10.67 |
| 1202 | GLU | SER | −0.43 | 24.92 |
| 1202 | GLU | LYS | −0.4 | 21.88 |
| 1202 | GLU | PRO | −0.5 | 86.02 |
| 1202 | GLU | HIE | −0.41 | 12.12 |
| 1202 | GLU | ASN | −0.44 | −14.97 |
| 1202 | GLU | HIP | −0.84 | 18.29 |
| 1202 | GLU | VAL | −0.45 | 35.37 |
| 1202 | GLU | THR | −0.42 | 24.36 |
| 1202 | GLU | HID | −0.45 | 19.72 |
| 1202 | GLU | TRP | −0.42 | 8.84 |
| 1202 | GLU | PHE | −0.45 | 28.47 |
| 1202 | GLU | ALA | −0.43 | 24.3 |
| 1202 | GLU | MET | −0.42 | 17.22 |
| 1202 | GLU | LEU | −0.82 | 32.05 |
| 1202 | GLU | ARG | −1.01 | −7.58 |
| 1202 | GLU | TYR | −0.43 | 20.74 |
| 1202 | GLU | ILE | −0.45 | 41.43 |
| 1202 | GLU | GLN | −0.42 | −15.68 |
| 1202 | GLU | GLY | −0.44 | 18.98 |
| 1202 | GLU | CYS | −0.48 | 25.13 |
| 1202 | GLU | ASP | 0 | −10.67 |
| 1202 | GLU | SER | −0.43 | 24.92 |
| 1202 | GLU | LYS | −0.4 | 21.88 |
| 1202 | GLU | PRO | −0.5 | 86.02 |
| 1202 | GLU | HIE | −0.41 | 12.12 |
| 1202 | GLU | ASN | −0.44 | −14.97 |
| 1202 | GLU | HIP | −0.84 | 18.29 |
| 1202 | GLU | VAL | −0.45 | 35.37 |
| 1202 | GLU | THR | −0.42 | 24.36 |
| 1202 | GLU | HID | −0.45 | 19.72 |
| 1202 | GLU | TRP | −0.41 | 8.74 |
| 1202 | GLU | PHE | −0.45 | 28.47 |
| 1202 | GLU | ALA | −0.43 | 24.3 |
| 1202 | GLU | MET | −0.42 | 17.22 |
| 1202 | GLU | LEU | −0.82 | 32.05 |
| 1202 | GLU | ARG | −1.01 | −7.58 |
| 1202 | GLU | TYR | −0.43 | 20.74 |
| 1202 | GLU | ILE | −0.45 | 41.43 |
| 1202 | GLU | GLN | −0.42 | −15.68 |
| 1202 | GLU | GLY | −0.44 | 18.98 |
| 1202 | GLU | CYS | −0.48 | 25.13 |
| 1202 | GLU | ASP | 0 | −10.67 |
| 1202 | GLU | SER | −0.43 | 24.92 |
| 1202 | GLU | LYS | −0.4 | 21.88 |
| 1202 | GLU | PRO | −0.5 | 86.02 |
| 1202 | GLU | HIE | −0.41 | 12.12 |
| 1202 | GLU | ASN | −0.44 | −14.97 |

TABLE 1-continued

Single Amino Acid Mutations in HR2

| R # | WT | MUT | Δ Aff. | Δ Stab. |
|---|---|---|---|---|
| 1202 | GLU | HIP | −0.84 | 18.29 |
| 1202 | GLU | VAL | −0.45 | 35.37 |
| 1202 | GLU | THR | −0.42 | 24.36 |
| 1202 | GLU | HID | −0.45 | 19.72 |
| 1202 | GLU | TRP | −0.42 | 8.37 |
| 1202 | GLU | PHE | −0.45 | 28.48 |
| 1202 | GLU | ALA | −0.43 | 24.3 |
| 1202 | GLU | MET | −0.42 | 17.22 |
| 1202 | GLU | LEU | −0.82 | 32.05 |
| 1202 | GLU | ARG | −1.01 | −7.58 |
| 1202 | GLU | TYR | −0.43 | 20.74 |

Example 2

Energy Maturation Studies

The HR2 structure was further engineered by introduction of several mutations based on the results of the initial residues scanning mutations as described in Example 1. (Schrodinger Suite 2020, NY, USA) The calculations included both stability and affinity options. The side chains were mutated followed by backbone minimization. Affinity maturations upon amino acids mutations was performed using Monte Carlo optimizations of maximal 2000 steps and maximal 6 deviations from the input structure. Based on the results of Δ affinity and Δ stability from the single amino acids mutations, 63 mutations were used in energy maturation studies (Table 2).

TABLE 2

The 63 Mutations Used for Energy Maturation Studies

| Mutation # | WT | Residue # | MUT |
|---|---|---|---|
| 1 | VAL | 1164 | HIS |
| 2 | VAL | 1164 | LYS |
| 3 | ASP | 1165 | CYS |
| 4 | ASP | 1165 | ILE |
| 5 | ASP | 1165 | SER |
| 6 | ASP | 1165 | GLN |
| 7 | ASP | 1165 | LYS |
| 8 | ASP | 1165 | GLY |
| 9 | ASP | 1165 | LEU |
| 10 | ASP | 1165 | ARG |
| 11 | ASP | 1165 | VAL |
| 12 | ASP | 1165 | MET |
| 13 | GLY | 1167 | ARG |
| 14 | ASP | 1168 | HIS |
| 15 | ASP | 1168 | MET |
| 16 | ASP | 1168 | ASN |
| 17 | ASP | 1168 | GLN |
| 18 | ASP | 1168 | ARG |
| 19 | SER | 1170 | HIS |
| 20 | SER | 1170 | ARG |
| 21 | ASN | 1173 | HIS |
| 77 | ASN | 1173 | LYS |
| 23 | ASN | 1173 | ARG |
| 24 | SER | 1175 | MET |
| 25 | SER | 1175 | ILE |
| 26 | SER | 1175 | ARG |
| 27 | ASN | 1178 | MET |
| 28 | ASN | 1178 | GLN |
| 29 | ASN | 1178 | ARG |
| 30 | ARG | 1184 | CYS |
| 31 | ARG | 1184 | HIS |
| 32 | ARG | 1184 | ILE |
| 33 | ARG | 1184 | VAL |
| 34 | ARG | 1184 | LYS |

TABLE 2-continued

The 63 Mutations Used for Energy Maturation Studies

| Mutation # | WT | Residue # | MUT |
|---|---|---|---|
| 35 | ARG | 1184 | THR |
| 36 | ARG | 1184 | PHE |
| 37 | ARG | 1184 | ALA |
| 38 | ARG | 1184 | MET |
| 39 | ARG | 1184 | HIS |
| 40 | ARG | 1184 | ARG |
| 41 | ARG | 1184 | TRP |
| 42 | ARG | 1184 | ASN |
| 43 | ARG | 1184 | LEU |
| 44 | ALA | 1190 | MET |
| 45 | ALA | 1190 | ARG |
| 46 | ASN | 1192 | HIS |
| 47 | ASN | 1192 | LEU |
| 48 | LEU | 1193 | MET |
| 49 | ASN | 1194 | HIS |
| 50 | ASN | 1194 | LEU |
| 51 | GLU | 1195 | ARG |
| 52 | LEU | 1197 | ARG |
| 53 | ASP | 1199 | ILE |
| 54 | ASP | 1199 | SER |
| 55 | ASP | 1199 | VAL |
| 56 | ASP | 1199 | LYS |
| 57 | ASP | 1199 | MET |
| 58 | ASP | 1199 | LEU |
| 59 | ASP | 1199 | ARG |
| 60 | ASP | 1199 | TYR |
| 61 | ASP | 1199 | HIS |

TABLE 2-continued

The 63 Mutations Used for Energy Maturation Studies

| Mutation # | WT | Residue # | MUT |
|---|---|---|---|
| 62 | GLU | 1202 | ASN |
| 63 | GLU | 1202 | ARG |

The top single amino acids mutants with the highest changes in affinity and favorable stability were combined using a Monte Carlo approach. About 320 mutant HR2 proteins were generated containing a combination of up to 6 mutant residues, compared with the wild type (Table 3). From this list, one peptide was selected with the highest affinity scores. The peptide no. 317 (termed #121) was retrieved with Δ affinity score −13.51 and a Δ stability equaling −24.88. The second peptide was no. 129 (termed #122) showed Δ affinity score −3.93 and A Stability equals −66.91. Therefore, #121 (SEQ ID NO: 2) has higher affinity than #122 but lower stability. Peptide #121 (SEQ ID NO: 2) and peptide #122 (SEQ ID NO: 3), having 5 and 6 mutations, had been selected after energy maturation step. Peptide #125 (SEQ ID NO: 5) comprises 11 amino acid mutations which were inserted into their sites by combining the top affinity changes after initial single amino acid mutations. The sequences of peptides #120 (SEQ ID NO: 1), #121 (SEQ ID NO: 2), #122 (SEQ ID NO: 3), and #125 (SEQ ID No: 5) are presented in Table 4, with the mutated residues underlined.

TABLE 3

The Results of Energy Maturation by Monte Carlo Methods for Combining Several Mutations in HR2 Structure

| MUT # | Mutations | Δ Affinity | Δ Stability |
|---|---|---|---|
| 1 | A: 1164(VAL->LYS), A: 1173(ASN->ARG), A: 1175(SER->ARG), A: 1178(ASN->ARG), A: 1184(ASP->ARG), A: 1202(GLU->ASN) | −3.15 | −90.5116 |
| 2 | A: 1164(VAL->LYS), A: 1173(ASN->ARG), A: 1175(SER->ARG), A: 1178(ASN->ARG), A: 1184(ASP->HIP), A: 1202(GLU->ASN) | −3.20835 | −86.7075 |
| 3 | A: 1164(VAL->LYS), A: 1173(ASN->ARG), A: 1175(SER->MET), A: 1178(ASN->ARG), A: 1184(ASP->ARG), A: 1202(GLU->ASN) | −2.86123 | −86.3462 |
| 4 | A: 1164(VAL->HID), A: 1173(ASN->ARG), A: 1175(SER->ARG), A: 1178(ASN->ARG), A: 1184(ASP->ARG), A: 1202(GLU->ASN) | −2.26125 | −85.0375 |
| 5 | A: 1164(VAL->LYS), A: 1173(ASN->ARG), A: 1175(SER->ARG), A: 1178(ASN->ARG), A: 1184(ASP->LEU), A: 1202(GLU->ASN) | −3.14849 | −84.3989 |
| 6 | A: 1164(VAL->LYS), A: 1173(ASN->ARG), A: 1175(SER->ARG), A: 1178(ASN->ARG), A: 1184(ASP->MET), A: 1202(GLU->ASN) | −3.13824 | −84.3851 |
| 7 | A: 1164(VAL->LYS), A: 1173(ASN->ARG), A: 1175(SER->ARG), A: 1178(ASN->ARG), A: 1184(ASP->ILE), A: 1202(GLU->ASN) | −3.11404 | −83.5476 |
| 8 | A: 1164(VAL->LYS), A: 1173(ASN->ARG), A: 1175(SER->MET), A: 1178(ASN->ARG), A: 1184(ASP->HIP), A: 1202(GLU->ASN) | −2.92024 | −82.5475 |
| 9 | A: 1164(VAL->LYS), A: 1173(ASN->ARG), A: 1175(SER->ILE), A: 1178(ASN->ARG), A: 1184(ASP->ARG), A: 1202(GLU->ASN) | −2.63282 | −82.2024 |
| 10 | A: 1164(VAL->LYS), A: 1173(ASN->ARG), A: 1175(SER->MET), A: 1178(ASN->ARG), A: 1184(ASP->LEU), A: 1202(GLU->ASN) | −2.82403 | −81.444 |
| 11 | A: 1164(VAL->HID), A: 1173(ASN->ARG), A: 1175(SER->MET), A: 1178(ASN->ARG), A: 1184(ASP->ARG), A: 1202(GLU->ASN) | −1.97265 | −80.712 |
| 12 | A: 1164(VAL->LYS), A: 1175(SER->ARG), A: 1178(ASN->ARG), A: 1184(ASP->ARG), A: 1202(GLU->ASN) | −2.41396 | −80.6946 |
| 13 | A: 1164(VAL->LYS), A: 1173(ASN->ARG), A: 1175(SER->ARG), A: 1178(ASN->ARG), A: 1184(ASP->VAL), A: 1202(GLU->ASN) | −3.13885 | −80.4482 |
| 14 | A: 1164(VAL->LYS), A: 1173(ASN->ARG), A: 1175(SER->MET), A: 1178(ASN->ARG), A: 1184(ASP->MET), A: 1202(GLU->ASN) | −2.87162 | −80.2281 |
| 15 | A: 1164(VAL->LYS), A: 1173(ASN->ARG), A: 1175(SER->ARG), A: 1178(ASN->ARG), A: 1184(ASP->THR), A: 1202(GLU->ASN) | −3.16949 | −79.9326 |
| 16 | A: 1164(VAL->LYS), A: 1173(ASN->ARG), A: 1175(SER->ARG), A: 1178(ASN->ARG), A: 1184(ASP->ARG), A: 1190(ALA->MET) | −2.9837 | −79.8882 |
| 17 | A: 1164(VAL->LYS), A: 1173(ASN->ARG), A: 1175(SER->ARG), A: 1178(ASN->ARG), A: 1184(ASP->HIE), A: 1202(GLU->ASN) | −3.16017 | −79.5818 |
| 18 | A: 1164(VAL->LYS), A: 1173(ASN->ARG), A: 1175(SER->ARG), A: 1178(ASN->ARG), A: 1184(ASP->LYS), A: 1202(GLU->ASN) | −3.20243 | −79.5381 |
| 19 | A: 1164(VAL->LYS), A: 1173(ASP->ARG), A: 1175(SER->ARG), A: 1178(ASN->ARG), A: 1184(ASP->HIP), A: 1190(ALA->MET) | −2.97014 | −79.3551 |

TABLE 3-continued

The Results of Energy Maturation by Monte Carlo Methods for Combining Several Mutations in HR2 Structure

| MUT # | Mutations | Δ Affinity | Δ Stability |
|---|---|---|---|
| 20 | A: 1164(VAL->LYS), A: 1173(ASN->ARG), A: 1175(SER->MET), A: 1178(ASN->ARG), A: 1184(ASP->ILE), A: 1202(GLU->ASN) | −2.82606 | −79.2243 |
| 21 | A: 1164(VAL->HID), A: 1173(ASN->ARG), A: 1175(SER->ARG), A: 1178(ASN->ARG), A: 1184(ASP->MET), A: 1202(GLU->ASN) | −2.25031 | −78.9106 |
| 22 | A: 1164(VAL->LYS), A: 1173(ASN->ARG), A: 1175(SER->ARG), A: 1184(ASP->ARG), A: 1202(GLU->ASN) | −2.92139 | −78.5547 |
| 23 | A: 1164(VAL->LYS), A: 1173(ASN->ARG), A: 1175(SER->ILE), A: 1178(ASN->ARG), A: 1184(ASP->HIP), A: 1202(GLU->ASN) | −2.69119 | −78.3961 |
| 24 | A: 1164(VAL->LYS), A: 1173(ASN->ARG), A: 1175(SER->ILE), A: 1178(ASN->ARG), A: 1184(ASP->LEU), A: 1202(GLU->ASN) | −2.59426 | −77.2938 |
| 25 | A: 1164(VAL->LYS), A: 1173(ASN->ARG), A: 1175(SER->ARG), A: 1178(ASN->ARG), A: 1184(ASP->MET), A: 1190(ALA->MET) | −2.93001 | −77.1471 |
| 26 | A: 1164(VAL->HID), A: 1173(ASN->ARG), A: 1175(SER->MET), A: 1178(ASN->ARG), A: 1184(ASP->HIP), A: 1202(GLU->ASN) | −2.03167 | −76.9135 |
| 27 | A: 1164(VAL->HID), A: 1173(ASN->ARG), A: 1175(SER->ILE), A: 1178(ASN->ARG), A: 1184(ASP->ARG), A: 1202(GLU->ASN) | −1.74416 | −76.5694 |
| 28 | A: 1164(VAL->LYS), A: 1173(ASN->ARG), A: 1175(SER->ARG), A: 1178(ASN->ARG), A: 1184(ASP->ASN), A: 1202(GLU->ASN) | −3.13567 | −76.5467 |
| 29 | A: 1164(VAL->HID), A: 1173(ASN->ARG), A: 1175(SER->ARG), A: 1178(ASN->ARG), A: 1184(ASP->HIP), A: 1202(GLU->ASN) | −2.31438 | −76.4215 |
| 30 | A: 1164(VAL->LYS), A: 1173(ASN->ARG), A: 1175(SER->ARG), A: 1178(ASN->ARG), A: 1184(ASP->ALA), A: 1202(GLU->ASN) | −3.12762 | −76.3308 |
| 31 | A: 1164(VAL->LYS), A: 1173(ASN->ARG), A: 1175(SER->MET), A: 1178(ASN->ARG), A: 1184(ASP->VAL), A: 1202(GLU->ASN) | −2.85122 | −76.1498 |
| 32 | A: 1164(VAL->LYS), A: 1173(ASN->ARG), A: 1175(SER->ARG), A: 1178(ASN->ARG), A: 1184(ASP->ILE), A: 1190(ALA->MET) | −2.87705 | −76.0657 |
| 33 | A: 1164(VAL->LYS), A: 1173(ASN->ARG), A: 1175(SER->ARG), A: 1178(ASN->ARG), A: 1184(ASP->ARG) | −2.72771 | −76.0509 |
| 34 | A: 1164(VAL->LYS), A: 1173(ASN->ARG), A: 1175(SER->ILE), A: 1178(ASN->ARG), A: 1184(ASP->MET), A: 1202(GLU->ASN) | −2.62087 | −75.9333 |
| 35 | A: 1164(VAL->HID), A: 11.73(ASN->ARG), A: 1175(SER->MET), A: 1178(ASN->ARG), A: 1184(ASP->LEU), A: 1202(GLU->ASN) | −1.93485 | −75.8089 |
| 36 | A: 1164(VAL->LYS), A: 1173(ASN->ARG), A: 1175(SER->MET), A: 1178(ASN->ARG), A: 1184(ASP->ARG), A: 1190(ALA->MET) | −2.69484 | −75.7216 |
| 37 | A: 1164(VAL->LYS), A: 1173(ASN->ARG), A: 1175(SER->MET), A: 1178(ASN->ARG), A: 1184(ASP->THR), A: 1202(GLU->ASN) | −2.88096 | −75.6159 |
| 38 | A: 1164(VAL->HID), A: 1173(ASN->ARG), A: 1175(SER->ARG), A: 1178(ASN->ARG), A: 1184(ASP->LEU), A: 1202(GLU->ASN) | −2.22244 | −75.6088 |
| 39 | A: 1164(VAL->LYS), A: 1173(ASN->ARG), A: 1175(SER->MET), A: 1178(ASN->ARG), A: 1184(ASP->LYS), A: 1202(GLU->ASN) | −2.91395 | −75.3534 |
| 40 | A: 1164(VAL->LYS), A: 1175(SER->MET), A: 1178(ASN->ARG), A: 1184(ASP->ARG), A: 1202(GLU->ASN) | −2.13032 | −75.31 |
| 41 | A: 1164(VAL->LYS), A: 1173(ASN->ARG), A: 1175(SER->MET), A: 1178(ASN->ARG), A: 1184(ASP->HIE), A: 1202(GLU->ASN) | −2.87163 | −75.2573 |
| 42 | A: 1164(VAL->LYS), A: 1173(ASN->ARG), A: 1175(SER->MET), A: 1178(ASN->ARG), A: 1184(ASP->HIP), A: 1190(ALA->MET) | −2.67835 | −75.14 |
| 43 | A: 1164(VAL->LYS), A: 1173(ASN->ARG), A: 1175(SER->ILE), A: 1178(ASN->ARG), A: 1184(ASP->ILE), A: 1202(GLU->ASN) | −2.59772 | −75.0713 |
| 44 | A: 1164(VAL->LYS), A: 1173(ASN->ARG), A: 1175(SER->ARG), A: 1178(ASN->ARG), A: 1184(ASP->ARG), A: 1199(ASP->VAL) | −3.16938 | −75.0555 |
| 45 | A: 1164(VAL->HID), A: 1175(SER->ARG), A: 1178(ASN->ARG), A: 1184(ASP->ARG), A: 1202(GLU->ASN) | −1.52503 | −75.0103 |
| 46 | A: 1164(VAL->HID), A: 1173(ASN->ARG), A: 1175(SER->MET), A: 1178(ASN->ARG), A: 1184(ASP->MET), A: 1202(GLU->ASN) | −1.98351 | −74.5899 |
| 47 | A: 1164(VAL->HID), A: 1173(ASN->ARG), A: 1175(SER->ARG), A: 1178(ASN->ARG), A: 1184(ASP->ARG), A: 1190(ALA->MET) | −2.0849 | −74.4922 |
| 48 | A: 1164(VAL->HID), A: 1173(ASN->ARG), A: 1175(SER->ARG), A: 1178(ASN->ARG), A: 1184(ASP->THR), A: 1202(GLU->ASN) | −2.27884 | −74.4681 |
| 49 | A: 1164(VAL->LYS), A: 1175(SER->ARG), A: 1178(ASN->ARG) A: H84(ASP->MET), A: 1202(GLU->ASN) | −2.40213 | −74.4269 |
| 50 | A: 1164(VAL->HID), A: 1173(ASN->ARG), A: 1175(SER->ARG), A: 1178(ASN->ARG), A: 1184(ASP->HIE), A: 1202(GLU->ASN) | −2.26962 | −74.1192 |
| 51 | A: 1164(VAL->HID), A: 1173(ASN->ARG), A: 1175(SER->ARG), A: 1178(ASN->ARG), A: 1184(ASP->LYS), A: 1202(GLU->ASN) | −2.28673 | −74, 0204 |
| 52 | A: 1164(VAL->LYS), A: 1173(ASN->ARG), A: 1175(SER->MET), A: 1178(ASN->ARG), A: 1184(ASP->LEU), A: 1190(ALA->MET) | −2.58518 | −73.9703 |
| 53 | A: 1164(VAL->HID), A: 1173(ASN->ARG), A: 1175(SER->ARG), A: 1178(ASN->ARG), A: 1184(ASP->HIP), A: 1190(ALA->MET) | −2.07138 | −73.961 |
| 54 | A: 1164(VAL->LYS), A: 1173(ASN->ARG), A: 1175(SER->MET), A: 1184(ASP->ARG), A: 1202(GLU->ASN) | −2.64144 | −73.8811 |
| 55 | A: 1164(VAL->HID), A: 1173(ASN->ARG), A: 1175(SER->MET), A: 1178(ASN->ARG), A: 1184(ASP->ILE), A: 1202(GLU->ASN) | −1.93729 | −73.5944 |
| 56 | A: 1164(VAL->LYS), A: 1173(ASN->ARG), A: 1175(SER->ARG), A: 1178(ASN->ARG), A: 1184(ASP->VAL), A: 1190(ASA->MET) | −2.90375 | −73.0497 |

TABLE 3-continued

The Results of Energy Maturation by Monte Carlo Methods for Combining Several Mutations in HR2 Structure

| MUT # | Mutations | Δ Affinity | Δ Stability |
|---|---|---|---|
| 57 | A: 1164(VAL->MHP), A: 1173(ASN->ARG), A: 1175(SER->ARG), A: 1184(ASP->ARG), A: 1202(GLU->ASN) | −2.03164 | −73.0418 |
| 58 | A: 1164(VAL->LYS), A: 1173(ASN->ARG), A: 1175(SER->MET), A: 1178(ASN->ARG), A: 1184(ASP->MET), A: 1190(ALA->MET) | −2.63835 | −72.757 |
| 59 | A: 1164(VAL->LYS), A: 1175(SER->ILE), A: 1178(ASN->ARG), A: 1184(ASP->ARG), A: 1202(GLU->ASN) | −1.87427 | −72.6957 |
| 60 | A: 1164(VAL->LYS), A: 1173(ASN->ARG), A: 1175(SER->ARG), A: 1178(ASN->ARG), A: 1184(ASP->PHE), A: 1202(GLU->ASN) | −3.16475 | −72.6793 |
| 61 | A: 1164(VAL->LYS), A: 1173(ASN->ARG), A: 1175(SER->MET), A: 1178(ASN->ARG), A: 1184(ASP->CYS), A: 1202(GLU->ASN) | −2.8657 | −72.465 |
| 62 | A: 1164(VAL->LYS), A: 1173(ASN->ARG), A: 1175(SER->ARG), A: 1178(ASN->ARG), A: 1184(ASP->THR), A: 1190(ALA->MET) | −2.93048 | −72.4396 |
| 63 | A: 1164(VAL->LYS), A: 1173(ASN->ARG), A: 1175(SER->MET), A: 1178(ASN->ARG), A: 1184(ASP->ASN), A: 1202(GLU->ASN) | −2.85352 | −72.24 |
| 64 | A: 1164(VAL->LYS), A: 1173(ASN->ARG), A: 1175(SER->ARG), A: 1184(ASP->MET), A: 1202(GLU->ASN) | −2.90996 | −72.205 |
| 65 | A: 1164(VAL->LYS), A: 1173(ASN->ARG), A: 1175(SER->ARG), A: 1178(ASN->ARG), A: 1184(ASP->CYS), A: 1202(GLU->ASN) | −3.1514 | −72.1371 |
| 66 | A: 1164(VAL->LYS), A: 1173(ASN->ARG), A: 1175(SER->MET), A: 1178(ASN->ARG), A: 1184(ASP->ALA), A: 1202(GLU->ASN) | −2.83939 | −72.0255 |
| 67 | A: 1164(VAL->LYS), A: 1173(ASN->ARG), A: 1175(SER->ILE), A: 1178(ASN->ARG), A: 1184(ASP->VAL), A: 1202(GLU->ASN) | −2.62152 | −72.0013 |
| 68 | A: 1164(VAL->LYS), A: 1173(ASN->ARG), A: 1175(SER->MET), A: 1178(ASN->ARG), A: 1184(ASP->ARG) | −2.43883 | −71.8836 |
| 69 | A: 1164(VAL->LYS), A: 1173(ASN->ARG), A: 1175(SER->MET), A: 1178(ASN->ARG), A: 1184(ASP->HIP), A: 1199(ASP->VAL) | −2.9478 | −71.8725 |
| 70 | A: 1164(VAL->LYS), A: 1173(ASN->ARG), A: 1175(SER->MET), A: 1178(ASN->ARG), A: 1184(ASP->ILE), A: 1190(ALA->MET) | −2.58851 | −71.7534 |
| 71 | A: 1164(VAL->HID), A: 1173(ASN->ARG), A: 1175(SER->ARG), A: 1178(ASN->ARG), A: 1184(ASP->MET), A: 1190(ALA->MET) | −2.03125 | −71.7529 |
| 72 | A: 1164(VAL->LYS), A: 1173(ASN->ARG), A: 1175(SER->ARG), A: 1178(ASN->ARG), A: 1184(ASP->HIP) | −2.78057 | −71.7522 |
| 73 | A: 1164(VAL->LYS), A: 1173(ASN->ARG), A: 1175(SER->ILE), A: 1178(ASN->ARG), A: 1184(ASP->ARG), A: 1190(ALA->MET) | −2.47592 | −71.6783 |
| 74 | A: 1164(VAL->LYS), A: 1174(SER->MET), A: 1178(ASN->ARG), A: 1184(ASP->HIP), A: 1202(GLU->ASN) | −2.1891 | −71.5334 |
| 75 | A: 1164(VAL->LYS), A: 1175(SER->ARG), A: 1178(ASN->ARG), A: 1184(ASP->HIP), A: 1202(GLU->ASN) | −2.47533 | −71.5042 |
| 76 | A: 1164(VAL->LYS), A: 1173(ASN->ARG), A: 1175(SER->ILE), A: 1178(ASN->ARG), A: 1184(ASP->THR), A: 1202(GLU->ASN) | −2.65276 | −71.4651 |
| 77 | A: 1164(VAL->HID), A: 1173(ASN->ARG), A: 1175(SER->ARG), A: 1178(ASN->ARG), A: 1184(ASP->CYS), A: 1202(GLU->ASN) | −2.26304 | −71.3236 |
| 78 | A: 1164(VAL->LYS), A: 1173(ASN->ARG), A: 1175(SER->ARG), A: 1178(ASN->ARG), A: 1184(ASP->HIP), A: 1199(ASP->VAL) | −0.516825 | −71.3124 |
| 79 | A: 1164(VAL->LYS), A: 1173(ASN->ARG), A: 1175(SER->ILE), A: 1178(ASN->ARG), A: 1184(ASP->LYS), A: 1202(GLU->ASN) | −2.6856 | −71.2206 |
| 80 | A: 1164(VAL->LYS), A: 1173(ASN->ARG), A: 1175(SER->ILE), A: 1178(ASN->ARG), A: 1184(ASP->HIP), A: 1190(ALA->MET) | −2.46309 | −71.1379 |
| 81 | A: 1164(VAL->LYS), A: 1173(ASN->ARG), A: 1175(SER->MET), A: 1178(ASN->ARG), A: 1184(ASP->TRP), A: 1202(GLU->ASN) | −2.87288 | −70.6398 |
| 82 | A: 1164(VAL->HID), A: 1173(ASN->ARG), A: 1175(SER->ARG), A: 1178(ASN->ARG), A: 1184(ASP->ARG) | −1.83906 | −70.5481 |
| 83 | A: 1164(VAL->HID), A: 1173(ASN->ARG), A: 1175(SER->MET), A: 1178(ASN->ARG), A: 1184(ASP->VAL), A: 1202(GLU->ASN) | −1.96153 | −70.5143 |
| 84 | A: 1164(VAL->LYS), A: 1175(SER->ARG), A: 1178(ASN->ARG), A: 1184(ASP->LEU), A: 1202(GLU->ASN) | −2.3792 | −70.491 |
| 85 | A: 1164(VAL->LYS), A: 1173(ASN->ARG), A: 1175(SER->ARG), A: 1178(ASN->ARG), A: 1184(ASP->TRP), A: 1202(GLU->ASN) | −3.18508 | −70.3237 |
| 86 | A: 1164(VAL->LYS), A: 1175(SER->MET), A: 1178(ASN->ARG), A: 1184(ASP->LEU), A: 1202(GLU->ASN) | −2.09248 | −70.3027 |
| 87 | A: 1164(VAL->LYS), A: 1175(SER->ARG), A: 1178(ASN->ARG), A: 1184(ASP->ARG), A: 1190(ALA->MET) | −2.25074 | −70.264 |
| 88 | A: 1164(VAL->HID), A: 1173(ASN->ARG), A: 1175(SER->ARG), A: 1178(ASN->ARG), A: 1184(ASP->VAL), A: 1202(GLU->ASN) | −2.24818 | −70.2603 |
| 89 | A: 1164(VAL->HID), A: 1173(ASN->ARG), A: 1175(SER->MET), A: 1178(ASN->ARG), A: 1184(ASP->ARG), A: 1190(ALA->MET) | −1.79539 | −70.1623 |
| 90 | A: 1164(VAL->LYS), A: 1173(ASN->ARG), A: 1175(SER->MET), A: 1184(ASP->HIP), A: 1202(GLU->ASN) | −2.69125 | −70.0385 |
| 91 | A: 1164(VAL->LYS), A: 1173(ASN->ARG), A: 1175(SER->ILE), A: 1184(ASP->ARG), A: 1202(GLU->ASN) | −2.40499 | −70.0128 |
| 92 | A: 1164(VAL->LYS), A: 1173(ASN->ARG), A: 1175(SER->ARG), A: 1184(ASP->HIP), A: 1202(GLU->ASN) | −2.97927 | −70.0001 |
| 93 | A: 1164(VAL->HID), A: 1173(ASN->ARG), A: 1175(SER->MET), A: 1178(ASN->ARG), A: 1184(ASP->THR), A: 1202(GLU->ASN) | −1.99143 | −69.9823 |

TABLE 3-continued

The Results of Energy Maturation by Monte Carlo Methods for Combining Several Mutations in HR2 Structure

| MUT # | Mutations | Δ Affinity | Δ Stability |
|---|---|---|---|
| 94 | A: 1164(VAL−>LYS), A: 1173(ASN−>ARG), A: 1175(SER−>ARG), A: 1178(ASN−>ARG), A: 1184(ASP−>MET) | −2.71599 | −69.806 |
| 95 | A: 1164(VAL−>LYS), A: 1175(SER−>ARG), A: 1178(ASN−>ARG), A: 1184(ASP−>HIP), A: 1190(ALA−>MET) | −2.23843 | −69.7272 |
| 96 | A: 1164(VAL−>HID), A: 1173(ASN−>ARG), A: 1175(SER−>MET), A: 1178(ASN−>ARG), A: 1184(ASP−>HIP), A: 1190(ALA−>MET) | −1.77931 | −69.5775 |
| 97 | A: 1164(VAL−>LYS), A: 1173(ASN−>ARG), A: 1175(SER−>MET), A: 1178(ASN−>ARG), A: 1184(ASP−>LEU), A: 1199(ASP−>VAL) | −2.89081 | −69.4973 |
| 98 | A: 1164(VAL−>HID), A: 1173(ASN−>ARG), A: 1175(SER−>ARG), A: 1178(ASN−>ARG), A: 1184(ASP−>TRP), A: 1202(GLU−>ASN) | −2.26314 | −69.4945 |
| 99 | A: 1164(VAL−>HID), A: 1175(SER−>MET), A: 1178(ASN−>ARG), A: 1184(ASP−>ARG), A: 1202(GLU−>ASN) | −1.24082 | −69.4942 |
| 100 | A: 1164(VAL−>LYS), A: 1173(ASN−>ARG), A: 1175(SER−>ARG), A: 1178(ASN−>ARG), A: 1184(ASP−>LEU), A: 1199(ASP−>VAL) | −3.17673 | −69.1654 |
| 101 | A: 1164(VAL−>LYS), A: 1175(SER−>MET), A: 1178(ASN−>ARG), A: 1184(ASP−>MET), A: 1202(GLU−>ASN) | −2.14073 | −69.0781 |
| 102 | A: 1164(VAL−>LYS), A: 1173(ASN−>ARG), A: 1175(SER−>ARG), A: 1178(ASN−>ARG), A: 1184(ASP−>ALA), A: 1190(ALA−>MET) | −2.89142 | −68.8574 |
| 103 | A: 1164(VAL−>HID), A: 1175(SER−>ARG), A: 1178(ASN−>ARG), A: 1184(ASP−>MET), A: 1202(GLU−>ASN) | −1.51398 | −68.7879 |
| 104 | A: 1164(VAL−>LYS), A: 1173(ASN−>ARG), A: 1175(SER−>ARG), A: 1184(ASP−>LEU), A: 1202(GLU−>ASN) | −2.87331 | −68.7805 |
| 105 | A: 1164(VAL−>LYS), A: 1173(ASN−>ARG), A: 1175(SER−>ILE), A: 1178(ASN−>ARG), A: 1184(ASP−>MET), A: 1190(ALA−>MET) | −2.42088 | −68.7319 |
| 106 | A: 1164(VAL−>LYS), A: 1173(ASN−>ARG), A: 1175(SER−>MET), A: 1178(ASN−>ARG), A: 1184(ASP−>VAL), A: 1190(ALA−>MET) | −2.61056 | −68.656 |
| 107 | A: 1164(VAL−>LYS), A: 1173(ASN−>ARG), A: 1175(SER−>MET), A: 1184(ASP−>LEU), A: 1202(GLU−>ASN) | −2.59308 | −68.5377 |
| 108 | A: 1164(VAL−>LYS), A: 1173(ASN−>ARG), A: 1175(SER−>MET), A: 1178(ASN−>ARG), A: 1184(ASP−>PHE), A: 1202(GLU−>ASN) | −2.87633 | −68.3844 |
| 109 | A: 1164(VAL−>HID), A: 1173(ASN−>ARG), A: 1175(SER−>MET), A: 1184(ASP−>ARG), A: 1202(GLU−>ASN) | −1.75278 | −68.2442 |
| 110 | A: 1164(VAL−>LYS), A: 1173(ASN−>ARG), A: 1175(SER−>MET), A: 1178(ASN−>ARG), A: 1184(ASP−>THR), A: 1190(ALA−>MET) | −2.64184 | −68.1336 |
| 111 | A: 1164(VAL−>LYS), A: 1173(ASN−>ARG), A: 1175(SER−>ILE), A: 1178(ASN−>ARG), A: 1184(ASP−>ASN), A: 1202(GLU−>ASN) | −2.62486 | −68.0901 |
| 112 | A: 1164(VAL−>LYS), A: 1175(SER−>MET), A: 1178(ASN−>ARG), A: 1184(ASP−>ILE), A: 1202(GLU−>ASN) | −2.09451 | −68.0828 |
| 113 | A: 1164(VAL−>LYS), A: 1173(ASN−>ARG), A: 1175(SER−>MET), A: 1178(ASN−>ARG), A: 1184(ASP−>HIP) | _?498?5 | −68.0702 |
| 114 | A: 1164(VAL−>LYS), A: 1173(ASN−>ARG), A: 1175(SER−>ARG), A: 1184(ASP−>ARG), A: 1190(ALA−>MET) | −274988 | −68.0679 |
| 115 | A: 1164(VAL−>LYS), A: 1173(ASN−>ARG), A: 1175(SER−>MET), A: 1178(ASN−>ARG), A: 1184(ASP−>LYS), A: 1190(ALA−>MET) | −2.67546 | −67.9832 |
| 116 | A: 1164(VAL−>LYS), A: 1173(ASN−>ARG), A: 1175(SER−>MET), A: 1178(ASN−>ARG), A: 1184(ASP−>HIE), A: 1190(ALA−>MET) | −2.63539 | −67.8022 |
| 117 | A: 1164(VAL−>LYS), A: 1173(ASN−>ARG), A: 1175(SER−>ILE), A: 1178(ASN−>ARG), A: 1184(ASP−>ARG) | −2.21033 | −67.7376 |
| 118 | A: 1164(VAL−>LYS), A: 1173(ASN−>ARG), A: 1175(SER−>ILE), A: 1178(ASN−>ARG), A: 1184(ASP−>ILE), A: 1190(ALA−>MET) | −2.36989 | −67.7095 |
| 119 | A: 1164(VAL−>LYS), A: 1173(ASN−>ARG), A: 1175(SER−>ARG), A: 1178(ASN−>ARG), A: 1184(ASP−>TRP), A: 1190(ALA−>MET) | −2.95321 | −67.5733 |
| 120 | A: 1164(VAL−>LYS), A: 1173(ASN−>ARG), A: 1175(SER−>ARG), A: 1178(ASN−>ARG), A: 1184(ASP−>HIE), A: 1190(ALA−>MET) | −2.92368 | −67.4455 |
| 121 | A: 1164(VAL−>LYS), A: 1173(ASN−>ARG), A: 1175(SER−>ARG), A: 1178(ASN−>ARG), A: 1184(ASP−>LYS), A: 1190(ALA−>MET) | −2.92977 | −67.4121 |
| 122 | A: 1164(VAL−>LYS), A: 1175(SER−>ARG), A: 1178(ASN−>ARG), A: 1184(ASP−>MET), A: 1190(ALA−>MET) | −2.19916 | −67.4095 |
| 123 | A: 1164(VAL−>LYS), A: 1173(ASX−>ARG), A: 1175(SER−>ARG), A: 1184(ASP−>HIP), A: 1190(ALA−>MET) | −2.73459 | −67.3546 |
| 124 | A: 1164(VAL−>HID), A: 1173(ASN−>ARG), A: 1175(SER−>MET), A: 1178(ASN−>ARG), A: 1184(ASP−>MET), A: 1190(ALA−>MET) | −1.73996 | −67.2204 |
| 125 | A: 1164(VAL−>HID), A: 1173(ASN−>ARG), A: 1175(SER−>ARG), A: 1178(ASN−>ARG), A: 1184(ASP−>PHE), A: 1202(GLU−>ASN) | −2.27028 | −67.1836 |
| 126 | A: 1164(VAL−>HID), A: 1165(ASP−>ARG), A: 1173(ASN−>ARG), A: 1175(SER−>MET), A: 1178(ASN−>ARG), A: 1184(ASP−>MET) | −3.09006 | −66.9395 |
| 127 | A: 1164(VAL−>LYS), A: 1165(ASP−>ARG), A: 1173(ASN−>ARG), A: 1175(SER−>MET), A: 1178(ASN−>ARG), A: 1184(ASP−>MET) | −3.928 | −66.9124 |
| 128 | A: 1164(VAL−>LYS), A: 1173(ASN−>ARG), A: 1175(SER−>MET), A: 1178(ASN−>ARG), A: 1184(ASP−>LEU) | −2.40174 | −66.8723 |
| 129 | A: 1164(VAL−>LYS), A: 1165(ASP−>MET), A: 1173(ASN−>ARG), A: 1175(SER−>ARG), A: 1178(ASN−>ARG), A: 1184(ASP−>HIP) | −3.5736 | −66.7995 |
| 130 | A: 1164(VAL−>HID), A: 1173(ASN−>ARG), A: 1175(SER−>MET), A: 1178(ASN−>ARG), A: 1184(ASP−>ALA), A: 1202(GLU−>ASN) | −1.95052 | −66.3943 |

TABLE 3-continued

The Results of Energy Maturation by Monte Carlo Methods for Combining Several Mutations in HR2 Structure

| MUT # | Mutations | Δ Affinity | Δ Stability |
|---|---|---|---|
| 131 | A: 1164(VAL->LYS), A: 1173(ASN->ARG), A: 1175(SER->MET), A: 1184(ASP->ILE), A: 1202(GLU->ASN) | −2.59701 | −66.3285 |
| 132 | A: 1164(VAL->HID), A: 1173(ASN->ARG), A: 1175(SER->MET), A: 1178(ASN->ARG), A: 1184(ASP->ARG) | −1.55026 | −66.2486 |
| 133 | A: 1164(VAL->HID), A: 1173(ASN->ARG), A: 1175(SER->MET), A: 1178(ASN->ARG), A: 1184(ASP->HIP), A: 1199(ASP->VAL) | −2.05838 | −66.2385 |
| 134 | A: 1164(VAL->HID), A: 1173(ASN->ARG), A: 1175(SER->MET), A: 1178(ASN->ARG), A: 1184(ASP->ILE), A: 1190(ALA->MET) | −1.68924 | −66.1946 |
| 135 | A: 1164(VAL->HID), A: 1173(ASN->ARG), A: 1175(SER->ARG), A: 1178(ASN->ARG), A: 1184(ASP->ALA), A: 1202(GLU->ASN) | −2.23545 | −66.1903 |
| 136 | A: 1164(VAL->LYS), A: 1165(ASP->SER), A: 1173(ASN->ARG), A: 1175(SER->MET), A: 1178(ASN->ARG), A: 1184(ASP->LEU) | −3.14599 | −65.5882 |
| 137 | A: 1164(VAL->HID), A: 1173(ASN->ARG), A: 1175(SER->ILE), A: 1178(ASN->ARG), A: 1184(ASP->HIP), A: 1190(ALA->MET) | −1.56168 | −65.5328 |
| 138 | A: 1164(VAL->HID), A: 1165(ASP->SER), A: 1173(ASN->ARG), A: 1175(SER->MET), A: 1178(ASN->ARG), A: 1184(ASP->LEU) | −2.29549 | −65.4798 |
| 139 | A: 1164(VAL->LYS), A: 1173(ASN->ARG), A: 1175(SER->ILE), A: 1178(ASN->ARG), A: 1184(ASP->LEU), A: 1199(ASP->VAL) | −2.66177 | −65.3458 |
| 140 | A: 1164(VAL->LYS), A: 1173(ASN->ARG), A: 1175(SER->MET), A: 1178(ASN->ARG), A: 1184(ASP->ASN), A: 1190(ALA->MET) | −2.61782 | −65.2462 |
| 141 | A: 1164(VAL->LYS), A: 1173(ASN->ARG), A: 1175(SER->MET), A: 1178(ASN->ARG), A: 1184(ASP->MET) | −2.446 | −65.1794 |
| 142 | A: 1164(VAL->LYS), A: 1173(ASN->ARG), A: 1175(SER->ARG), A: 1178(ASN->ARG), A: 1184(ASP->LEU) | −2.72561 | −65.1716 |
| 143 | A: 1164(VAL->LYS), A: 1173(ASN->ARG), A: 1175(SER->ARG), A: 1178(ASN->ARG), A: 1184(ASP->VAL), A: 1199(ASP->VAL) | −3.15618 | −65.1475 |
| 144 | A: 1164(VAL->LYS), A: 1175(SER->MET), A: 1178(ASN->ARG), A: 1184(ASP->ARG), A: 1190(ALA->MET), | −1.96398 | −64.9665 |
| 145 | A: 1164(VAL->LYS), A: 1173(ASN->ARG), A: 1175(SER->MET), A: 1178(ASN->ARG), A: 1184(ASP->CYS), A: 1190(ALA->MET) | −2.62551 | −64.964 |
| 146 | A: 1164(VAL->LYS), A: 1173(ASN->ARG), A: 1175(SER->ARG), A: 1184(ASP->MET), A: 1190(ALA->MET) | −2.7056 | −64.9267 |
| 147 | A: 1164(VAL->LYS), A: 1173(ASN->ARG), A: 1175(SER->ARG), A: 1178(ASN->ARG), A: 1184(ASP->ASN), A: 1190(ALA->MET) | −2.90685 | −64.9043 |
| 148 | A: 1164(VAL->LYS), A: 1173(ASN->ARG), A: 1175(SER->MET), A: 1178(ASN->ARG), A: 1184(ASP->HIE), A: 1199(ASP->VAL) | −2.90094 | −64.6852 |
| 149 | A: 1164(VAL->LYS), A: 1173(ASN->ARG), A: 1175(SER->MET), A: 1178(ASN->ARG), A: 1184(ASP->ILE) | −2.40386 | −64.6453 |
| 150 | A: 1164(VAL->LYS), A: 1173(ASN->ARG), A: 1175(SER->ARG), A: 1178(ASN->ARG), A: 1184(ASP->CYA), A: 1190(ALA->MET) | −2.91451 | −64.6249 |
| 151 | A: 1164(VAL->LYS), A: 1175(SER->ARG), A: 1178(ASN->ARG), A: 1184(ASP->ARG), A: 1199(ASP->VAL) | −2.4356 | −64.5724 |
| 152 | A: 1164(VAL->LYS), A: 1173(ASN->ARG), A:1175(SER->MET), A: 1178(ASN->ARG), A: 1184(ASP->ALA), A: 1190(ALA->MET) | −2.60191 | −64.5258 |
| 153 | A: 1164(VAL->LYS), A: 1175(SER->MET), A: 1178(ASN->ARG), A: 1184(ASP->THR), A: 1202(GLU->ASN) | −2.14927 | −64.4745 |
| 154 | A: 1164(VAL->LYS), A: 1175(SER->ARG), A: 1178(ASN->ARG), A: 1184(ASP->LYS), A: 1202(GLU->ASN) | −2.46702 | −64.3537 |
| 155 | A: 1164(VAL->LYS), A: 1173(ASN->ARG), A: 1175(SER->ARG), A: 1178(ASN->ARG), A: 1184(ASP->HIE), A: 1199(ASP->VAL) | −3.18554 | −64.3519 |
| 156 | A: 1164(VAL->LYS), A: 1178(ASN->ARG), A: 1184(ASP->ARG), A: 1190(ALA->MET), A: l194(ASN->LEU), A: 1199(ASP->HIE) | −1.9736 | −64.3502 |
| 157 | A: 1164(VAL->HID), A: 1173(ASN->ARG), A: 1175(SER->ARG), A: 1178(ASN->ARG), A: 1184(ASP->MED. | −1.82802 | −64.3376 |
| 158 | A: 1164(VAL->LYS), A: 1175(SER->MET), A: 1178(ASN->ARG), A: 1184(ASP->HIP), A: 1190(ALA->MET) | −1.94693 | −64.3347 |
| 159 | A: 1164(VAL->LYS), A: 1173(ASN->ARG), A: 1175(SER->ILE), A: 1178(ASN->ARG), A: 1184(ASP->PHE), A: 1202(GLU->ASN) | −2.64384 | −64.2248 |
| 160 | A: 1164(VAL->HID), A: 1175(SER->ARG), A: 1178(ASN->ARG), A: 1184(ASP->LYS), A: 1202(GLU->ASN) | −1.57318 | −64.0203 |
| 161 | A: 1164(VAL->LYS), A: 1175(SER->ILE), A: 1178(ASN->ARG), A: 1184(ASP->ARG), A: 1190(ALA->MET), A: 1194(ASN->HIP) | −2.29523 | −63.9817 |
| 162 | A: 1164(VAL->HID), A: 1173(ASN->ARG), A: 1175(SER->MET), A: 1178(ASN->ARG), A: 1184(ASP->LEU), A: 1199(ASP->VAL) | −2.00221 | −63.8718 |
| 163 | A: 1164(VAL->LYS), A: 1173(ASN->ARG), A: 1175(SER->ILE), A: 1178(ASN->ARG), A: 1184(ASP->HIE), A: 1190(ALA->MET) | −2.41927 | −63.7744 |
| 164 | A: 1164(VAL->HID), A: 1173(ASN->ARG), A: 1175(SER->ARG), A: 1178(ASN->ARG), A: 1184(ASP->LEU), A: 1199(ASP->VAL) | −2.27711 | −63.5811 |
| 165 | A: 1164(VAL->LYS), A: 1173(ASN->ARG), A: 1175(SER->MET), A: 1184(ASP->ARG), A: 1190(ALA->MET) | −2.46413 | −63.3576 |
| 166 | A: 1164(VAL->LYS), A: 1173(ASN->ARG), A: 1175(SER->MET), A: 1178(ASN->ARG), A: 1184(ASP->THR), A: 1199(ASP->VAL) | −2.91376 | −63.2499 |
| 167 | A: 1164(VAL->LYS), A: 1173(ASN->ARG), A: 1175(SER->MET), A: 1178(ASN->ARG), A: 1184(ASP->TRP), A: 1190(ALA->MET) | −2.64001 | −63.2023 |

TABLE 3-continued

| The Results of Energy Maturation by Monte Carlo Methods for Combining Several Mutations in HR2 Structure | | | |
|---|---|---|---|
| MUT # | Mutations | Δ Affinity | Δ Stability |
| 168 | A: 1164(VAL->LYS), A: 1173(ASN->ARG), A: 1175(SER->ARG), A: 1184(ASP->ARG), A: 1199(ASP->VAL) | −2.93736 | −63.0834 |
| 169 | A: 1164(VAL->LYS), A: 1173(ASN->ARG), A: 1175(SER->ARG), A: 1184(ASP->LYS), A: 1202(GLU->ASN) | −2.96397 | −62.8659 |
| 170 | A: 1164(VAL->LYS), A: 1173(ASN->ARG), A: 1175(SER->MET), A: 1184(ASP->LYS), A: 1202(GLU->ASN) | −2.68914 | −62.8447 |
| 171 | A: 1164(VAL->HID), A: 1173(ASN->ARG), A: 1175(SER->ARG), A: 1178(ASN->ARG), A: 1184(ASP->VAL), A: 1190(ALA->MET) | −1.99285 | −62.8164 |
| 172 | A: 1164(VAL->LYS), A: 1173(ASN->ARG), A: 1175(SER->MET), A: 1184(ASP->THR), A: 1202(GLU->ASN) | −2.65492 | −62.7923 |
| 173 | A: 1164(VAL->LYS), A: 1165(ASP->ARG), A: 1173(ASN->HIP), A: 1175(SER->MET), A: 1178(ASN->ARG), A: 1184(ASP->MET) | −3.88582 | −62.7674 |
| 174 | A: 1164(VAL->HID), A: 1173(ASN->ARG), A: 1175(SER->MET), A: 1178(ASN->ARG), A: 1184(ASP->PHE), A: 1202(GLU->ASN) | −1.9833 | −62.7382 |
| 175 | A: 1164(VAL->LYS), A: 1173(ASN->ARG), A: 1175(SER->MET), A: 1184(ASP->HIP), A: 1190(ALA->MET) | −2.44671 | −62.5372 |
| 176 | A: 1164(VAL->LYS), A: 1165(ASP->ARG), A: 1173(ASN->ARG), A: 1175(SER->MET), A: 1178(ASN->MET), A-1184(ASP->MET) | −3.67967 | −62.341 |
| 177 | A: 1164(VAL->LYS), A: 1175(SER->ILE), A: 1178(ASN->ARG), A: 1184(ASP->ARG), A: 1190(ALA->MET) | −1.71426 | −62.3026 |
| 178 | A: 1164(VAL->LYS), A: 1175(SER->MET), A: 1178(ASN->ARG), A: 1184(ASP->MET), A: 1190(ALA->MET) | −1.90748 | −61.8435 |
| 179 | A: 1164(VAL->LYS), A: 1178(ASN->ARG), A: 1184(ASP->ARG), A: 1190(ALA->MET), A: 1194(ASN->HIP), A: 1199(ASP->HIE) | −2.34314 | −61.5862 |
| 180 | A: 1164(VAL->HID), A: 1173(ASN->ARG), A: 1175(SER->ARG), A: 1178(ASN->ARG), A: 1184(ASP->HIP) | −1.87272 | −61.4739 |
| 181 | A: 1164(VAL->HID), A: 1173(ASN->ARG), A: 1175(SER->MET), A: 1178(ASN->ARG), A: 1184(ASP->LEU) | −1.54951 | −61.2732 |
| 182 | A: 1164(VAL->LYS), A: 1173(ASN->ARG), A: 1175(SER->ILE), A: 1178(ASN->ARG), A: 1184(ASP->ASN), A: 1190(ALA->MET) | −2.40038 | −61.2207 |
| 183 | A: 1164(VAL->LYS), A: 1165(ASP->SER), A: 1173(ASN->HIP), A: 1175(SER->MET), A: 1178(ASN->ARG), A: 1184(ASP->LEU) | −3.10441 | −61.1722 |
| 184 | A: 1164(VAL->LYS), A: 1173(ASN->ARG), A: 1175(SER->ILE), A: 1178(ASN->ARG), A: 1184(ASP->MET) | −2.22859 | −61.1545 |
| 185 | A: 1164(VAL->LYS), A: 1178(ASN->ARG), A: 1184(ASP->HIP), A: 1190(ALA->MET), A: 1194(ASN->LEU), A: 1199(ASP->HIE) | −1.93857 | −61.1541 |
| 186 | A: 1164(VAL->LYS), A: 1173(ASN->ARG), A: 1175(SER->ARG), A: 1178(ASN->ARG), A: 1184(ASP->ALA), A: 1199(ASP->VAL) | −3.15493 | −61.1074 |
| 187 | A: 1164(VAL->HID), A: 1165(ASP->SER), A: 1173(ASN->HIP), A: 1175(SER->MET), A: 1178(ASN->ARG), A: 1184(ASP->LEU) | −2.25286 | −61, 056 |
| 188 | A: 1164(VAL->LYS), A: 1173(ASN->ARG), A: 1175(SER->MET), A: 1178(ASN->ARG), A: 1184(ASP->THR) | −2.45804 | −61.042 |
| 189 | A: 1164(VAL->LYS), A: 1178(ASN->ARG), A: 1184(ASP->HIP), A: 1190(ALA->MET), A: 1194(ASN->HIP), A: 1199(ASP->HIE) | −2.32895 | −60.9551 |
| 190 | A: 1164(VAL->LYS), A: 1165(ASP->SER), A: 1173(ASN->ARG), A: 1175(SER->MET), A: 1178(ASN->MET), A: 1184(ASP->LEU) | −2.90263 | −60.9092 |
| 191 | A: 1164(VAL->LYS), A: 1173(ASN->ARG), A: 1175(SER->MET), A: 1178(ASN->ARG), A: 1184(ASP->PHE), A: 1190(ALA->MET) | −2.63509 | −60.9004 |
| 192 | A: 1164(VAL->LYS), A: 1173(ASN->ARG), A: 1175(SER->MET), A: 1178(ASN->ARG), A: 1184(ASP->LYS) | −2.49057 | −60.8806 |
| 193 | A: 1164(VAL->LYS), A: 1175(SER->MET), A: 1178(ASN->ARG), A: 1184(ASP->ALA), A: 1202(GLU->ASN) | −2.10775 | −60.8756 |
| 194 | A: 1164(VAL->LYS), A: 1165(ASP->ARG), A: 1173(ASN->ARG), A: 1175(SER->MET), A: 1178(ASN->GLN), A: 1184(ASP->MET) | −3.57056 | −60.8698 |
| 195 | A: 1164(VAL->LYS), A: 1175(SER->MET), A: 1178(ASN->ARG), A: 1184(ASP->HIP), A: 1199(ASP->VAL) | −2.21569 | −60.8561 |
| 196 | A: 1164(VAL->LYS), A: 1175(SER->ARG), A: 1178(ASN->ARG), A: 1184(ASP->HIP), A: 1199(ASP->VAL) | −2.50428 | −60.837 |
| 197 | A: 1164(VAL->LYS), A: 1175(SER->MET), A: 1178(ASN->ARG), A: 1184(ASP->ILE), A: 1190(ALA->MET) | −1.85736 | −60.8231 |
| 198 | A: 1164(VAL->HID), A: 1165(ASP->SER), A: 1173(ASN->ARG), A: 1175(SER->MET), A: 1178(ASN->MET), A: 1184(ASP->LEU) | −2.0521 | −60.8007 |
| 199 | A: 1164(VAL->LYS), A: 1173(ASN->ARG), A: 1175(SER->ARG), A: 1178(ASN->ARG), A: 1184(ASP->LYS) | −2.77682 | −60.3913 |
| 200 | A: 1164(VAL->LYS), A: 1175(SER->ILE), A: 1178(ASN->MET), A: 1184(ASP->ARG), A: 1190(ALA->MET), A: 1194(ASN->HIP) | −2.0909 | −60.035 |
| 201 | A: 1164(VAL->LYS), A: 1178(ASN->ARG), A: 1184(ASP->LEU), A: 1190(ALA->MET), A: l194(ASN->HIP), A: 1199(ASP->HIE) | −2.23391 | −60, 0169 |
| 202 | A: 1164(VAL->LYS), A: 1178(ASN->ARG), A: 1184(ASP->LEU), A: 1190(ALA->MET), A: 1194(ASN->LEU), A: 1199(ASP->HIE), | −1.8501 | −59.9887 |
| 203 | A: 1164(VAL->LYS), A: 1173(ASN->ARG), A: 1175(SER->MET), A: 1184(ASP->MET), A: 1190(ALA->MET) | −2.41103 | −59.8778 |
| 204 | A: 1164(VAL->LYS), A: 1173(ASN->ARG), A: 1175(SER->ILE), A: 1184(ASP->ARG), A: 1190(ALA->MET) | −2.24587 | −59.5636 |

TABLE 3-continued

The Results of Energy Maturation by Monte Carlo Methods for Combining Several Mutations in HR2 Structure

| MUT # | Mutations | Δ Affinity | Δ Stability |
|---|---|---|---|
| 205 | A: 1164(VAL−>HID), A: 1173(ASN−>ARG), A: 1175(SER−>ARG), A: 1178(ASN−>ARG), A: 1184(ASP−>LYS) | −1.88721 | −59.5589 |
| 206 | A: 1164(VAL−>LYS), A: 1165(ASP−>SER), A: 1173(ASN−>ARG), A: 1175(SER−>MET), A: 1178(ASN−>GLN), A: 1184(ASP−>LEU) | −2.79297 | −59.4426 |
| 207 | A: 1164(VAL−>HID), A: 1165(ASP−>SER), A: 1173(ASN−>ARG), A: 1175(SER−>MET), A: 1178(ASN−>GLN), A: 1184(ASP−>LEU) | −1.941 | −59.3255 |
| 208 | A: 1164(VAL−>LYS), A: 1173(ASN−>ARG), A: 1175(SER−>MET), A: 1184(ASP−>ALA), A: 1202(GLU−>ASN) | −2.62115 | −59.299 |
| 209 | A: 1164(VAL−>LYS), A: 1175(SER−>ILE), A: 1178(ASN−>ARG), A: 1184(ASP−>MET), A: 1190(ALA−>MET) | −1.65888 | −59.2057 |
| 210 | A: 1164(VAL−>LYS), A: 1173(ASN−>ARG), A: 1175(SER−>MET), A: 1184(ASP−>ILE), A: 1190(ALA−>MET) | −2.35596 | −58.7707 |
| 211 | A: 1164(VAL−>HID), A: 1175(SER−>ARG), A: 1178(ASN−>ARG), A: 1184(ASP−>HIP), A: 1190(ALA−>MET) | −1.32787 | −58.6361 |
| 212 | A: 1164(VAL−>HID), A: 1178(ASN−>ARG), A: 1184(ASP−>ARG), A: 1190(ALA−>MET), A: 1194(ASN−>LEU), A: 1199(ASP−>HIE) | −1.07475 | −58.6274 |
| 213 | A: 1164(VAL−>LYS), A: 1175(SER−>ARG), A: 1178(ASN−>ARG), A: 1184(ASP−>LEU), A: 1199(ASP−>VAL) | −2.44453 | −58.5548 |
| 214 | A: 1164(VAL−>LYS), A: 1175(SER−>1LE), A: 1178(ASN−>GLN), A: 1184(ASP−>ARG), A: 1190(ALA−>MET), A: 1194(ASN−>HIP) | −2.00642 | −58.5309 |
| 215 | A: 1164(VAL−>LYS), A: 1175(SER−>MET), A: 1178(ASN−>ARG), A: 1184(ASP−>LEU), A: 1199(ASP−>VAL) | −2.15956 | −58.3528 |
| 216 | A: 1164(VAL−>HID), A: 1175(SER−>ILE), A: 1178(ASN−>ARG), A: 1184(ASP−>ARG), A: 1190(ALA−>MET), A: 1194(ASN−>HIP) | −1.39562 | −58.2628 |
| 217 | A: 1164(VAL−>LYS), A: 1175(SER−>ILE), A: 1178(ASN−>ARG), A: 1184(ASP−>ARG), A: 1190(ALA−>ARG), A: 1194(ASN−>HIP) | 0.571404 | −58.22 |
| 218 | A: 1164(VAL−>LYS), A: 1173(ASN−>ARG), A: 1175(SER−>MET), A: 1178(ASN−>ARG), A: 1184(ASP−>PHE), A: 1199(ASP−>VAL) | −2.90235 | −57.7798 |
| 219 | A: 1164(VAL−>LYS), A: 1178(ASN−>ARG), A: 1184(ASP−>ILE), A: 1190(ALA−>MET), A: 1194(ASN−>LEU), A: 1199(ASP−>HIE) | −1.85326 | −57.7746 |
| 220 | A: 1164(VAL−>LYS), A: 1178(ASN−>ARG), A: 1184(ASP−>ILE), A: 1190(ALA−>MET), A: 1194(ASN−>HIP), A: 1199(ASP−>HIE) | −2.2333 | −57.7722 |
| 221 | A: 1164(VAL−>LYS), A: 1173(ASN−>ARG), A: 1175(SER−>ARG), A: 1178(ASN−>ARG), A: 1184(ASP−>CYS) | −2.72911 | −57.5653 |
| 222 | A: 1164(VAL−>LYS), A: 1178(ASN−>ARG), A: 1184(ASP−>ARG), A: 1190(ALA−>MET), A: 1194(ASN−>HIP) | −2.54591 | −57.4777 |
| 223 | A: 1164(VAL−>LYS), A: 1173(ASN−>ARG), A: 1175(SER−>MET), A: 1178(ASN−>ARG), A: 1184(ASP−>ALA) | −2.41707 | −57.4453 |
| 224 | A: 1164(VAL−>HID), A: 1173(ASN−>ARG), A: 1175(SER−>ARG), A: 1178(ASN−>ARG), A: 1184(ASP−>TRP), A: 1190(ALA−>MET) | −2.02148 | −57.3468 |
| 225 | A: 1164(VAL−>LYS), A: 1173(ASN−>ARG), A: 1175(SER−>ARG), A: 1178(ASN−>ARG), A: 1184(ASP−>ALA) | −2.70191 | −57.1236 |
| 226 | A: 1164(VAL−>LYS), A: 1173(ASN−>ARG), A:1175(SER−>ARG), A: 1184(ASP−>LEU), A: 1199(ASP−>VAL) | −2.93847 | −57.0341 |
| 227 | A: 1164(VAL−>HID), A: 1173(ASN−>ARG), A: 1175(SER−>ARG), A: 1184(ASP−>HIP), A: 1190(ALA−>MET) | −1, 81954 | −56.962 |
| 228 | A: 1164(VAL−>LYS), A: 1173(ASN−>ARG), A: 1175(SER−>MET), A: 1184(ASP−>LEU), A: 1199(ASP−>VAL) | −2.67239 | −56.9136 |
| 229 | A: 1164(VAL−>LYS), A: 1165(ASP−>ARG), A: 1173(ASN−>LYS), A: 1175(SER−>MET), A: 1178(ASN−>ARG), A: 1184(ASP−>MET) | −3.77371 | −56.43 |
| 230 | A: 1164(VAL−>LYS), A: 1178(ASN−>ARG), A: 1184(ASP−>ARG), A: 1194(ASN−>LEU), A: 1199(ASP−>HIE) | −1.7807 | −56.401 |
| 231 | A: 1164(VAL−>LYS), A: 1178(ASN−>ARG), A: 1184(ASP−>ARG), A: 1190(ALA−>MET), A: 1194(ASN−>LEU) | −1.5806 | −56.2086 |
| 232 | A: 1164(VAL−>LYS), A: 1165(ASP−>ARG), A: 1173(ASN−>ARG), A: 1178(ASN−>ARG), A: 1184(ASP−>MET) | −3.93351 | −56.0908 |
| 233 | A: 1164(VAL−>LYS), A: 1173(ASN−>ARG), A: 1175(SER−>ILE), A: 1184(ASP−>MET), A: 1190(ALA−>MET) | −2.19329 | −56.0845 |
| 234 | A: 1164(VAL−>HID), A: 1178(ASN−>ARG), A: 1184(ASP−>ARG), A: 1190(ALA−>MET), A: 1194(ASN−>HIP), A: 1199(ASP−>HIE) | −1.44375 | −55.8382 |
| 235 | A: 1164(VAL−>LYS), A: 1175(SER−>ILE), A: 1178(ASN−>MET), A: 1184(ASP−>ARG), A: 1190(ALA−>MET) | −1.57359 | −56.6665 |
| 236 | A: 1164(VAL−>HID), A: 1178(ASN−>ARG), A: 1184(ASP−>HIP), A: 1190(ALA−>MET), A: 1194(ASN−>LEU), A: 1199(ASP−>HIE) | −1.04398 | −55.429 |
| 237 | A: 1164(VAL−>HID), A: 1178(ASN−>ARG), A: 1184(ASP−>HIP), A: 1190(ALA−>MET), A: 1194(ASN−>HIP), A: 1199(ASP−>HIE) | −1.42994 | −55.2321 |
| 238 | A: 1164(VAL−>LYS), A: 1165(ASP−>SER), A: 1173(ASN−>LYS), A: 1175(SER−>MET), A: 1178(ASN−>ARG), A: 1184(ASP−>LEU) | −2.99354 | −54.7792 |
| 239 | A: 1164(VAL−>LYS), A: 1165(ASP−>SER), A: 1173(ASN−>ARG), A: 1178(ASN−>ARG), A: 1184(ASP−>LEU) | −3.15365 | −54.7765 |
| 240 | A: 1164(VAL−>HID), A: 1165(ASP−>SER), A: 1173(ASN−>ARG), A: 1178(ASN−>ARG), A: 1184(ASP−>LEU) | −2.29925 | −54.6827 |
| 241 | A: 1164(VAL−>HID), A: 1165(ASP−>SER), A: 1173(ASN−>LYS), A: 1175(SER−>MET), A: 1178(ASN−>ARG), A: 1184(ASP−>LEU) | −2.14137 | −54.6386 |

TABLE 3-continued

The Results of Energy Maturation by Monte Carlo Methods for Combining Several Mutations in HR2 Structure

| MUT # | Mutations | Δ Affinity | Δ Stability |
|---|---|---|---|
| 242 | A: 1164(VAL->LYS), A: 1173(ASN->LYS), A: 1175(SER->MET), A: 1178(ASN->ARG), A: 1184(ASP->MET) | −2.29027 | −54.6029 |
| 243 | A: 1164(VAL->HID), A: 1178(ASN->ARG), A: 1184(ASP->LEU), A: 1190(ALA->MET), A: 1194(ASN->HIP), A: 1199(ASP->HIE) | −1.33444 | −54.2878 |
| 244 | A: 1164(VAL->HID), A: 1178(ASN->ARG), A: 1184(ASP->LEU), A: 1190(ALA->MET), A: 1194(ASN->LEU), A: 1199(ASP->HIE) | −0.950624 | −54.2595 |
| 245 | A: 1164(VAL->LYS), A: 1178(ASN->ARG), A: 1184(ASP->THR), A: 1190(ALA->MET), A: 1194(ASN->HIP), A: 1199(ASP->HIE) | −2.29015 | −54.1733 |
| 246 | A: 1164(VAL->LYS), A: 1178(ASN->ARG), A: 1184(ASP->THR), A: 1190(ALA->MET), A: 1194(ASN->LEU), A: 1199(ASP->HIE) | −1.90838 | −54.1509 |
| 247 | A: 1164(VAL->LYS), A: 1178(ASN->ARG), A: 1184(ASP->HIE), A: 1190(ALA->MET), A: 1194(ASN->HIP), A: 1199(ASP->HIE) | −2.28396 | −53.8287 |
| 248 | A: 1164(VAL->LYS), A: 1178(ASN->ARG), A: 1184(ASP->LYS), A: 1190(ALA->MET), A: 1194(ASN->HIP), A: 1199(ASP->HIE) | −2.31945 | −53.6853 |
| 249 | A: 1164(VAL->HID), A: 1165(ASP->ARG), A: 1173(ASN->ARG), A: 1175(SER->MET), A: 1178(ASN->ARG) | −2.81062 | −53.396 |
| 250 | A: 1164(VAL->LYS), A: 1165(ASP->ARG), A: 1173(ASN->ARG), A: 1175(SER->MET), A: 1178(ASN->ARG) | −3.6499 | −53.3685 |
| 251 | A: 1164(VAL->LYS), A: 1178(ASN->ARG), A: 1184(ASP->ARG), A: 1194(ASN->HIP), A: 1199(ASP->ILE) | −2.13751 | −53.24 |
| 252 | A: 1164(VAL->LYS), A: 1178(ASN->ARG), A: 1184(ASP->HIP), A: 1194(ASN->LEU), A: 1199(ASP->HIE) | −1.74878 | −53.2001 |
| 253 | A: 1164(VAL->HID), A: 1173(ASN->ARG), A: 1175(SER->ILE), A: 1184(ASP->HIP), A: 1190(ALA->MET) | −1.32956 | −53.1974 |
| 254 | A: 1164(VAL->LYS), A: 1178(ASN->ARG), A: 1184(ASP->HIP), A: 1190(ALA->MET), A: 1194(ASN->HIP) | −1.93039 | −53.1422 |
| 255 | A: 1164(VAL->LYS), A: 1178(ASN->ARG), A: 1184(ASP->HIP), A: 1190(ALA->MET), A: 1194(ASN->LEU) | −1.55086 | −52.972 |
| 256 | A: 1164(VAL->LYS), A: 1178(ASN->ARG), A: 1184(ASP->HIP), A: 1194(ASN->HIP), A: 1199(ASP->HIE) | −2.12473 | −52.6295 |
| 257 | A: 1164(VAL->LYS), A: 1165(ASP->SER), A: 1173(ASN->ARG), A: 1175(SER->MET), A: 1178(ASN->ARG) | −2.88468 | −52.1912 |
| 258 | A: 1164(VAL->HID), A: 1165(ASP->SER), A: 1173(ASN->ARG), A: 1175(SER->MET), A: 1178(ASN->ARG) | −2.03178 | −52.0905 |
| 259 | A: 1164(VAL->LYS), A: 1178(ASN->ARG), A: 1184(ASP->LEU), A: 1194(ASN->LEU), A: 1199(ASP->HIE) | −1.64748 | −52.0075 |
| 260 | A: 1164(VAL->LYS), A: 1168(ASP->GLN), A: 1178(ASN->ARG), A: 1184(ASP->THR), A: 1194(ASN->HIP), A: 1199(ASP->HIE) | −2.59663 | −51.9118 |
| 261 | A: 1164(VAL->LYS), A: 1184(ASP->ARG), A: 1190(ALA->MET), A: 1194(ASN->LEU), A: 1199(ASP->HIE) | −1.72345 | −51.7064 |
| 262 | A: 1164(VAL->LYS), A: 1178(ASN->ARG), A: 1184(ASP->LEU), A: 1194(ASN->HIP), A: 1199(ASP->HIE) | −2.02591 | −51.6844 |
| 263 | A: 1164(VAL->LYS), A: 1178(ASN->ARG), A: 1184(ASP->LEU), A: 1190(ALA->MET), A: 1194(ASN->LEU) | −1.45716 | −51.6508 |
| 264 | A: 1164(VAL->LYS), A: 1178(ASN->ARG), A: 1184(ASP->ASN), A: 1190(ALA->MET), A: 1194(ASN->HIP), A: 1199(ASP->HIE) | −2.26597 | −51.3284 |
| 265 | A: 1164(VAL->LYS), A: 1178(ASN->ARG), A: 1184(ASP->CYS), A: 1190(ALA->MET), A: 1194(ASN->HIP), A: 1199(ASP->HIE) | −2.27511 | −51.0564 |
| 266 | A: 1164(VAL->LYS), A: 1178(ASN->ARG), A: 1184(ASP->CYS), A: 1190(ALA->MET), A: 1194(ASN->LEU), A: 1199(ASP->HIE) | −1.89015 | −50.9924 |
| 267 | A: 1164(VAL->LYS), A: 1178(ASN->ARG), A: 1184(ASP->MET), A: 1190(ALA->MET), A: 1194(ASN->HIP) | −1.89218 | −50.8508 |
| 268 | A: 1164(VAL->LYS), A: 1178(ASN->ARG), A: 1184(ASP->ASN), A: 1190(ALA->MET), A: 1194(ASN->LEU), A: 1199(ASP->HIE) | −1.87443 | −50.7509 |
| 269 | A: 1164(VAL->LYS), A: 1178(ASN->ARG), A: 1184(ASP->ALA), A: 1190(ALA->MET), A: 1194(ASN->LEU), A: 1199(ASP->HIE) | −1.86726 | −50.5608 |
| 270 | A: 1164(VAL->LYS), A: 1184(ASP->ARG), A: 1190(ALA->MET), A: 1194(ASN->HIP), A: 1199(ASP->HIE) | −2.09582 | −49.3103 |
| 271 | A: 1164(VAL->LYS), A: 1178(ASN->ARG), A: 1184(ASP->TRP), A: 1190(ALA->MET), A: 1194(ASN->LEU), A: 1199(ASP->HIE) | −1.90576 | −49.2111 |
| 272 | A: 1164(VAL->HID), A: 1178(ASN->ARG), A: 1184(ASP->VAL), A: 1190(ALA->MET), A: 1194(ASN->HIP), A: 1199(ASP->HIE) | −1.36119 | −49.0123 |
| 273 | A: 1164(VAL->LYS), A: 1184(ASP->HIP), A: 1190(ALA->MET), A: 1194(ASN->LEU), A: 1199(ASP->HIE) | −1.69181 | −48.5687 |
| 274 | A: 1164(VAL->LYS), A: 1184(ASP->HIP), A: 1190(ALA->MET), A: 1194(ASN->HIP), A: 1199(ASP->HIE) | −2.07738 | −48.5237 |
| 275 | A: 1164(VAL->HID), A: 1178(ASN->ARG), A: 1184(ASP->THR), A: 1190(ALA->MET), A: 1194(ASN->LEU), A: 1199(ASP->HIE) | −1.0066 | −48.4213 |
| 276 | A: 1164(VAL->LYS), A: 1168(ASP->GLN), A: 1178(ASN->MET), A: 1184(ASP->THR), A: 1194(ASN->HIP), A: 1199(ASP->HIE) | −2.39275 | −47.8262 |
| 277 | A: 1164(VAL->LYS), A: 1175(SER->ILE), A: 1178(ASN->ARG), A: 1190(ALA->MET), A: 1194(ASN->HIP) | −1.95965 | −47.6444 |
| 278 | A: 1i64(VAL->HID), A: 1178(ASN->ARG), A: 1184(ASP->HIP), A: 1190(ALA->MET), A: 1194(ASN->HIP) | −1.03445 | −47.445 |

TABLE 3-continued

The Results of Energy Maturation by Monte Carlo Methods for Combining Several Mutations in HR2 Structure

| MUT # | Mutations | Δ Affinity | Δ Stability |
|---|---|---|---|
| 279 | A: 1164(VAL->LYS), A: 1184(ASP->LEU), A: 1190(ALA->MET), A: 1194(ASN->HIP), A: 1199(ASP->HIE) | −1.98168 | −47.1781 |
| 280 | A: 1164(VAL->LYS), A: 1184(ASP->LEU), A: 1190(ALA->MET), A: 1194(ASN->LEU), A: 1199(ASP->HIE) | −1.59609 | −46.9553 |
| 281 | A: 1164(VAL->HID), A: 1178(ASN->ARG), A: 1184(ASP->HIP), A: 1194(ASN->HIP), A: 1199(ASP->HIE) | −1.22551 | −46.9187 |
| 282 | A: 1164(VAL->LYS), A: 1168(ASP->HIP), A: 1178(ASN->ARG), A: 1184(ASP->THR), A: 1194(ASN->LEU), A: 1199(ASP->HIE) | −2.82991 | −46.5096 |
| 283 | A: 1164(VAL->LYS), A: 1168(ASP->HIP), A: 1178(ASN->ARG), A: 1184(ASP->THR), A: 1194(ASN->HIP), A: 1199(ASP->HIE) | −3.0163 | −46.2756 |
| 284 | A: 1164(VAL->LYS), A: 1178(ASN->ARG), A: 1184(ASP->THR), A: 1190(ALA->MET), A: 1194(ASN->HIP) | −1.89486 | −46.2453 |
| 285 | A: 1164(VAL->LYS), A: 1178(ASN->ARG), A: 1184(ASP->THR), A: 1194(ASN->LEU), A: 1199(ASP->HIE) | −1.69532 | −46.1835 |
| 286 | A: 1164(VAL->LYS), A: 1178(ASN->ARG), A: 1184(ASP->LYS), A: 1190(ALA->MET), A: 1194(ASN->HIP) | −1.92686 | −45.9518 |
| 287 | A: 1164(VAL->LYS), A: 1178(ASN->ARG), A: 1184(ASP->THR), A: 1194(ASN->HIP), A: 1199(ASP->H1L) | −2.08195 | −45.9496 |
| 288 | A: 1164(VAL->LYS), A: 1168(ASP->GLN), A: 1178(ASN->ARG), A: 1193(LEU->MET), A: 1194(ASN->HIP), A: 1199(ASP->HIE) | 0.730758 | −45.8112 |
| 289 | A: 1164(VAL->LYS), A: 1178(ASN->ARG), A: 1184(ASP->THR), A: 1190(ALA->MET), A: 1194(ASN->LEU) | −1.51284 | −45.7945 |
| 290 | A: 1164(VAL->LYS), A: 1168(ASP->GLN), A: 1178(ASN->ARG), A: 1184(ASP->THR), A: 1194(ASN->HIP) | −2.19932 | −43.9543 |
| 291 | A: 1164(VAL->LYS), A: 1168(ASP->GLN), A: 1178(ASN->ARG), A: 1194(ASN->HIP), A: 1199(ASP->HIE) | −2.3087 | −43.3278 |
| 292 | A: 1164(VAL->HID), A: 1184(ASP->HIP), A: 1190(ALA->MET), A: 1194(ASN->HIP), A: 1199(ASP->HIE) | −1.17839 | −42.8006 |
| 293 | A: 1164(VAL->LYS), A: 1168(ASP->GLN), A: 1178(ASN->MET), A: 1193(LEU->MET), A: 1194(ASN->HIP), A: 1199(ASP->HIE) | −2.53737 | −41.521 |
| 294 | A: 1164(VAL->HID), A: 1178(ASN->ARG), A: 1184(ASP->PHE), A: 1190(ALA->MET), A: 1194(ASN->HIP), A: 1199(ASP->HIE) | −1.40863 | −41.2912 |
| 295 | A: 1164(VAL->LYS), A: 1184(ASP->THR), A: 1190(ALA->MET), A: 1194(ASN->LEU), A: 1199(ASP->HIE) | −1.65308 | −41.1686 |
| 296 | A: 1164(VAL->LYS), A: 1168(ASP->GLN), A: 1178(ASN->GLN), A: 1193(LEU->MET), A: 1194(ASN->LEU), A: 1199(ASP->HIE) | −2.1701 | −40.5958 |
| 297 | A: 1164(VAL->LYS), A: 1168(ASP->GLN), A: 1178(ASN->GLN), A: 1193(LEU->MET), A: 1194(ASN->HIP), A: 1199(ASP->HIE) | −2.54242 | −40.2526 |
| 298 | A: 1164(VAL->HID), A: 1165(ASP->GLN), A: 1168(ASP->GLN), A: 1178(ASN->GLN), A: 1194(ASN->HIP), A: 1199(ASP->HIE) | −2.15808 | −36.2301 |
| 299 | A: 1164(VAL->LYS), A: 1165(ASP->GLN), A: 1168(ASP->GLN), A: 1178(ASN->GLN), A: 1194(ASN->HIP), A: 1199(ASP->HIE) | −3.00511 | −35.8764 |
| 300 | A: 1164(VAL->LYS), A: 1165(ASP->GLN), A: 1168(ASP->GLN), A: 1178(ASN->GLN), A: 1194(ASN->LEU), A: 1199(ASP->HIE) | −2.62743 | −35.7392 |
| 301 | A: 1164(VAL->LYS), A: 1168(ASP->GLN), A: 1178(ASN->GLN), A: 1194(ASN->LEU), A: 1199(ASP->HIE) | −1.83659 | −35.6898 |
| 302 | A: 1164(VAL->HID), A: 1168(ASP->GLN), A: 1178(ASN->GLN), A: 1193(LEU->MET), A: 1194(ASN->HIP), A: 1199(ASP->HIE) | −1.64034 | −34.8058 |
| 303 | A: 1164(VAL->LYS), A: 1168(ASP->GLN), A: 1178(ASN->GLN), A: 1194(ASN->HIP), A: 1199(ASP->HIE) | −2.26436 | −33.9855 |
| 304 | A: 1164(VAL->HID), A: 1168(ASP->GLN), A: 1178(ASN->GLN), A: 1194(ASN->HIP), A: 1199(ASP->HIE) | −1.36231 | −32.1643 |
| 305 | A: 1164(VAL->LYS), A: 1168(ASP->GLN), A: 1178(ASN->GLN), A: 1193(LEU->MET), A: 1194(ASN->HIP) | −2.14806 | −32.0562 |
| 306 | A: 1164(VAL->LYS), A: 1178(ASN->GLN), A: 1193(LEU->MET), A: 1194(ASN->HIP), A: 1199(ASP->HIE) | −2.03995 | −31.9945 |
| 307 | A: 1164(VAL->HID), A: 1165(ASP->VAL), A: 1178(ASN->GLN), A: 1194(ASN->HIP), A: 1199(ASP->HIE) | −1.60228 | −30.9256 |
| 308 | A: 1164(VAL->HID), A: 1165(ASP->GLN), A: 1178(ASN->GLN), A: 1194(ASN->HIP), A: 1199(ASP->HIE) | −1.64634 | −29.9852 |
| 309 | A: 1164(VAL->LYS), A: 1165(ASP->GLN), A: 1178(ASN->GLN), A: 1194(ASN->HIP), A: 1199(ASP->HIE) | −2.49333 | −29.9225 |
| 310 | A: 1164(VAL->HID), A: 1165(ASP->GLN), A: 1168(ASP->GLN), A: 1194(ASN->HIP), A: 1199(ASP->HIE) | −2.10437 | −28.8455 |
| 311 | A: 1164(VAL->LYS), A: 1165(ASP->GLN), A: 1168(ASP->GLN), A: 1194(ASN->H1P), A: 1199(ASP->HIE) | −2.96153 | −28.4493 |
| 312 | A: 1164(VAL->HID), A: 1165(ASP->GLN), A: 1168(ASP->GLN), A: 1178(ASN->GLN), A: 1194(ASN->HIP) | −1.76329 | −2.8.0323 |
| 313 | A: 1164(VAL->LYS), A: 1165(ASP->GLN), A: 1168(ASP->GLN), A: 1178(ASN->GLN), A: 1194(ASN->HIP) | −2.61085 | −27.6731 |
| 314 | A: 1164(VAL->HID), A: 1165(ASP->VAL), A: 1178(ASN->GLN), A: 1199(ASP->HIE) | −1.08433 | −27.3038 |
| 315 | A: 1164(VAL->HID), A: 1165(ASP->VAL), A: 1178(ASN->GLN), A: 1194(ASN->HIP), A: 1199(ASP->TYR) | −13.5073 | −24.8788 |

TABLE 3-continued

The Results of Energy Maturation by Monte Carlo Methods for Combining Several Mutations in HR2 Structure

| MUT # | Mutations | Δ Affinity | Δ Stability |
|---|---|---|---|
| 316 | A: 1164(VAL->HID), A: 1178(ASN->GLN), A: 1199(ASP->HIE) | −0.33034 | −21.8208 |
| 317 | A: 1164(VAL->HID), A: 1178(ASN->GLN) | 0.0618879 | −13.28 |
| 318 | A: 1164(VAL->HID) | 0.110205 | −5.83216 |

TABLE 4

Peptide Sequences for Wild Type and Mutated Peptides

| Number | Description | Peptide Sequence | Mutations | SEQ ID NO: |
|---|---|---|---|---|
| #120 | WT | VDLGDISGINASVVNIQKEI DRLNEVAKNLNESLIDLQE | WT | SEQ ID NO: 1 |
| #121 | Highest Affinity | HVLGDISGINASVVQIQKEI DRLNEVAKNLHESLIYLQE | 5 | SEQ ID NO: 2 |
| #122 | $2^{nd}$ Highest Affinity, High Stability | VDLGDISGIRAMVVRIQKEI MRLNEVAKNLNESLIDLQE | 6 | SEQ ID NO: 3 |
| #123 | Highest Stability, High Affinity | LRLGDISGIRARVVRIQKEI HRLNEVAKNLNESLIDLQN | 6 | SEQ ID NO: 4 |
| #125 | High Affinity | HRLRQIRGIRARVVQIQKEI WRLNEVAKLLNESLIYLQE | 11 | SEQ ID NO: 5 |

Example 3

Cell-Cell Fusion Assays

HEK293T is an immortalized cell line derived from a human fetal kidney. A pair of previously described 293FT-based reporter cell lines that constitutively express individual split reporters (DSP1-7 and DSP8-11 proteins) (Wang et al, 2014) were used and maintained in Dulbecco's modified Eagle's medium (DMEM) containing 10/fetal bovine serum (FBS) and 1 g/mL puromycin. Calu-3 cells (ATCC HTB-55) were maintained in Eagle's minimum essential medium (EMEM) containing 10% fetal bovine serum (FBS). For the construction of transient transfection vectors, a synthetic DNA corresponding to the S gene of SARS-CoV-2 (NC_045512.2) was cloned into a lentiviral transfer plasmid (CD500B-1, SBI, Palo Alto, Calif., USA) and the VSV-G gene was cloned into pCAG plasmid.

The DSP assay using 293FT cells was performed as described previously (Yamamoto et al, 2020) to monitor SARS-CoV-2-S-mediated membrane fusion. Briefly, effector cells expressing SARS-CoV-2-S protein with DSP8-11, target cells expressing ACE2, and TMPRSS2 with DSP1-7 were seeded in 10 cm culture dishes ($4\times10^6$ cells/10 ml) one day before the assay. Two hours before the DSP assay, cells were treated with 6 μM EnduRen (Promega, Madison, Wis., USA), a substrate for *Renilla* luciferase, to activate EnduRen. One microliter of each peptide dissolved in dimethyl sulfoxide (DMSO) was added to the 384-well plates (Greiner Bioscience, Frickenhausen, Germany). Next, 50 μl of each single-cell suspension (effector and target cells) was added to the wells using a Multidrop dispenser (Thermo Fisher Scientific, Waltham, Mass., USA). After incubation at 37° C. for 4 h, luciferase activity was measured using a Centro xS960 luminometer (Berthold, Germany).

The three peptides #120 (SEQ ID. NO:1), #121 (SEQ ID. NO: 2) and #125 (SEQ ID NO: 5) showed strong inhibition of SARS-CoV-2 Spike-mediated cell-cell fusion with $IC_{50}$ values of 0.75, 0.72 and 4.4 μM, respectively. (See FIG. 1)

Example 4

SARS-CoV-2 Pseudovirus Assay

There are two routes of transmission of SARS-CoV-2, one through endocytosis and the other through the plasma membrane. VeroE6 cells are originally infected with SARS-CoV-2 by the endocytosis pathway. However, induction of TMPRSS2 expression causes them to be strongly dependent on the plasma membrane route of infection, as is the case with Calu-3 cells (Hoffmann et al, 2020).

293T cells were transfected with an expression plasmid for SARS-CoV-2-S, VSV-G, or control expression plasmid by calcium-phosphate precipitation. At 16 h post-transfection, the cells were inoculated with a replication-deficient VSV, VSV-ΔGLuci, which lacks the VSV-G gene and encodes firefly luciferase, at an MOI=1 as described previously (Tani et al, 2010). After 2 h of incubation, cells were washed with DMEM and further incubated for 16 h before supernatants containing the pseudotyped viral particles were harvested. Cellular debris was removed from the supernatants using a syringe filter with a 0.2 μm size pore (Millipore, Bedford, Mass., USA).

For an infection assay, target Calu-3 cells were seeded in 96-well plates ($5\times10^4$ cells/100 dl) one day before the assay. Cells were pre-treated with peptides for 1 h before infection.

Pseudotyped viral particles were added to cells with the peptides. After 2 h of incubation, the culture supernatant was removed, and cells were washed with EMEM. Cells were further incubated in EMEM containing 10% FBS without peptides and pseudotyped viral particles. At 16 h post-infection, luciferase activity was measured using the Bright-Glo Luciferase Assay System (Promega) and Centro xS960 luminometer (Berthold).

Figure 2:
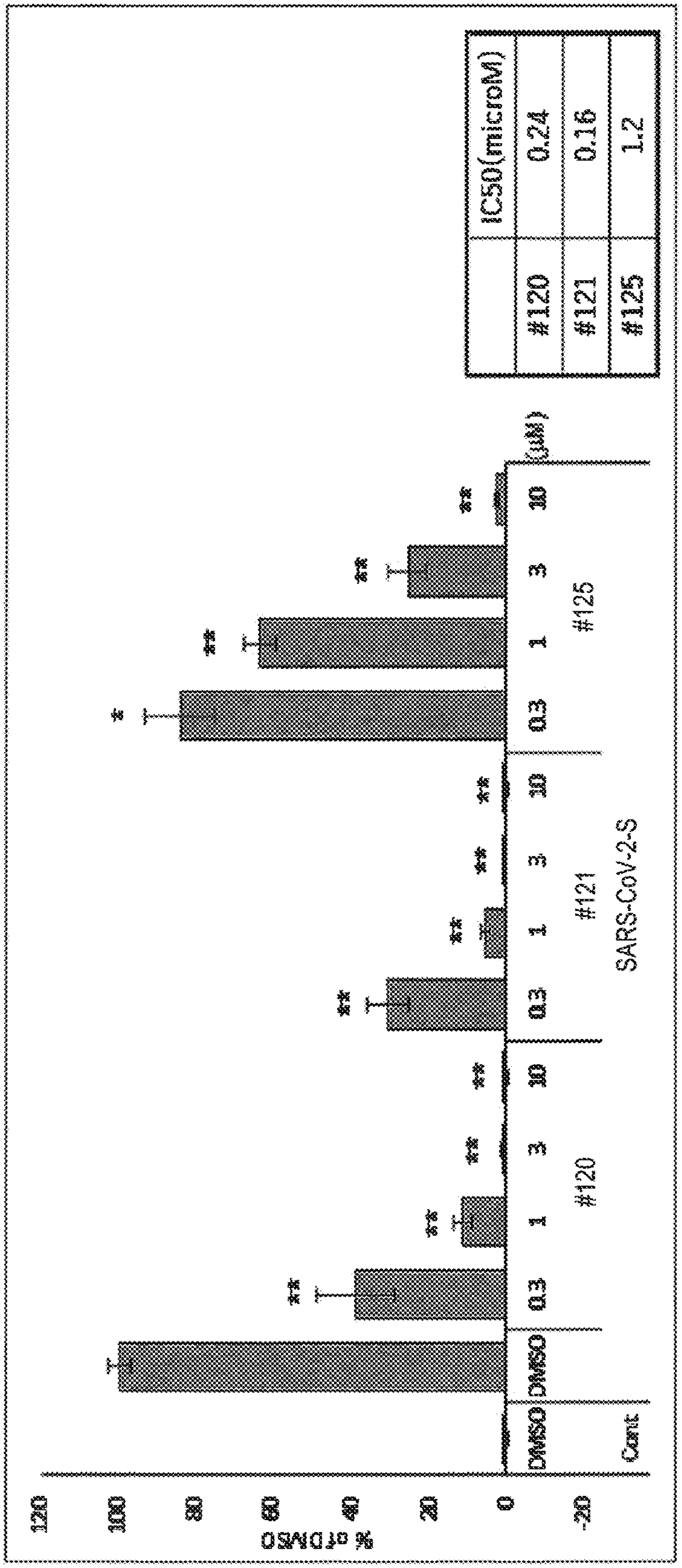
FIG. 2 depicts a graph of the effect of anti-SARS-CoV-2 fusion peptides on SARS-CoV-2 S-mediated viral infection of Calu-3 cells with SARS-CoV-2 S pseudotyped VSV viral particles. The relative infectivity was represented as the RLU normalized to that of the control assay with DMSO alone. (*: $p<0.05$, **: $p<0.01$).
Figure 3A:
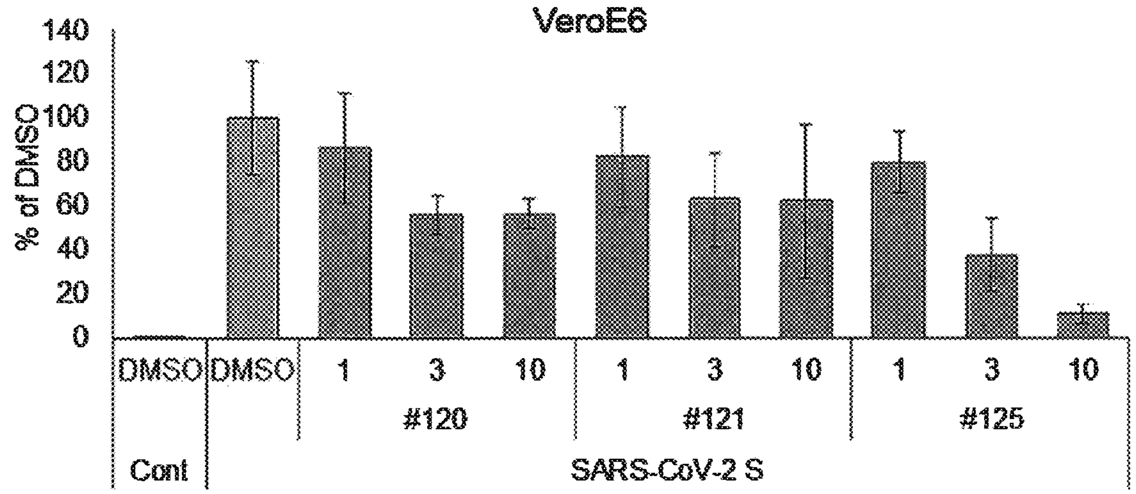
FIG. 3A depicts a graph of the effect of anti-SARS-CoV-2 fusion peptides on TMPRSS2-independent viral infection (VeroE6 cells). The relative infectivity was represented as the RLU normalized to that of the control assay with DMSO alone.
Figure 3B:
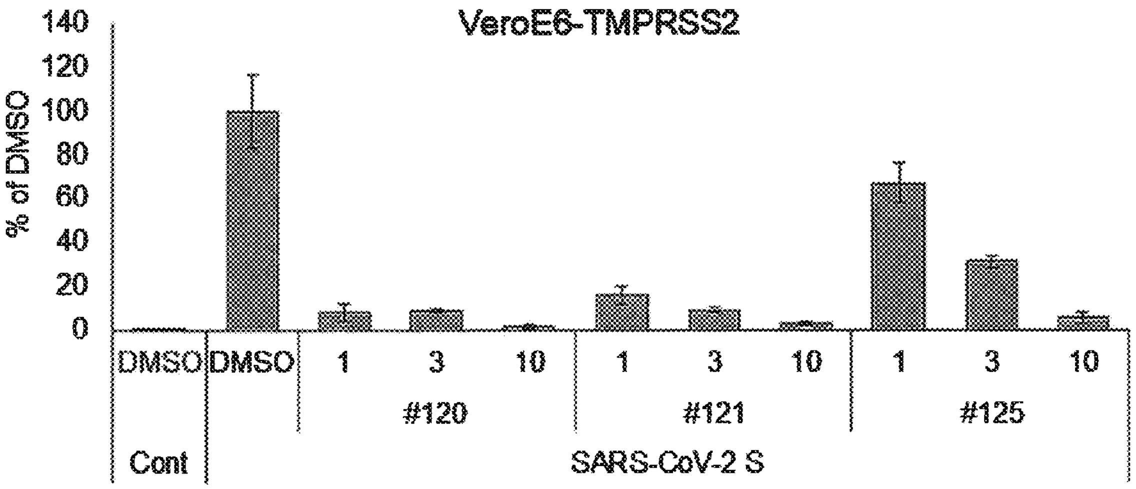
FIG. 3B depicts a graph of the effect of anti-SARS-CoV-2 fusion peptides on TMPRSS2-dependent viral infection (VeroE6-TMPRSS2 cells with SARS-CoV-2 s pseudotyped VSV viral particles. The relative infectivity was represented as the RLU normalized to that of the control assay with DMSO alone.

The three peptides #120 (SEQ ID NO: 1), #121 (SEQ ID NO: 2) and #125 (SEQ ID NO: 5) showed strong inhibition of SARS-CoV-2 pseudovirus infection in Calu-3 cells with $IC_{50}$ values of 0.24, 0.16 and 1.2 μM, respectively. (See FIG. 2) Furthermore, peptides #120 (SEQ ID NO: 1) and #121 (SEQ ID NO: 2) showed a strong inhibition of TMPRSS2-dependent pseudovirus infection through plasma membrane in both Calu-3 cells and VeroE6-TMPRSS2 cells (FIG. 2 and FIG. 3B), but only up to 44% (#120 (SEQ ID NO: 1)) and 38% (#121 (SEQ ID NO: 2)) inhibition against the infection through the endocytosis pathway in VeroE6 cells (FIG. 3A). On the other hand, peptide #125 (SEQ ID: NO: 5) strongly inhibited both the TMPRSS2-dependent plasma membrane pathway in VeroE6-TMPRSS2 cells and the endocytosis pathway in VeroE6 cells with $IC_{50}$ values of 1.7 μM and 2.4 μM, respectively (FIGS. 3A and 3B).

Example 5

SARS-CoV-2 RNA Quantification Assay

Calu-3 cells were placed at $1\times10^1$ cells in a 96 well plate. Cells were incubated with SARS-CoV-2 isolated from a patient in Japan (Yamamoto et al., 2020) at a multiplicity of infection (MOI) of 0.01 in the presence of peptides for 30 min. Then, cells were washed with fresh medium and incubated for 24 hours with the peptides. cDNA from total cellular RNA were generated using SuperPrep® II Cell Lysis & RT Kit for qPCR (TOYOBO, Osaka, Japan) according to the manufacturer's instructions. cDNA derived from SARS-CoV-2 viral RNA was measured by real-time polymerase chain reaction (PCR) using the following primers, 5'-AAATTTTGGGGACCAGGAAC-3' (SEQ ID NO: 6) and 5'-TGGCAGCTGTGTAGGTCAAC-3' (SEQ ID NO: 7) for GAPDH and 5'-GCACCGTCAAGGCTGAGAAC-3' (SEQ ID NO: 8) and 5'-TGGTGAAGACGCCAGTGG A-3' (SEQ ID NO: 9) for SARS-CoV-2 N.

Figure 4:
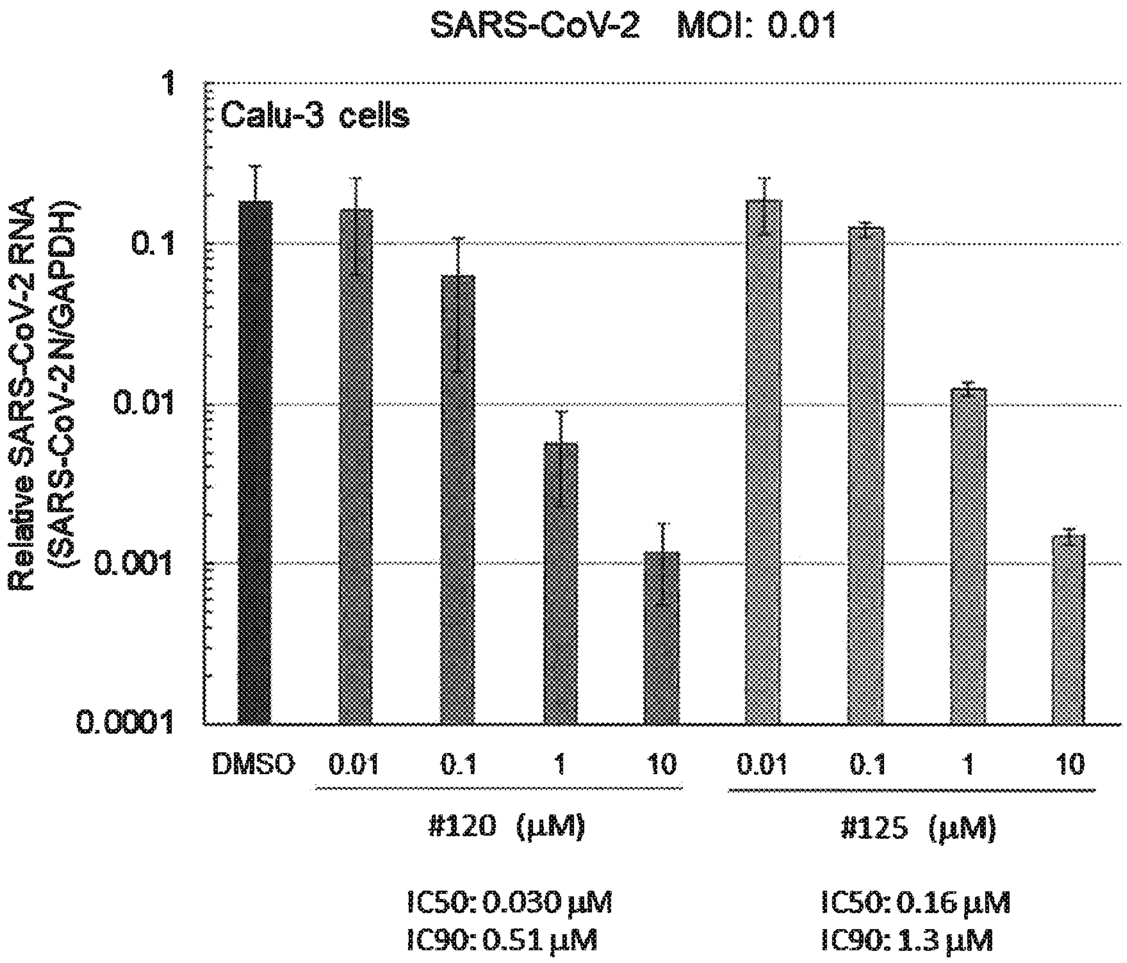
FIG. 4 depicts a graph of the effect of anti-SARS-CoV-2 fusion peptides on SARS-CoV-2 infection in Calu-3 cells. Calu-3 cells were challenged with SARS-CoV-2 at an MOI of 0.01 in the presence of the peptides at the indicated doses. The amount of internalized viral RNA was quantified by real-time PCR at 24 h after infection.

The two peptides (#120 (SEQ ID NO: 1) and #125 (SEQ ID NO: 5)) showed a strong inhibition of SARS-CoV-2 infection in Calu-3 cells with $IC_{50}$ and $IC_{90}$ values of 0.03 and 0.51 μM for #120 (SEQ ID NO: 1), and 0.16 and 1.3 μM for #125 (SEQ ID NO: 5) (FIG. 4).

Example 6

Plaque Inhibition Assay

A SARS-CoV-2 plaque inhibition assay was performed using African green monkey kidney Vero E6 cells purchased from the Korean Cell Line Bank (Seoul, Korea). The cells were incubated in 95% air and 5% $CO_2$ at 37° C. in Dulbecco's modified Eagle's medium (DMEM, Thermo Fisher Scientific, Waltham, Mass., USA) containing 10% fetal bovine serum (FBS, Thermo Fisher Scientific), 25 mM HEPES, 100 U/mL penicillin, and 100 μg/mL streptomycin. SARS-CoV-2 (NCCP No. 43326) was provided by the National Culture Collection for Pathogens (Osong, Korea).

Vero E6 cells ($2\times10^5$ cells/well) were cultured in 6-well plate at 37° C. in a $CO_2$ incubator overnight. The cells were washed with phosphate-buffered saline (PBS) and then added SARS-CoV-2 in PBS at MOI 0.01. The plates were incubated for 1 h at 37° C. in a $CO_2$ incubator and then 2 mL of DMEM containing 2% FBS was added to each well. The plates were incubated at 37° C. in a $CO_2$ incubator for 3 days. The virus culture supernatants were harvested and centrifuged at 2,000 rpm for 10 min at 4° C. to remove cell debris. The amplified viruses were quantified by plaque assay. Vero E6 cells ($7\times10^5$ cells/well) were plated in 6-well plates and then cultured until a monolayer was formed at 37° C. in $CO_2$ incubator. The cells were washed with PBS and infected with 10-fold serial dilutions of the amplified SARS-CoV-2 culture supernatants. After 1 h incubation, the supernatants were removed and the wells were overlaied with 3 mL DMEM/F12 medium (Thermo Fisher Scientific) containing 2% Oxoid agar and N-p-Tosyl-L-phenylalanine chloromethyl ketone (TPCK, 1 μg/mL)-treated trypsin. Plaques were allowed to develop for 3 days at 37° C. Plates were stained with crystal violet (0.1% crystal violet in 20% methanol) for 1 h, prior to enumeration. SARS-CoV-2 amplification and cell culture procedures were performed according to biosafety level 3 (BSL-3) conditions.

Figure 5A:
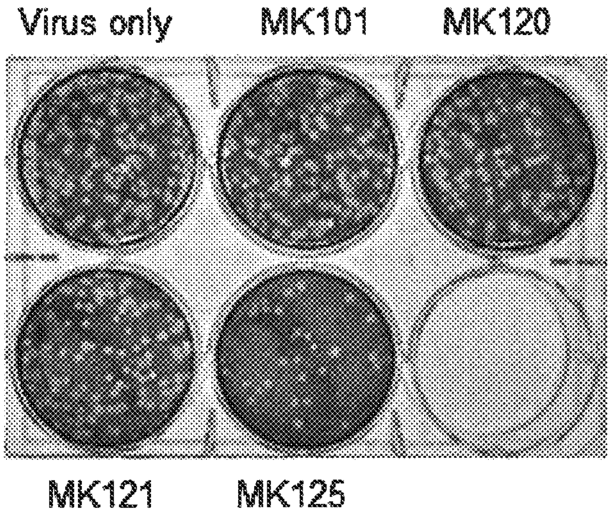
FIGS. 5A-5B depict 5(A) Vero E6 cells infected with SARS-CoV-2 where SARS-CoV-2 was incubated with each peptide prior to infection (prior to SARS-CoV-2 infection, SARS-CoV-2 was incubated with each peptide (10 μM) for 30 min at 37° C. and then added to Vero E6 cells and each well was overlaid with DMEM/F12 containing 2% Oxoid agar and TPCK (1 μg/mL)-treated trypsin, cultured for 3 days, stained with crystal violet, and then plaques were counted); and 5(B) a graph showing the effect of anti-SARS-CoV-2 fusion peptides on SARS-CoV-2 infection.
Figure 5B:
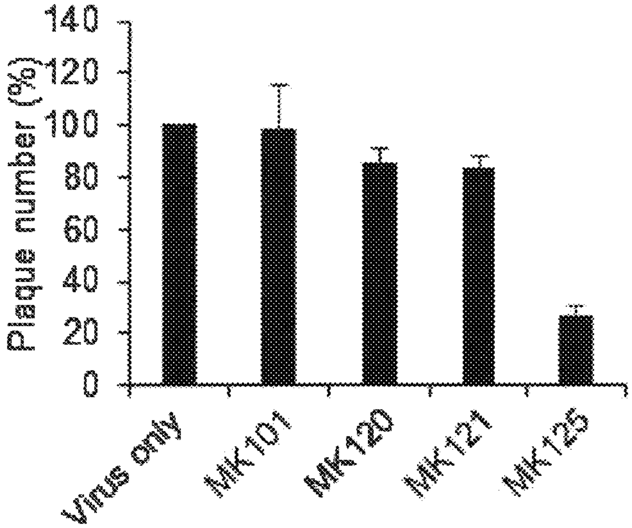
Figure 5C:
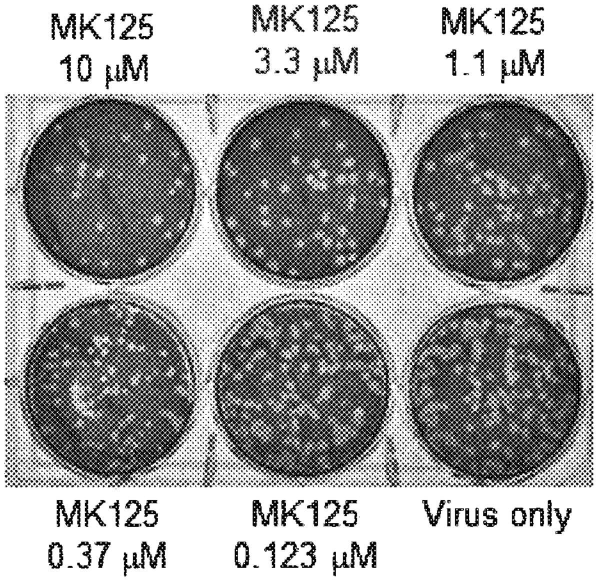
FIGS. 5C-5D depict 5(C) Vero E6 cells infected with SARS-CoV-2 where SARS-CoV-2 was incubated with peptide #125 (SEQ ID NO: 5) (prior to infection SARS-CoV-2 was pre-incubated with three-fold serially diluted #125 peptide (SEQ ID NO: 5) (n=3) for 30 min at 37° C., the vero E6 cells were infected with the mixture of the virus and peptide, incubated for 3 days in DMEM/F12 containing 2% Oxoid agar and TPCK (1 μg/mL)-treated trypsin, each well was stained with crystal violet, and then plaques were counted; and 5(D) a graph of the inhibitory effect of #125 peptide (SEQ ID. NO: 5) on SARS-CoV-2 infection in Vero E6 cells.
Figure 5D:
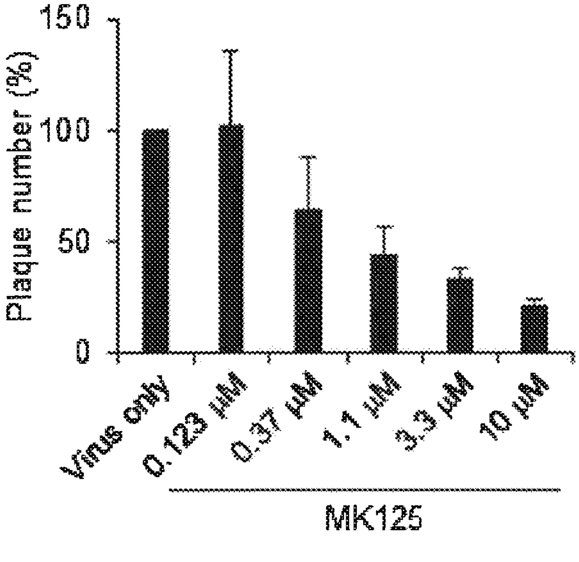

To investigate inhibitory activities of peptides against SARS-CoV-2 infection, we performed plaques inhibition assay in Vero E6 cells. At 10 μM concentration, peptides were able to reduce SARS-CoV-2 plaques formation by 15-74%. Among these peptides, #125 (SEQ ID NO: 5) was observed 75% reduction in SARS-CoV-2 plaques formation. #120 (SEQ ID NO: 1) and #121 (SEQ ID NO: 2) peptide showed approximately 15% inhibition of SARS-CoV-2 plaques (FIG. 5A). Treatment with #125 peptide (SEQ ID NO: 5) significantly inhibited the SRAS-CoV-2 plaque formation in a dose-dependent manner. The estimated $IC_{50}$ values for #125 peptide (SEQ ID NO: 5) was 0.46 μM (FIG. 5B).

Example 7

$IC_{50}$ Values of Assays

In this experiment, the inhibitory properties of three 39-mer HR2 analogue peptides were studied by different antiviral assay methods. The summary of $IC_{50}$ values in these assays is provided in Table 5.

TABLE 5

Estimated $IC_{50}$ Values for Peptides #120 (SEQ ID NO: 1), #121 (SEQ ID NO: 2), and #125 (SEQ ID NO: 5) in Antiviral Assays

| | $IC_{50}$ | | |
|---|---|---|---|
| Assay | #120 | #121 | #125 |
| SARS-CoV-2 Spike-mediated cell-cell fusion | 0.75 | 0.72 | 4.4 |
| SARS-CoV-2 pseudovirus infection in Calu-3 cells | 0.24 | 0.16 | 1.2 |
| SARS-CoV-2 pseudovirus infection in VeroE6 | >10 | >10 | 2.4 |
| TMPRSS2-dependent plasma membrane pathway in VeroE6-TMPRSS2 | <1 | <1 | 1.7 |
| SARS-CoV-2 RNA quantification | 0.03 | ND | 0.16 |
| SARS-CoV-2 plaques inhibition assay | ND | ND | 0.46 |

The peptide #120 (SEQ ID NO: 1) was able to strongly decrease the viral RNA load with $IC_{50}$=0.03 μM. The pseudovirus infection was decreased in a dose dependent manner in Calu-3 cells and VeroE6-TMPRSS2, with $IC_{50}$ values in the low nanomolar range. Despite these strong inhibitory properties in the mentioned assays, #120 (SEQ ID NO: 1) did not produce significant inhibitory properties in SARS-CoV-2 pseudovirus infection in VeroE6 cells as well as in the SARS-CoV-2 plaques inhibition assay. Peptide #121 (SEQ ID NO: 2) produced a profile similar profile to #120 (SEQ ID NO: 1). This indicates strong inhibitory properties of #120 (SEQ ID NO: 1) and 121 (SEQ ID NO: 2) in membrane-mediated virus fusion process and weak effect in blocking the endocytosis pathway.

Peptide #125 (SEQ ID NO: 5) produced favorable inhibition in the range of the used antiviral assays. The peptide was effective in cell-cell fusion and pseudovirus assays in the low micromolar range. Peptide #125 (SEQ ID NO: 5) strongly inhibited the viral RNA with $IC_{50}$=0.16 μM. More importantly, peptide #125 inhibited the SARS-CoV-2 plaque inhibition assay in the nanomolar range with $IC_{50}$=0.46 μM. This indicates that peptide #125 (SEQ ID NO: 5) can block both the membrane-dependent or endocytosis-dependent virus entry to the cells.

Based on these assays, the peptides #120 (SEQ ID NO: 1), 121 (SEQ ID NO: 2) and 125 (SEQ ID NO: 5) can be a base for anti-SARS-CoV-2 therapy. Of special interest, peptide #125 (SEQ ID NO:5) inhibited the virus entry in all of the used assays and in different cell types.

It is to be understood that the anti-SARS-CoV-2 fusion peptides are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An anti-SARS CoV-2 fusion peptide comprising a peptide having an amino acid sequence selected from the group consisting of SEQ ID NO: 2, SEQ ID NO: 3, SEQ ID NO: 4, SEQ ID NO: 5.

2. The anti-SARS CoV-2 fusion peptide of claim 1, comprising a peptide having the amino acid sequence of SEQ ID NO: 2.

3. The anti-SARS CoV-2 fusion peptide of claim 1, comprising a peptide having the amino acid sequence of SEQ ID NO: 3.

4. The anti-SARS CoV-2 fusion peptide of claim 1, comprising a peptide having the amino acid sequence of SEQ ID NO: 4.

5. The anti-SARS CoV-2 fusion peptide of claim 1, comprising a peptide having the amino acid sequence of SEQ ID NO: 5.

6. A method for conducting a SARS CoV-2 inhibition assay comprising:

(a) providing a test inhibitor;

(b) providing a reference inhibitor;

(c) conducting the SARS CoV-2 inhibition assay on the test inhibitor to obtain results for the test inhibitor;

(d) conducting the SARS CoV-2 inhibition assay on the reference inhibitor to obtain results for the reference inhibitor; and (e) comparing the results for the test inhibitor to the results for the reference inhibitor to determine whether the test inhibitor inhibits SARS CoV-2;

wherein the reference inhibitor comprises the anti-SARS CoV-2 fusion peptide of claim 1.

7. The method of claim 6, wherein the assay is a cell-cell fusion assay.

8. The method of claim 6, wherein the assay is a SARS CoV-2 plaque formation assay.

9. A pharmaceutical composition comprising the anti-SARS CoV-2 fusion peptide of claim 1 and a pharmaceutically acceptable carrier.

10. A pharmaceutical composition comprising an expression system encoding at least one peptide comprising an amino acid sequence selected from the group consisting of SEQ ID NOs: 2-5, and a combination thereof.

11. The pharmaceutical composition of claim 10, wherein the expression system encodes a peptide comprising the amino acid sequence of SEQ ID NO: 2.

12. The pharmaceutical composition of claim 10, wherein the expression system encodes a peptide comprising the amino acid sequence of SEQ ID NO: 3.

13. The pharmaceutical composition of claim 10, wherein the expression system encodes a peptide comprising the amino acid sequence of SEQ ID NO: 4.

14. The pharmaceutical composition of claim 10, wherein the expression system encodes a peptide comprising the amino acid sequence of SEQ ID NO: 5.

15. A method of inhibiting SARS CoV-2 infection of a cell comprising administering a composition comprising at least one peptide according to claim 1 or a combination thereof to a subject in need thereof.

16. The method of claim 15, wherein the peptide comprises a peptide the amino acid sequence of SEQ ID NO: 2.

17. The method of claim 15, wherein the peptide comprises a peptide having the amino acid sequence of SEQ ID NO: 5.

* * * * *